United States Patent [19]

Grell et al.

[11] Patent Number: 5,068,325
[45] Date of Patent: Nov. 26, 1991

[54] 4,5,7,8-TETRAHYDRO-6H-THIAZOLO[5,4-D]AZEPINES, THEIR PREPARATION AND THEIR USE AS PHARMACEUTICAL COMPOSITIONS

[75] Inventors: Wolfgang Grell; Rudolf Hurnaus; Manfred Reiffen, all of Biberach; Robert Sauter, Laupheim, all of Fed. Rep. of Germany; Ludwig Pichler; Walter Kobinger, both of Vienna, Austria; Michael Entzeroth, Warthausen, Fed. Rep. of Germany; Joachim Mierau, Mainz, Fed. Rep. of Germany; Gunter Schingnitz, Bad Kreuznach, Fed. Rep. of Germany

[73] Assignee: Karl Thomae GmbH, Biberach an der Riss, Fed. Rep. of Germany

[21] Appl. No.: 368,753

[22] Filed: Jun. 20, 1989

[30] Foreign Application Priority Data

Jun. 20, 1988 [DE] Fed. Rep. of Germany ....... 3820775

[51] Int. Cl.$^5$ .................... G07D 513/04; A01K 31/55
[52] U.S. Cl. ...................................... 514/215; 540/578
[58] Field of Search ........................ 540/578; 514/215

[56] References Cited

U.S. PATENT DOCUMENTS 3,804,849 4/1974 Griss ................................... 540/578

OTHER PUBLICATIONS

Goodman and Gilman, p. XII, 1985.

Primary Examiner—Robert Gerstl
Attorney, Agent, or Firm—D. E. Frankhouser; M. M. Timbers; A. R. Stempel

[57] ABSTRACT

The present invention relates to new 4,5,7,8-tetrahydro-6H-thiazolo[5,4-d]azepines of general formula II

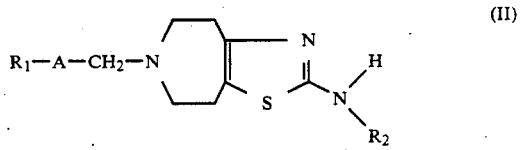

wherein the substituents are defined herein below, which compounds have valuable pharmacological properties, namely selective effects on the dopaminergic system which are achieved by stimulating (predominantly D2) dopamine receptors.

12 Claims, No Drawings

4,5,7,8-TETRAHYDRO-6H-THIAZOLO[5,4-D]AZEPINES, THEIR PREPARATION AND THEIR USE AS PHARMACEUTICAL COMPOSITIONS

British Patent No. 1321509 describes inter alia compounds of general formula I

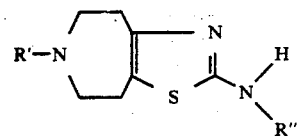

wherein

R' represents a hydrogen atom, a straight-chained or branched $C_{1-4}$-alkyl group optionally substituted by a hydroxyl group, an allyl, cycloalkyl, hexahydrobenzyl, phenyl, phenylethyl or benzyl group, whilst the benzyl group in the centre may be substituted by one or two halogen atoms, by one to three methoxy groups, or by a trifluoromethyl or alkyl group with 1 to 3 carbon atoms, and R" represents a hydrogen atom, a straight-chained or branched $C_{1-5}$-alkyl group, an allyl, cycloalkyl, phenyl, benzyl or phenylethyl group. These compounds have valuable pharmacological properties, particularly a hypotensive, sedative, antitussive and/or antiphlogistic activity.

Of the compounds described in British Patent No. 1321509, the compounds 2-amino-6-allyl-4,5,7,8- tetrahydro-6H-thiazolo[5,4-diazepine (Compound A) and 2- amino-6-(4-chloro-benzyl)-4,5,7,8-tetrahydro-6H-thiazolo[5,4-diazepine (Compound B) were subsequently investigated further.

Thus, for Compound A (=B-HT 920), its affinity for $\alpha 2$-adrenoceptors (R. Hammer, W. Kobinger and L. Pichler, Europ. J. Pharmacol. 62, 277 (1980)); their use for treating angina pectoris (DE-A-2820808, L. Benedikter et al.); their agonistic effect on dopamine autoreceptors (N.-E. Anden et al., Naunyn-Schmiedeberg's Arch. Pharmacol. 321, 100 (1982) and J. Neural Transmission 57, 129 (1983)); their in vivo inhibition of endogenous dopamine synthesis in the brain (N.-E. Anden et al., Acta pharmacol. et toxicol. 52, 51 (1983)): their inhibition of prolactin levels in the blood (V. Brantl et al., EP-A-0195888); their effect as a post-synaptic dopamine agonist on the denervated dopamine receptor in the striatum and their use as drugs for treating Parkinsonism (O. Hornykiewicz, DE-A-3503963; and D. Hinzen, O. Hornykiewicz, et al., Europ. J. Pharmacol. 131, 75 (1986)) and their affinity for dopamine-D2 receptors (G. Griss, R. Hurnaus et al.; EFMC-IXth International Symposium on Medicinal Chemistry, Berlin (West), Sept. 14-18, 1986, Short Communication No. 64, Abstract page 114) and for the compound B (=B-HT 958), its $\alpha 2$-agonistic activity with a high pre/postsynaptic activity ratio (L. Pichler, H. Hörtnagl and W. Kobinger, Naunyn-Schmiedeberg's Arch. Pharmacol. 320, 110 (1982)); its use in treating angina pectoris (DE-A-2820808, L. Benedikter et al.); its cardiovascular effects (W. Kobinger and L. Pichler, Europ. J. Pharmacol. 97, 67 (1984)); its central $\alpha 2$-antagonistic activity and its agonistic effect on dopamine autoreceptors in the brain (H. Hörtnagl, L. Pichler, U. Holzer-Petsche, O. Hornykiewicz and W. Kobinger, Europ. J. Pharmacol. 106, 335 (1985); its hypotensive and heart rate lowering activity by the stimulation of dopamine receptors (probably located in the CNS) (M. J. Brown and D. Harland, Brit. J. Pharmcol. 87, 361 (1986)) and its affinity for $\alpha 2$- and D2-receptors (G. Griss, R. Hurnaus et al.; EFMC-IXth Intern. Symp. on Medicinal Chemistry, Berlin (West), September 14-18, 1986 Short Communication No. 64, Abstract page 114) have been published.

The aim of the invention was to discover new dopaminergics with more favourable properties, which, unlike the known compounds of general formula I, have a substantially reduced affinity for $\alpha 2$-adrenoceptors, so as to reduce the risk of $\alpha 2$-induced side effects (sedation, ataxia and hypotonia).

The present invention thus relates to new 4,5,7,8-tetrahydro-6H-thiazolo[5,4-d]azepines of general formula II

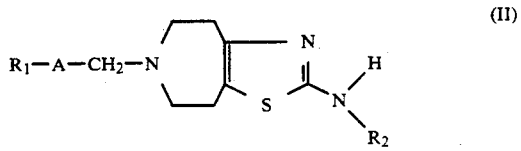

the acid addition salts thereof, and particularly for pharmaceutical use the physiologically acceptable acid addition salts thereof with inorganic or organic acids, the preparation and use thereof as pharmaceutical compositions.

The new compounds have valuable pharmacological properties, namely selective effects on the dopaminergic system caused by stimulation of (predominantly D2) dopamine receptors. In addition, analgesic and anti-inflammatory effects and serotonin-2-antagonistic activities are also observed. The compounds according to the invention are particularly suitable for treating diseases of the central nervous system such as Parkinson's disease, hyperprolactinaemia and schizophrenia and also for treating cardiovascular diseases, in view of their pharmacological properties.

In general formula II above A represents a group of the formulae

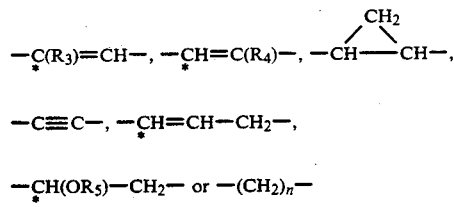

wherein n represents the numbers 2, 3 or 4, $R_3$ represents a hydrogen atom or a methyl group, $R_4$ represents a $C_{1-3}$ alkyl group or a phenyl group and $R_5$ represents a hydrogen atom, a methyl or ethyl group and the carbon atom designated * is linked to the group R1, and $R_1$ represents a phenyl group optionally monosubstituted by a halogen atom or by a $C_{1-4}$-alkoxy group, a methyl, trifluoromethyl, phenyl, nitro, amino, dimethylamino, piperidino, acetylamino, methylthio, methylsulphinyl, methylsulphonyl, cyano, aminocarbonyl, carboxy, methoxycarbonyl, ethoxycarbonyl, benzyloxy, pyridylmethoxy or hydroxy group; a phenyl group disubstituted by methoxy, benzyloxy, hydroxy or methyl groups, whilst the substituents may be identical or different, or a phenyl group trisubstituted by three methoxy groups, by three hydroxy groups or by one hydroxy or amino group and by two chlorine or bromine atoms, a pyridyl group optionally substituted by a chlorine atom or by a methyl, methoxy, benzyloxy or hydroxy group, a naphthyl, quinolyl, isoquinolyl, indolyl, furyl, thienyl, (2-indolinon)yl, carbostyril or 3,4- dihydrocarbostyril group, a thiazolyl group optionally substituted in the 2-position by a methyl or amino group, a benzothiophenyl or benzofuranyl group, a benzothiazolyl, benzoxazolyl or benzimidazolyl group optionally substituted in the 2-position by a methyl, phenyl or amino group, or A represents a carbon-carbon bond and $R_1$ represents a 1H-inden-2-yl or 1,2-dihydronaphthalin-3-yl group or a 2H-1-benzopyran-3-yl or 2H-1-benzothiopyran-3-yl group optionally substituted by one or two methyl groups and $R_2$ represents a hydrogen atom or an acetyl or propionyl group optionally substituted in the omega-position by a phenyl or 4-methoxyphenyl group.

As examples of the definitions of the groups given hereinbefore: A may represent a vinylene, 2-methylvinylene, 1-methyl-vinylene, 1-ethyl-vinylene, 1-n-propyl-vinylene, 1-isopropyl-vinylene, 1-phenyl-vinylene, cyclopropylene, ethynylene, n-2-propenylene, 2-hydroxy-ethylene, 2-methoxy-ethylene, 2-ethoxy-ethylene, ethylene, n-propylene or n-butylene group and $R_1$ represents a phenyl, 2-chloro-phenyl, 3-chloro-phenyl, 4-chloro-phenyl, 2-methoxy-phenyl, 3-methoxy-phenyl, 4-methoxy-phenyl, 2-ethoxy-phenyl, 3-ethoxy-phenyl, 4-ethoxy-phenyl, 2-n-propoxy-phenyl, 3-n-propoxy-phenyl, 4-n-propoxy-phenyl, 2-isopropoxy-phenyl, 3-isopropoxy-phenyl, 4-isopropoxy-phenyl, 2-n-butoxy-phenyl, 3-n-butoxy-phenyl, 4-n-butoxy-phenyl, 2-sec.butoxy-phenyl, 3-sec.butoxy-phenyl, 4-sec.butoxy-phenyl, 2-isobutoxy-phenyl, 3-isobutoxyphenyl, 4-isobutoxy-phenyl, 2-tert.butoxy-phenyl, 3-tert.butoxy-phenyl, 4-tert.butoxy-phenyl, 2-methyl-phenyl, 3-methyl-phenyl, 4-methyl-phenyl, 2-trifluoro-methyl-phenyl, 3-trifluoromethyl- phenyl, 4-trifluoromethyl-phenyl, 2-biphenyl, 3- biphenyl, 4-biphenyl, 2-nitro-phenyl, 3-nitro-phenyl, 4-nitro-phenyl, 2-amino-phenyl, 3-amino-phenyl, 4-amino- phenyl, 2-dimethylamino-phenyl, 3-dimethylamino-phenyl, 4-dimethylamino-phenyl, 2-piperidino-phenyl, 3-piperidino-phenyl, 4-piperidino-phenyl, 2-acetylamino-phenyl,3-acetylamino-phenyl, 3-acetylamino-phenyl, 4-acetylamino-phenyl, 2-methylthio-phenyl, 3-methylthio-phenyl, 4-methylthio-phenyl, 2-methylsulphinyl-phenyl, 3-methylsulphinyl-phenyl, 4-methylsulphinyl-phenyl, 2-methylsulphonyl-phenyl, 3-methylsulphonyl-phenyl, 4-methylsulphonyl-phenyl, 2-cyano-phenyl, 3-cyano-phenyl, 4-cyano-phenyl, 2-aminocarbonyl-phenyl, 3-aminocarbonyl-phenyl, 4- aminocarbonyl-phenyl, 2-carboxy-phenyl, 3-carboxy- phenyl, 4-carboxy-phenyl, 2-methoxycarbonyl-phenyl, 3- methoxycarbonyl-phenyl, 4-methoxycarbonyl-phenyl, 2- ethoxycarbonyl-phenyl, 3-ethoxycarbonyl-phenyl, 4- ethoxycarbonyl-phenyl, 2-benzyloxy-phenyl, 3-benzyloxy-phenyl, 4-benzyloxy-phenyl, 2-(2-pyridylmethoxy)phenyl, 3-(2-pyridylmethoxy)phenyl, 4-(2-pyridylmethoxy)phenyl, 2-(3-pyridylmethoxy)phenyl, 3-(3-pyridylmethoxy)phenyl, 4-(3-pyridylmethoxy)phenyl, 2-(4-pyridylmethoxy)phenyl, 3-(4-pyridylmethoxy)phenyl, 4-(4-pyridylmethoxy)phenyl, 2-hydroxy-phenyl, 3-hydroxy-phenyl, 4-hydroxy-phenyl, 2,3-dihydroxy-phenyl, 2,4-dihydroxy-phenyl, 2,5- dihydroxy-phenyl, 2,6-dihydroxy-phenyl, 3,4-dihydroxy-phenyl, 3,5-dihydroxy-phenyl, 2,3-dimethoxy-phenyl, 2,4- dimethoxyphenyl, 2,5-dimethoxy-phenyl, 2,6-dimethoxy-phenyl, 3,4-dimethoxy-phenyl, 3,5-dimethoxy-phenyl, 2,3- dimethyl-phenyl, 2,4-dimethyl-phenyl, 2,5-dimethyl-phenyl, 2,6-dimethyl-phenyl, 3,4-dimethyl-phenyl, 3,5- dimethyl-phenyl, 2,3-di(benzyloxy)phenyl, 2,4-di(benzyloxy)phenyl, 2,5-di(benzyloxy)phenyl, 3,4-di(benzyloxy)phenyl, 3,5-di(benzyloxy)phenyl, 2-hydroxy-3-methoxy-phenyl, 2-hydroxy-4-methoxy-phenyl, 2-hydroxy-5-methoxy-phenyl, 2-hydroxy-6-methoxy-phenyl, 3-hydroxy-2-methoxy-phenyl, 3-hydroxy-4-methoxy-phenyl, 3-hydroxy-5-methoxy-phenyl, 5-hydroxy-2-methoxy-phenyl, 4-hydroxy-2-methoxy-phenyl, 4-hydroxy-3-methoxy-phenyl, 3-benzyloxy-2-hydroxy-phenyl, 2-benzyloxy-3-methoxy-phenyl, 2-benzyloxy-4-methoxy-phenyl, 2-benzyloxy-5- methoxy-phenyl, 2-benzyloxy-6-methoxy-phenyl, 3- benzyloxy-2-methoxy-phenyl, 3-benzyloxy-4-methoxy- phenyl, 3-benzyloxy-5-methoxy-phenyl, 5-benzyloxy-2- methoxy-phenyl, 4-benzyloxy-2-methoxy-phenyl, 4- benzyloxy-3-methoxy-phenyl, 2-hydroxy-3-methyl-phenyl, 2-hydroxy-4-methyl-phenyl, 2-hydroxy-5-methyl-phenyl, 2-hydroxy-6-methyl-phenyl, 3-hydroxy-2-methyl-phenyl, 3-hydroxy-4-methyl-phenyl, 3-hydroxy-5-methyl-phenyl, 5-hydroxy-2-methyl-phenyl, 4-hydroxy-2-methyl-phenyl, 4-hydroxy-3-methyl-phenyl, 2-benzyloxy-3-methyl-phenyl, 2-benzyloxy-4-methyl-phenyl, 2-benzyloxy-5-methyl-phenyl, 3-benzyloxy-6-methyl-phenyl, 3-benzyloxy-2-methyl-phenyl, 3-benzyloxy-4-methyl-phenyl, 3-benzyloxy-5- methyl-phenyl, 5-benzyloxy-2-methyl-phenyl, 4-benzyloxy- 2-methyl-phenyl, 4-benzyloxy-3-methyl-phenyl, 2-methoxy- 3-methyl-phenyl, 2-methoxy-4-methyl-phenyl, 2-methoxy-5- methyl-phenyl, 2-methoxy-6-methyl-phenyl, 3-methoxy-2- methyl-phenyl, 3-methoxy-4-methyl-phenyl, 3-methoxy-5- methyl-phenyl, 5-methoxy-2-methyl-phenyl, 4-methoxy-2- methyl-phenyl, 4-methoxy-3-methyl-phenyl, 2,3,4- trimethoxy-phenyl, 3,4,5-trimethoxy-phenyl, 2,4,5- trimethoxy-phenyl, 2,4,6-trimethoxy-phenyl, 2,3,4- trihydroxy-phenyl, 3,4,5-trihydroxy-phenyl, 2,4,5- trihydroxy-phenyl, 2,4,6-trihydroxy-phenyl, 3,5- dichloro-4-hydroxy-phenyl, 3,5-dichloro-2-hydroxy- phenyl, 3,5-dibromo-4-hydroxy-phenyl, 3,5-dibromo-2- hydroxy-phenyl, 2-amino-3,5-dichloro-phenyl, 4-amino- 3,5-dichloro-phenyl, 2-amino-3,5-dibromo-phenyl, 4-amino-3,5-dibromo-phenyl, 2-pyridyl, 3-pyridyl, 4- pyridyl, 3-methyl-2-pyridyl, 4-methyl-2-pyridyl, 5- methyl-2-pyridyl, 6-methyl-2-pyridyl, 3-methoxy-2- pyridyl, 4-methoxy-2-pyridyl, 5-methoxy-2-pyridyl, 6- methoxy-2-pyridyl, 3-benzyloxy-2-pyridyl, 4-benzyloxy-2- pyridyl, 5-benzyloxy-2-pyridyl, 6-benzyloxy-2-pyridyl, 3-chloro-2-pyridyl, 4-chloro-2-pyridyl, 5-chloro-2- pyridyl, 6-chloro-2-pyridyl, 3-hydroxy-2-pyridyl, 4- hydroxy-2-pyridyl, 5-hydroxy-2-pyridyl, 6-hydroxy-2-pyridyl, 2-methyl-3-pyridyl, 4-methyl-3-pyridyl, 5-methyl-3-pyridyl, 6-methyl-3-pyridyl, 2-methyl-4- pyridyl, 3-methyl-4-pyridyl, 1-naphthyl, 2-naphthyl, quinolin-2-yl, quinolin-3-yl, quinolin-4-yl, quinolin-5- yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 3- indolyl, 5-indolyl, 2-furyl, 3-furyl, 2-thienyl, 3-thienyl, indolin-2-on-4-yl, indolin-2-on-5-yl, indolin-2-on-6-yl, indolin-2-on-7-yl, 5-carbostyril, 6-carbostyril, 7-carbostyril, 8-carbostyril, 3,4-dihydro-5-carbostyril, 3,4-dihydro-6-carbostyril, 3,4-dihydro-7-carbostyril, 3,4-dihydro-8-carbostyril, 2-thiazolyl, 4-thiazolyl, 5-thiazolyl, 2-methyl-4-thiazolyl, 2-methyl-5-thiazolyl, 2-amino-4-thiazolyl, 2-amino-5-thiazolyl, 2-benzothiophenyl, 3-benzothiophenyl, 4-benzothiophenyl, 5-benzothiophenyl, 6-benzothiophenyl, 7-benzothiophenyl, 2-benzofuranyl, 3-benzofuranyl, 4-benzofuranyl, 5-benzofuranyl, 6-benzofuranyl, 7-benzofuranyl, 2-benzothiazolyl, 4-benzothiazolyl, 5-benzothiazolyl, 6-benzothiazolyl, 7-benzothiazolyl, 2-methyl-4-benzothiazolyl, 2-methyl-5-benzothiazolyl, 2-methyl-6-benzothiazolyl, 2-methyl-7-benzothiazolyl, 2-phenyl-4-benzothiazolyl, 2-phenyl-5-benzothiazolyl, 2-phenyl-6-benzothiazolyl, 2-phenyl-7-benzothiazolyl, 2-amino-4-benzothiazolyl, 2-amino-5-benzothiazolyl, 2-amino-6-benzothiazolyl, 2-amino-7-benzothiazolyl, 2-benzoxazolyl, 4-benzoxazolyl, 5-benzoxazolyl, 6-benzoxazolyl, 7-benzoxazolyl, 2-methyl-4-benzoxazolyl, 2-methyl-5-benzoxazolyl, 2-methyl-6-benzoxazolyl, 2-methyl-7-benzoxazolyl, 2-phenyl-4-benzoxazolyl, 2-phenyl-5-benzoxazolyl, 2-phenyl-6-benzoxazolyl, 2-phenyl-7-benzoxazolyl, 2-amino-4-benzoxazolyl, 2-amino-5-benzoxazolyl, 2-amino-6-benzoxazolyl, 2-amino-7-benzoxazolyl, 2-benzimidazolyl, 4-benzimidazolyl, 5-benzimidazolyl, 2-methyl-4-benzimidazolyl, 2-methyl-5-benzimidazolyl, 2-phenyl-4-benzimidazolyl, 2-phenyl-5-benzimidazolyl, 2-amino-4-benzimidazolyl or 2-amino-5-benzimidazolyl group or A represents a carbon-carbon bond and $R_1$ represents a 1H-inden-2-yl, 1,2-dihydro-naphthalin-3-yl, 2H-1-benzopyran-3-yl, 2-methyl-2H-1-benzopyran-3-yl, 2,2-dimethyl-2H-1-benzopyran-3-yl, 2H-1-benzothiopyran-3-yl, 2-methyl-2H-1-benzothiopyran-3-yl or 2,2-dimethyl-2H-1-benzothiopyran-3-yl group and $R_2$ represents a hydrogen atom, an acetyl, phenylacetyl, (4-methoxy-phenyl)acetyl, propionyl, 3-phenyl-propionyl or 3-(4-methoxy-phenyl)propionyl group.

However, preferred compounds of general formula II above are those wherein $R_2$ is defined as hereinbefore, A represents a group of formulae $$-\underset{*}{C}(R_3)=CH-, \quad -\underset{*}{C}H=C(R_4)-, \quad -\underset{*}{C}H\underset{\diagdown}{\overset{CH_2}{\diagup}}CH-,$$

$$-C\equiv C-, \quad -\underset{*}{C}H=CH-CH_2-,$$

$$-\underset{*}{C}H(OR_5)-CH_2- \quad or \quad -(CH_2)_n-$$

wherein * n represents the numbers 2, 3 or 4, $R_3$ represents a hydrogen atom or a methyl group, $R_4$ represents a $C_{1-3}$-alkyl group or a phenyl group and $R_5$ represents a hydrogen atom, a methyl or ethyl group and the carbon atom designated * is linked to the group R1, and $R_1$ represents a phenyl group optionally substituted by a fluorine, chlorine or bromine atom, or by an alkoxy group with 1 to 4 carbon atoms, a methyl, trifluoromethyl, phenyl, hydroxy, benzyloxy, nitro, amino, dimethylamino, piperidino, cyano, aminocarbonyl, methoxycarbonyl, ethoxycarbonyl, methylmercapto, methylsulphinyl, methylsulphonyl or pyridylmethoxy group; a dimethoxyphenyl, dihydroxyphenyl, 4-hydroxy-3,5-dichlorophenyl, 4-hydroxy-3,5-dibromophenyl, 4-amino-3,5-dichlorophenyl, 4-amino-3,5-dibromophenyl, 3,4,5-trimethoxy-phenyl, naphthyl, 6-chloro-2-pyridyl, thienyl, furyl, quinolyl, isoquinolyl, benzothiophenyl, indolyl or indolin-2-on-4-yl group or a pyridyl group optionally substituted by a methyl group or A represents a carbon-carbon bond and $R_1$ represents a 1H-inden-2-yl, 1,2-dihydronaphthalin-3-yl or 1-benzopyran-3-yl group, particularly the compounds of general formula II wherein R1, and A are defined as hereinbefore and $R_2$ represents a hydrogen atom, and the acid addition salts thereof, particularly the physiologically acceptable acid addition salts thereof with organic or inorganic acids.

Particularly preferred compounds of general formula II are those wherein

A represents a vinylene, ethynylene, cyclopropylene or ethylene group, $R_1$ represents a phenyl group optionally substituted by a chlorine atom or by a hydroxy, methoxy, benzyloxy, isobutoxy, phenyl, nitro, amino, cyano or piperidino group; a pyridyl group optionally substituted by a methyl group, or a dimethoxyphenyl, naphthyl, isoquinolyl, 2-methyl-thiazolyl, furyl or thienyl group and $R_2$ represents a hydrogen atom, and the acid addition salts thereof, particularly the physiologically acceptable acid addition salts with organic or inorganic acids.

According to the invention the new compounds are obtained by the following processes:

a) reacting a compound of general formula III $$R_1-A-CH_2-X \qquad (III)$$

wherein

A and $R_1$ are defined as hereinbefore and X represents a nucleophilic leaving group such as a chlorine or bromine atom, a methanesulphonyloxy, trifluoromethanesulphonyloxy or tosyloxy group, with a compound of general formula IV $$H-N\underset{\diagdown}{\overset{\diagup}{\phantom{X}}}\underset{S}{\overset{\diagup}{\phantom{X}}}\underset{}{\overset{N}{\underset{\diagdown}{\phantom{X}}}}\underset{N}{\overset{H}{\underset{R_2}{\phantom{X}}}} \qquad (IV)$$

wherein $R_2$ is defined as hereinbefore.

The reaction is preferably carried out in a solvent such as acetone, dioxan, tetrahydrofuran, methylene chloride, chloroform, acetonitrile, dimethylformamide or dimethylsulphoxide, expediently in the presence of an acid binding agent such as potassium carbonate, triethylamine, pyridine or in the presence of an excess of the compound of formula IV used of one to three equivalents at temperatures of between $-10°$ and $100°$ C., but preferably at temperatures of between $0°$ and $80°$ C. It may also be advantageous if the reaction is carried out under protective gas, e.g. under nitrogen.

b) In order to prepare compounds of general formula II wherein $R_1$ has the meanings given for $R_1$ hereinbefore, with the exception of a 2-pyridyl group optionally substituted by a chlorine atom or by a methyl, methoxy, benzyloxy or hydroxy group, or a 2-quinolyl, 1-isoquinolyl, 3-isoquinolyl, 2-thiazolyl, 2-benzoxazolyl or 2-benzimidazolyl group:

Reductive amination of an aldehyde of general formula V $$R_1'-A-\overset{H}{C}=O \quad (V)$$

wherein

A is defined as hereinbefore and $R_1'$ has the meanings given for $R_1$ hereinbefore with the exception of a 2-pyridyl group optionally substituted by a chlorine atom or by a methyl, methoxy, benzyloxy or hydroxy group, or a 2-quinolyl, 1-isoquinolyl, 3- isoquinolyl, 2-thiazolyl, 2-benzoxazolyl or 2-benzimidazolyl group, with a compound of general formula IV (IV)

wherein $R_2$ is defined as hereinbefore.

The reductive amination, which is effected via the corresponding intermediately formed immonium compound, is carried out in a suitable solvent such as methanol, ethanol, tetrahydrofuran or dioxan in the presence of an acid, preferably an equivalent of an acid such as glacial acetic acid, and in the presence of a suitable reducing agent such as a complex metal hydride, but preferably in the presence of sodium cyanoborohydride, at temperatures of between $-10°$ and $50°$ C., but preferably at temperatures of between $0°$ and $20°$ C.

c) Reaction of a 5-halo-azepin-4-one of general formula VI (VI)

wherein

A and $R_1$ are defined as hereinbefore and

Y represents a bromine or chlorine atom, with a thiourea of general formula VII $$\underset{H}{\overset{NH_2}{\underset{|}{S=C-N-R_2}}} \quad (VII)$$

wherein $R_2$ is defined as hereinbefore.

The reaction is carried out in a melt or in a solvent such as ethanol, chloroform, dioxan, pyridine, tetrahydrofuran or dimethylformamide, optionally in the presence of an acid binding agent such as sodium acetate, potassium carbonate, triethylamine or pyridine at temperatures of between $0°$ and $150°$ C., but preferably at temperatures of between $50°$ and $100°$ C.

d) In order to prepare compounds of general formula II wherein $R_2$ represents a hydrogen atom:

Reaction of an azepin-4-one of general formula VIII (VIII)

wherein

A and $R_1$ are defined as hereinbefore, with a formamidine disulphide salt of general formula IX $$\left[ H-N=\overset{NH_2}{\underset{|}{C}}-S-S-\overset{NH_2}{\underset{|}{C}}=NH \right].(HZ)_2 \quad (IX)$$

wherein

Z represents a group of an inorganic or organic acid.

The reaction is carried out in a melt or in a solvent such as glycol, dimethylformamide, glacial acetic acid, propionic acid or glacial acetic acid/glycol at temperatures of between $50°$ and $150°$ C., preferably at temperatures of between $70°$ and $120°$ C.

e) In order to prepare compounds of general formula II wherein $R_1$ represents a phenyl, naphthyl, pyridyl, quinolinyl, isoquinolinyl, furyl, thienyl, benzofuryl, benzothienyl, (2-indolinon)yl, carbostyril or 3,4-dihydrocarbostyril group and A represents an ethynylene group:

Reaction of a compound of general formula X $$R_1'' \text{-} Hal \quad (X)$$

wherein $R_1''$ represents a phenyl, naphthyl, pyridyl, quinolinyl, isoquinolinyl, furyl, thienyl, benzofuryl, benzothienyl, (2-indolinon)yl, carbostyril or 3,4-dihydro-carbostyril group and Hal represents a bromine or iodine atom, with a propargyl compound of general formula XI (XI)

wherein $R_2$ is defined as hereinbefore.

The reaction is preferably carried out in a basic solvent such as diethylamine, triethylamine, triethylamine/acetonitrile or triethylamine/N,N-dimethylacetamide in the presence of catalytic amounts of copper(I)iodide and a nickel- or palladium-triphenylphosphine complex, preferably bis(triphenyl-phosphine)-palladium chloride, at temperatures of between $0°$ and $120°$ C., preferably at temperatures between $20°$ and $100°$ C.

f) In order to prepare compounds of general formula II wherein A represents a vinylene group:

Reduction of a propargyl compound of general formula XII

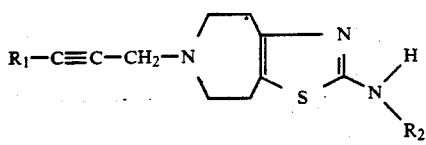

(XII)

wherein

R$_1$ and R$_2$ are defined as hereinbefore.

The reaction is carried out in a suitable solvent such as ethanol, ethyl acetate, tetrahydrofuran, glacial acetic acid or dioxan with a suitable reducing agent such as nascent hydrogen, e.g. in the presence of zinc/glacial acetic acid, tin/hydrochloric acid or tin(II)chloride/hydrochloric acid, or preferably with hydrogen, e.g. under a hydrogen pressure of 1 to 5 bar, in the presence of a suitable catalyst such as palladium/barium sulphate, at temperatures of between 0° and 50° C., preferably at ambient temperature.

During catalytic hydrogenation, the corresponding Z isomer is preferably obtained.

g) In order to prepare compounds of general formula II wherein A represents an ethylene group:

Reduction of a compound of general formula XIII

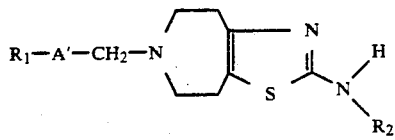

(XIII)

wherein

R$_1$ and R$_2$ are defined as hereinbefore and

A' represents a vinylene or ethynylene group.

The reduction is carried out in a suitable solvent such as ethanol, ethyl acetate, tetrahydrofuran, glacial acetic acid or dioxan with a suitable reducing agent such as nascent hydrogen, e.g. in the presence of zinc/glacial acetic acid, tin/hydrochloric acid or tin(II)chloride/hydrochloric acid, or with hydrogen, e.g. under a hydrogen pressure of from 1 to 5 bar, in the presence of a suitable catalyst such as palladium/charcoal, at temperatures of between 0° and 50° C., preferably at ambient temperature.

h) In order to prepare compounds of general formula II wherein A represents a cyclopropylene or an n-alkylene group with 2 to 4 carbon atoms and R$_2$ represents a hydrogen atom:

Reduction of an amide of general formula XIV

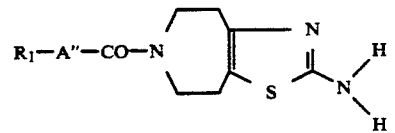

(XIV)

wherein

R$_1$ is defined as hereinbefore and A" represents a cyclopropylene or n-alkylene group with two to four carbon atoms.

The reduction is carried out in a suitable solvent such as diethylether, tetrahydrofuran, dioxan, glacial acetic acid, trifluoroacetic acid, methanol or ethanol in the presence of a suitable reducing agent such as a complex metal hydride, for example lithium aluminium hydride, sodium borohydride/boron trifluoride, sodium borohydride/aluminium chloride, diborane or borane- dimethylsulphide complex, but preferably with lithium aluminium hydride in tetrahydrofuran, at temperatures of between 0° and 80° C., preferably at temperatures of between 20° and 40° C.

i) In order to prepare compounds of general formula II wherein A represents a group of formula —CH(OR$_5$)—CH$_2$—:

Reduction of a ketone of general formula XV

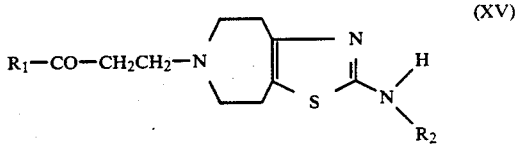

(XV)

wherein

R$_1$ and R$_2$ are defined as hereinbefore.

The reduction is carried out in a suitable solvent such as methanol, methanol/water, ethanol, ethanol/water, tetrahydrofuran/water or dioxan/water in the presence of a suitable complex metal hydride such as sodium borohydride at temperatures of between 0° and 40° C., but preferably at ambient temperature.

k) In order to prepare compounds of general formula II wherein A represents a vinylene group:

Dehydration of an alcohol of general formula XVI

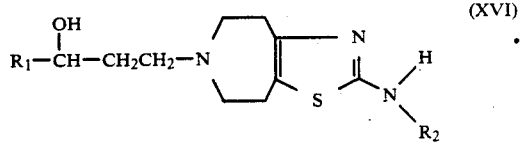

(XVI)

wherein

R$_1$ and R$_2$ are defined as hereinbefore.

The dehydration is optionally carried out in a solvent such as ethanol, isopropanol, methylene chloride, toluene or pyridine in the presence of a dehydrating agent such as phosphorus pentoxide, sulphuric acid, p-toluenesulphonic acid, p- toluenesulphonic acid chloride or an acidic ionic exchanger at temperatures of between 20° and 100° C., preferably at temperatures of between 30° and 80° C.

l) In order to prepare compounds of general formula II wherein R$_2$ represents an acetyl or propionyl group optionally substituted in the omega-position by a phenyl or 4-methoxyphenyl group:

Acylation of an amine of general formula XVII

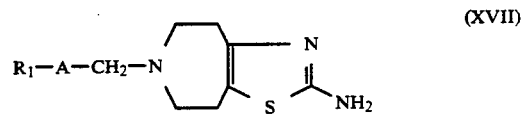

(XVII)

wherein

A and R$_1$ are defined as hereinbefore, with a carboxylic acid of general formula XVIII

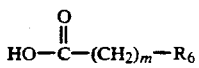

(XVIII)

wherein m represents the number 1 or 2 and

R₆ represents a hydrogen atom or a phenyl or 4-methoxyphenyl group, or with the reactive derivatives thereof optionally prepared in the reaction mixture.

Examples of reactive derivatives of a compound of general formula XVIII include the esters thereof such as the methyl, ethyl or benzyl ester, the thioesters thereof such as the methylthio- or ethylthio- ester, the halides such as the acid chloride and the anhydrides or imidazolides thereof.

The reaction is conveniently carried out in a solvent such as methylene chloride, chloroform, carbon tetrachloride, ether, tetrahydrofuran, dioxan, benzene, toluene, acetonitrile or dimethylformamide, optionally in the presence of an acid-activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyl-diimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously serve as solvents, at temperatures of between −25° and 250° C.) but preferably at temperatures of between −10° C. and the boiling temperature of the solvent used. The reaction may also be carried out without a solvent and furthermore any water formed during the reaction may be removed by azeotropic distillation, e.g. by heating with toluene using a water separator or by the addition of a drying agent such as magnesium sulphate or a molecular sieve.

m) In order to prepare compounds of general formula II wherein R₂ represents a hydrogen atom:

Deacylation of a compound of general formula XIX

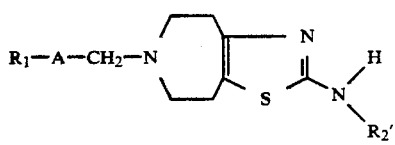

(XIX)

wherein

A and R₁ are defined as hereinbefore and R₂' represents a hydrolytically cleavable group such as an acyl or carbonic acid ester group, e.g. an acetyl, propionyl, benzoyl, methoxycarbonyl, ethoxycarbonyl or benzyloxycarbonyl group.

The deacylation is preferably carried out by hydrolysis, conveniently either in the presence of an acid such as hydrochloric, sulphuric, phosphoric or trichloroacetic acid or in the presence of a base such as sodium hydroxide or potassium hydroxide in a suitable solvent such as water, methanol, methanol/water, ethanol, ethanol/water, water/isopropanol or water/dioxan at temperatures of between −10° and 120° C., e.g. at temperatures of between ambient temperature and the boiling temperature of the reaction mixture.

n) In order to prepare compounds of general formula II wherein A has the meanings given for A hereinbefore, with the exception of the —CH(OR₅)—CH₂— group and R₁ represents a hydroxy-substituted phenyl, methylphenyl, methoxyphenyl or pyridyl group or a phenyl group substituted by two or three hydroxy groups and R₂ represents a hydrogen atom:

Ether splitting of a compound of general formula XX

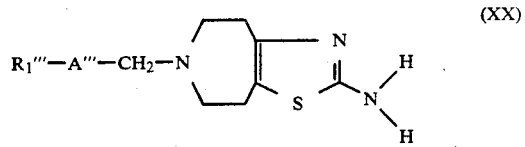

(XX)

wherein

A''' has the meanings given for A hereinbefore with the exception of the —CH(OR₅)—CH₂— group and R₁''' represents a phenyl, methylphenyl, methoxyphenyl or pyridyl group substituted by a benzyloxy or methoxy group or a phenyl group substituted by two or three benzyloxy or methoxy groups.

The ether splitting is conveniently carried out in the presence of an acid such as hydrogen chloride, hydrogen bromide, sulphuric acid, boron tribromide, aluminium trichloride or pyridine hydrochloride and expediently in a suitable solvent such as methylene chloride, glacial acetic acid or water or in mixtures thereof at temperatures of between −78° and 250° C. The ether splitting is carried out with aprotic acid conveniently at temperatures of between 0° and 150° C., preferably at temperatures of between 50° and 150° C. with a Lewis acid, preferably in a solvent such as methylene chloride at temperatures of between −78° and 20° C.

If according to the invention a compound of general formula II is obtained wherein R₁ represents a nitrophenyl group, this may be converted by reduction into a corresponding compound wherein R₁ represents an aminophenyl group, or a compound of general formula II obtained wherein R₁ represents a cyanophenyl group may be converted by hydration into a corresponding compound wherein R₁ represents an aminocarbonylphenyl group, or a compound of general formula II obtained wherein R₁ represents a cyanophenyl group may be converted by alcoholysis into a compound wherein R₁ represents a methoxycarbonylphenyl or ethoxycarbonylphenyl group, or a compound of general formula II wherein R₁ represents a cyanophenyl group may be converted by hydrolysis into a compound wherein R₁ represents a carboxyphenyl group, or a compound of general formula II wherein R₁ represents a hydroxyphenyl group may be converted by benzyl alcohol or a pyridylmethanol and an azodicarboxylic acid diester into a compound wherein R₁ represents a benzyloxyphenyl or pyridylmethoxyphenyl group.

The subsequent reduction of the nitro compound is preferably carried out in a solvent such as water, water/ethanol, methanol, glacial acetic acid, ethyl acetate or dimethylformamide, conveniently with hydrogen in the presence of a hydrogenation catalyst such as Raney nickel, platinum or palladium/charcoal, with metals such as iron, tin or zinc in the presence of an acid such as acetic, hydrochloric or sulphuric acid, with salts such as iron(II)sulphate, tin(II)chloride or sodium dithionite, or with hydrazine in the presence of Raney nickel at temperatures of between 0° and 50° C., but preferably at ambient temperature.

The subsequent hydration to yield an aminocarbonyl compound is preferably carried out by heating in polyphosphoric acid to temperatures of between 50° and 150° C., preferably to temperatures between 80° and 100° C.

Subsequent alcoholysis to yield an ester compound is expediently carried out in the presence of hydrohalic acid, preferably hydrochloric acid, and in the presence of a corresponding alcohol such as methanol or ethanol at elevated temperatures, e.g. at the boiling temperature of the reaction mixture.

The subsequent hydrolysis to yield a carboxy compound is preferably carried out in the presence of an acid such as hydrochloric, sulphuric, phosphoric or trifluoroacetic acid or in the presence of a base such as sodium hydroxide or potassium hydroxide in a suitable solvent such as water, ethanol, water/ethanol, water-/isopropanol or water/dioxan at elevated temperatures, e.g. at the boiling temperature of the reaction mixture.

Subsequent conversion into a benzyloxy or pyridyl-methoxy compound is carried out using the so- called Mitsunobu reaction, preferably in the presence of dimethyl or diethyl azodicarboxylate in an inert solvent such as tetrahydrofuran, methylene chloride or acetonitrile at temperatures of between 0° and 40° C., but preferably at ambient temperature.

Furthermore, the compounds of formula II obtained may be converted into the acid addition salts thereof, more particularly for pharmaceutical use into the physiologically acceptable salts thereof with organic or inorganic acids. Examples of such acids include hydrochloric, hydrobromic, sulphuric, phosphoric, fumaric, succinic, lactic, citric, tartaric and maleic acid.

The compounds of general formulae III to XX used as starting materials are known from the literature in some cases or may be obtained by methods known from the literature.

Thus, for example, the starting compounds III are obtained from the corresponding alcohols by reacting for example with thionylchloride, mesylchloride, phosphorus tribromide or carbon tetrabromide/triphenylphosphine. The corresponding alcohols may in turn be prepared from the corresponding aldehydes or the corresponding carboxylic acid esters by reduction. The allyl alcohols of formula $R_1$—CH=CH—CH2OH are obtained from the corresponding aldehydes by Wittig olefination with the corresponding derivatives of 2-hydroxyethylidene triphenylphosphorane, in which the hydroxy group is protected for example by ketalisation, and subsequent removal of the protecting group used.

The starting compounds V are obtained from the corresponding alcohols by oxidation for example with manganese dioxide, from the corresponding acid chlorides by reduction, for example, with organo-tin hydrides or amino-organo-silicon hydrides, from the corresponding carboxylic acids with amino-organo-silicon hydrides, for example, or if A represents a vinylene group by Wittig olefination with formylmethylene triphenylphosphorane from the corresponding aldehydes of general formula $R_1$—CH=O.

The starting compounds VIII are obtained for example from hexahydro-4H-4-azepinone hydrochloride by reacting with compounds of general formula III, preferably in dimethylformamide at ambient temperature in the presence of potassium carbonate, or by corresponding reaction of the ethylene ketal of hexahydro-4H-4-azepinone with subsequent deketalisation.

The starting compounds VI are obtained from the compounds VIII for example by reaction with bromine in glacial acetic acid in the presence of hydrogen bromide.

The starting compounds IV are partly described in GB-A-1321509.

The starting compounds of formulae XI to XV, XVII, XIX and XX are obtained from the compounds IV by reaction with the corresponding compounds with alkylation or reductive amination or acylation.

The starting compounds XVI are obtained by reduction of the compounds XV for example using sodium borohydride.

As already mentioned hereinbefore, the new compounds have valuable pharmacological properties, namely selective effects on the dopaminergic system which are achieved by stimulation of (predominantly D2) dopamine receptors. The compounds according to the invention are particularly suitable for treating diseases of the central nervous system such as Parkinson's disease, hyperprolactinaemia and schizophrenia, and also for treating cardiovascular diseases such as ischaemia and cardiogenic shock. In addition, analgesic and anti-inflammatory effects and serotonin-2-antagonistic effects are also observed as well as an inhibitory effect on granulocyte-dependent processes, e.g. on the formation of oxygen radicals. The compounds according to the invention wherein $R_2$ represents one of the acyl groups defined hereinbefore are probably prodrugs of the corresponding compounds in which $R_2$ represents a hydrogen atom.

The biological properties of the compounds according to the invention listed hereinafter were tested by the following methods:

1Determining the affinity for dopamine D2-receptors by displacement experiments with [$^3$H]-spiperone (Modified Method of W. Billard et al., Life Sci. 35, 1885 (1984) and D. J. de Vries and P. M. Beart, Eur. J. Pharmacol. 109, 417 (1985))

Membrane Preparation

Male rats (of the Chbb:Thom strain weighing about 200 g) were killed by a blow to the back of the neck. The brains were removed and dissected on ice. The striata were dissected out, weighed and homogenised in 25 volumes of tris buffer (50 mM tris-HCl, 1 mM EDTA, 5 mM $MgCl_2$ and 1 mM ascorbic acid) for 30 seconds in an Ultra-Turrax at maximum speed, followed by 10 cycles in a Potter-Elvehjem at 1400 rpm. The pellet obtained after centrifuging at 50,000×g at 4° C. for 15 minutes was again taken up in 25 ml of tris buffer and centrifuged under the above conditions. The supernatant was discarded and the pellet obtained was incubated in 25 ml of tris buffer at 37° C. for 30 minutes and then centrifuged again at 50,000×g at 4° C. for 15 minutes. Finally, the pellet obtained was mixed with tris buffer to obtain a homogenate dilution of 1:500 (based on the weight of the striata).

Binding Assay 1 ml aliquots of the membrane preparation were incubated with 1 ml of a solution of 0.25 nM [$^3$H]-spiperone (0.75 GBq/mmol, Messrs. DuPont NEN) and at increasing concentrations of the test substance ($10^{-11}$ to $10^{-4}$ M) at ambient temperature for one hour. Incubation was ended by the addition of 5 ml of ice cold tris buffer and filtration using Whatman GF/B filters. The filters were washed twice, each time with 5 ml of ice cold buffer. The radioactivity of the filters was determined by liquid scintillation measurement in Instagel$^{(R)}$ (Messrs. Canberra Packard). Non-specific binding was determined in the presence of $10^{-5}$ M haloperidol (Sigma Chemical Co.).

Data Analysis

Displacement curves were obtained from the data using the TOPFIT programming package (G. Heinzel in "Pharmacokinetics During Drug Development: Data Analysis and Evaluation Techniques", G. Bozler and J. M. van Rossum Eds., G. Fischer Verlag, Stuttgart 1982, 207).

The substances displace the radioligand in a biphasic manner which is typical of agonists; the D2-Ki values given (Ki=IC$_{50}$: $(1+C_L/K_L)$, wherein $C_L$ and $K_L$ represent the concentration and dissociation constant, respectively, of the radioligand used (see Cheng and Prusoff in Biochem. Pharmacol. 22, 3099 (1973))) relate to the high-affinity form of the dopamine receptor.

2. Determination of the affinity for alpha-2 receptors by displacement experiments with [$^3$H] clonidine (Modified Method of B. Jarrott, W. J. Louis and R. J. Summers, Biochem. Pharmacol. 27, 141 (1979))

Membrane Preparation

A male rat (Chbb:Thom strain weighing about 200 g) was killed by a blow to the back of the neck. The brain was removed and the cortex dissected out, weighed and homogenised in 25 volumes of tris buffer (50 mM tris-HCl, pH 7.50) for 30 seconds in an Ultra-Turrax at maximum speed, followed by 10° Cycles in a Potter-Elvehjem at 1400 rpm. The homogenised material was combined with tris buffer to obtain a homogenate dilution of 1:50 (based on the weight of the cortex).

Binding Assay 1 ml aliquots of the membrane preparation were incubated for three hours at ambient temperature with 1 ml of a solution of 1 nM of [$^3$H]-clonidine (2.2 TBq/mmol, Messrs. DuPont NEN) and with increasing concentrations of the test substance ($10^{-11}$ to $10^{-4}$ M). Incubation was ended by the addition of 5 ml of ice-cold tris buffer and filtration through Whatman GF/B filters. The filters were washed twice, each time with 5 ml of ice cold buffer. The radioactivity of the filters was determined by liquid scintillation measurement in Instagel(R) (Messrs. Canberra Packard). The non-specific binding was determined in the presence of $10^{-5}$ M of oxymetazoline (Sigma Chemical Co.).

Data Analysis

Displacement curves were obtained from the data using the TOPFIT programming package (G. Heinzel in "Pharmacokinetics During Drug Development: Data Analysis and Evaluation Techniques", G. Bozler and J. M. van Rossum Eds., G. Fischer Verlag, Stuttgart 1982, 207).

Table I which follows shows the D2-Ki values and α2-IC$_{50}$ values of compounds according to the invention. The quotient α2-IC$_{50}$/D2-Ki constitutes a standard number for the relative affinity of a substance for dopamine-D2 receptors compared with α2-adrenoceptors. The higher this number, the higher the D2/α2 selectivity.

TABLE 1

| Compound (Example No.) | D2-Ki [nM] | α2-IC$_{50}$ [nM] | α2-IC$_{50}$/D2-Ki |
|---|---|---|---|
| 3a | 7 | 620 | 88 |
| 3b | 24 | 810 | 145 |
| 4d | 10 | 890 | 89 |
| 4e | 3 | 190 | 63 |
| 4g | 2 | 240 | 120 |
| 4i | 13 | 2050 | 157 |
| 4o | 1.3 | 550 | 423 |
| 4p | 0.89 | 89 | 100 |
| 4t | 3.1 | 460 | 148 |
| 4u | 6.9 | 2200 | 318 |
| 4v | 8 | 2300 | 287 |
| 4w | 3 | 2200 | 733 |
| 4y | 0.73 | 300 | 410 |
| 4z | 8.4 | 3800 | 452 |
| 7a | 0.92 | 3100 | 3370 |
| 8n | 15 | 2000 | 133 |
| 8o | 14 | 3300 | 235 |
| 9 | 6.7 | 530 | 79 |
| 10 | 17 | 15000 | 882 |
| 11a | 4.3 | 760 | 176 |
| 11i | 2.6 | 1500 | 576 |
| 11 | 3.2 | 820 | 256 |
| 11p | 9.9 | 3000 | 303 |
| 12b | 4.4 | 2000 | 450 |
| 14b | 2.6 | 500 | 192 |
| 15 | 0.95 | 590 | 621 |
| 16 | 1.4 | 400 | 285 |
| 24a | 1.7 | 900 | 529 |
| Compound A | 5 | 24 | 4.8 |
| Compound B | 13 | 410 | 31.5 |
| Compound C* | 410 | 5100 | 12.4 |

*Compound C = 2-amino-6-(2-phenylethyl)-4,5,7,8-tetrahydro-6H-thiazolo[5,4-d]azepine (see GB-A-1321509)

3. Determining the affinity for serotonin-1A(5-HT1A) receptors by displacement experiments with [$^3$H]—8—OH— DPAT. (Method of S. J. Peroutka, J. Neurochem. 47, 529 (1986), modified according to H. Gozlan et al., J. Receptor Research 7. 195 (1987))

Membrane Preparation

A male rat (Chbb:Thom strain weighing about 200 g) was decapitated. The brain was removed and placed in ice-cold buffer (50 mmol/1 tris-HCl plus hydrochloric acid ad pH =7.4 at ambient temperature). The frontal cortex was dissected out; its moist weight was determined. It was homogenised in 40 times its volume of buffer (Polytron, position 6, 10 seconds), then centrifuged for 20 minutes at 45,000×g in the refrigerated centrifuge. The pellet was washed in 100 times its volume of buffer and centrifuged again as described above. The resulting pellet was resuspended in 40 times its volume of buffer and pre-incubated for 10 minutes at 37° C. Sixty times the volume of buffer were added and centrifuging was carried out as above. The resulting pellet was washed with 100 times the volume of buffer and centrifuged as above. The pellet was resuspended in buffer (0.8 ml/10 mg) and briefly homogenised in the Polytron. This homogenised tissue was cooled in ice until ready for incubation.

Binding Assay 0.8 ml of tissue homogenate (=10 mg moist weight) were incubated together with 0.1 ml of a solution of [$^3$H]-8-OH-DPAT (about 0.1 nmol/1 final concentration) and with 0.1 ml of a solution of the test substance (increase in concentration) for 30 minutes at ambient temperature (triple measurement). Incubation was stopped by rapid filtering through Whatman GF/B filters; rinsing was carried out twice, each time with 5 ml of ice cold buffer (Filter Prep, Messrs. Ismatec). The radioactivity of the filters was determined by liquid scintillation measurement. Non-specific binding was determined in the presence of $10^{-4}$ mol of serotonin.

Data Analysis

Specific binding is obtained from total binding minus non-specific binding. The averages of the three measurements were entered in a system of coordinates (abscissa (log.): concentration of test substance (mol/l), ordinate (lin.): radioactivity of the samples (×dpm). The IC$_{50}$ value is the concentration which inhibits the specific bonding of [$^3$H]—8—OH—DPAT [=[$^3$H]-hydroxy-2-(di-n-propylamino)tetraline]by 50%. 4. Determining the affinity for serotonin-2(5-HT2)-receptors by displacement experiments with [$^3$H]-spiperone (Modified Method of S. J. Peroutka et al., *Mol. Pharmacol* 16, 700 (1979))

Membrane Preparation

A male rat (Chbb:Thom strain, about 200 g) was decapitated. The brain was removed. The frontal cortex was dissected out and placed in ice cold 0.32 M saccharose solution; its moist weight was determined. It was homogenised in 10 times the volume (0.32 M) of saccharose solution for 1 minute at 800 rpm in a Potter S (made by Braun of Melsungen). The homogenised material was centrifuged for 10 minutes at 1000×g (=3,000 rpm with a rotor 8×38 ml) in a refrigerated centrifuge. The supernatant was decanted off and homogenised (Polytron, position 5, 1 minute); the sediment was discarded. 5 ml (=0.5 g moist weight) of the tissue suspension thus obtained were made up to 40 ml with buffer (50 mm tris-HCl; pH=7.7 at ambient temperature).

Binding Assay 0.8 ml of the buffered homogenised tissue (=10 mg moist weight) were incubated with 0.1 ml of a solution of [$^3$H]-spiperone (about 0.2 nmol/1 final concentration) and with 0.1 ml of a solution of the test substance (increasing concentration) for 15 minutes at 37° C. (triple measurement). Incubation was stopped by rapid filtering through a Whatman GF/B filter; rinsing was carried out 3 times, each time with 5 ml of ice cold buffer within a maximum of 10 seconds (Filter Prep Messrs. Ismatec). The radioactivity of the filters was determined by liquid scintillation measurement. The non-specific binding was determined in the presence of $10^{-4}$ mol/l ketanserine.

Data Analysis

The specific binding is obtained from the total binding minus the non-specific binding. The averages of the triple measurements are entered in a system of coordinates as in 1.3. The IC$_{50}$ value is the concentration which inhibits the specific binding of [$^3$H]-spiperone by 50%.

Table 2 which follows shows the 5-HT1A-Ki values and the 5-HT2-Ki values of compounds according to the invention:

TABLE 2

| Compound (Example No.) | 5-HT1A-Ki [nM] | 5-HT2-Ki [nM] |
| --- | --- | --- |
| 1 | 4340 | 356 |
| 4d | 14160 | 1800 |

TABLE 2-continued

| Compound (Example No.) | 5-HT1A-Ki [nM] | 5-HT2-Ki [nM] |
| --- | --- | --- |
| 4t | 350 | 26 |
| 4u | 14000 | 350 |
| 4w | 36280 | 1030 |
| 4y | 23000 | 470 |
| 7a | 1100 | 120 |
| 11p | 1770 | 558 |
| 12b | 53000 | 860 |
| 14b | 7800 | 15000 |
| 17 | 1060 | 339 |
| 24a | 3500 | 560 |
| Compound A | 4690 | 20172 |
| Compound B | not tested | 18430 |
| 8-OH-DPAT | 1.2 | 2876 |
| Ketanserine | 2830 | 7.7 |
| Serotonin | 1.1 | 2833 |

5. Motility triggering in the mouse which has been treated 24 hours earlier with reserpine (Method of D. Hinzen et al., *Europ. J. Pharmacol.* 131. 75 (1986))

This test determines predominantly agonistic effects on the hypersensitive dopamine receptor.

Description of Test

Male mice are treated 24 hours before the experiment with 5 mg/kg i.p. reserpine. The animals are kept at 25°-30° C. and treated three times with 2 ml of a 5% glucose solution in tyrode s.c. (the first time when the reserpine is given, the second time in the evening of the pre-treatment day and the third time on the morning of the test day).

Groups of 6 animals are given the test substance in a quantity of 5 mg/kg injected subcutaneously. (The injection volume is usually 0.1 ml/10 g of body weight). 30 minutes later the groups of animals are placed in the observation cages (measuring 42 x 24 x 8 cm) and fitted with an infrared lightbeam in order to measure their activity. The value measured is the frequency with which a group of 6 mice pass through the infra-red beam within 5 minutes ("running pulses/5 minutes"; mean at n=3; mean±s.e.m. at n=6).

3 to 6 groups are tested for each substance. The control animals are given isotonic saline solution s.c.; they show minimal activity (<5 running pulses per 5 minutes). The standard substance A results in 50 running pulses every 5 minutes in a dosage of 3 mg/kg s.c.; Substance B is less effective than compound A; it results in 22 running pulses every 5 minutes at 5 mg/kg s.c. If complete dosage-activity curves are plotted, the DLi50 is taken as the dosage resulting in 50 running pulses every 5 minutes.

Table 3 which follows shows the DLi50 values of compounds according to the invention.

TABLE 3

| Compound (Example No.) | DLi50 [mg/kg s.c.] |
| --- | --- |
| 4a | 1.85 |
| 8 | 0.34 |
| 11a | 0.35 |
| 11b | 0.29 |
| Compound A | 3.00 |

6. Determining the post-synaptic dopaminergic activity in MPTP monkeys (Modified Method of R. S. Burns et al., *Proc. Natl. Acad. Sci.* 80. 4546 (1983))

Description of Experiment

The neurotoxin 1-methyl-4-phenyl-1,2,3,6- tetrahydro-pyridine (MPTP) produces in humans and monkeys an irreversible syndrome which in its clinical, pathological, biochemical and pharmacological appearance is very similar to idiopathic Parkinson's disease (Markey et al., Nature 311, 464 (1984)). The reason for this similarity is that MPTP selectively destroys those dopaminergic nerve cells in the substantia nigra of the brain which are also lost by degenerative processes in Parkinson's disease. There is even some discussion that MPTP or an MPTP-like substance might be formed in the body and trigger Parkinson's disease (S. H. Snyder, Nature 311, 514 (1984)). Possibly because of the specific MPTP metabolism, the clinical formation of the MPTP-induced Parkinson syndrome has hitherto been detected only in humans and monkeys. The MPTP model produced in the rhesus monkey is therefore exceptionally suitable for testing the activity of post-synaptically acting dopamine agonists. For this purpose, rhesus monkeys were given MPTP in overall doses of up to about 6 mg/kg of body weight, until the following symptoms appeared: The animals were akinetic and unable to take water and food. They showed a typical bent posture; occasionally cataleptic states occurred. The extremities showed rigor, which was interrupted by clonic spasms during passive movement. Dopamine agonists such as B-HT 920 (=compound A), levodopa or apomorphine result in a temporary cessation of this phenomenon.

Table 4 which follows shows the minimum doses (MED) of the compounds according to the invention which are required to alleviate the Parkinson's symptoms, their duration of effect and any side effects observed. It is clear that with the compounds according to the invention there is no sedative effect or ataxia at a dosage which is several times the MED, which can be put down to the absence of a corresponding activity mediated by the $\alpha 2$- receptors.

TABLE 4

| Compound (Example No.) | Dosage [mg/kg i.m.] | Duration of activity [hours] | Side effects |
|---|---|---|---|
| 4p | 0.05 (MED) | ~2 | none |
| 4p | 0.30 | 2.0–5 | none |
| 11a | 0.05 (MED) | 1.5–2 | none |
| 11a | 3.00 | 5 | slight unease |
| 11i | 0.05 (MED) | ~1.5 | none |
| 11i | 0.20 | 2.0–5 | none |
| 14b | 0.05 (MED) | 2.0–5 | none |
| 14b | 0.50 | >5 | slight unease |
| Compound A | 0.03 (MED) | 0.5–1 | none |
| Compound B | 0.15 | 5 | sedation, ataxia |

7. Determining the affinity for dopamine D1-receptors by displacement experiments with [$^3$H1-Sch 23390

The membrane preparation and data analysis were carried out as described for determining the affinity for dopamine D$_2$- receptors.

Binding Assay 1 ml aliquots of the membrane preparation were incubated for 1 hour at ambient temperature with 1 ml of a solution of 0.25 nM [$^3$H]-Sch 23390 (2.44 TBq/mmol, Messrs. DuPont NEN) and with increasing concentrations of the test substance ($10^{-11}$ to $10^{-4}$M). Incubation was ended by the addition of 5 ml of ice cold tris buffer and filtration through Whatman GF/B filters. The filters were washed twice, each time with 5 ml of ice cold buffer. The radioactivity of the filters was determined by liquid scintillation measurement in Instagel(R) (Messrs. Canberra Packard).

The non-specific binding was determined in the presence of $10^{-6}$ M (-)-butaclamol (Research Biochemicals Inc.).

Table 5 which follows gives the D$_1$-Ki-values of compounds according to the invention:

TABLE 5

| Compound (Example No.) | D$_1$-Ki [nM] |
|---|---|
| 1b | 800 |
| 4t | 210 |
| 4x | 400 |
| 4y | 1500 |
| 7a | 180 |
| 8k | 510 |
| 11p | 920 |
| 14p | 5100 |
| 24a | 3000 |
| Compound A | 12000 |
| Compound B | 11000 |
| Compound C* | 11000 |

*see page 31 (Table 1)

No toxic side effects were detected with the compounds according to the invention tested in the dosages used in the trials.

The compounds of general formula II according to the invention and the physiologically acceptable acid addition salts thereof with organic or inorganic acids may be incorporated for pharmaceutical use, optionally together with other active substances, in conventional galenic preparations such as plain or coated tablets, capsules, powders, suppositories, solutions, emulsions or suspensions. The single dose for adults, for oral or parenteral administration, is 1 to 150 mg, preferably 2.5 to 50 mg, one to three times a day.

The Examples which follow are intended to illustrate the invention: Preparation of the starting products of general formula IV wherein R$_2$ represents a hydrogen atom or an acetyl group:

EXAMPLE (i)

a) 5-Bromo-hexahydro-4H-4-azepinone-hydrobromide 260 ml of 33% hydrogen bromide/glacial acetic acid solution are added at ambient temperature, with stirring, to a solution of 130 g (0.87 mol) of hexahydro-4H-azepin-4-one-hydrochloride (melting point: 177°–178° C.) in 975 ml of glacial acetic acid. Then, within 1.5 hours, a solution of 44.6 ml=139 g (0.87 mol) of bromine in 260 ml of glacial acetic acid is added dropwise, with stirring, at ambient temperature and the resulting mixture is stirred for a further 1.5 hours at ambient temperature. It is evaporated down to dryness in vacuo, the evaporation residue is dissolved in about 1 litre of acetone, mixed with about 0.2 litres of ethyl acetate and left to crystallise out. It is filtered through a glass frit and the filter cake is washed with about 0.2 l of ice cold acetone. It is then dried at 80° C. in a circulating air dryer. Yield: 214 g (90% of theory), Melting point: 140°–145° C.

b) 2-Amino-4,5,7,8-tetrahydro-6H-thiazolo[5,4 d]azepine-dihydrobromide 214 g (0.78 mol) of 5-bromo-hexahydro-4H-azepin-4-one-hydrobromide are added to 59.7 g (0.78 mol) of thiourea in 1.6 l of anhydrous ethanol, with stirring, at ambient temperature and the mixture is then refluxed for 3.5 hours. The reaction mixture is left to stand overnight, whilst being cooled with ice, and is filtered through a glass frit. The filter cake is washed with about 0.2 l of ice cold ethanol and with about 0.2 l of ether and then dried at 80° C. over calcium chloride in a circulating air dryer. Yield: 194 g (75% of theory), Melting point: 270°-280° C. (decomp.).

c) 2-Amino-4,5,7,8-tetrahydro-6H-thiazolo[5,4-d]azepine

A solution of 194 g (0.586 mol) of the dihydrobromide described in (ii) is stirred into 200 ml of water. 240 ml of 6N potassium hydroxide solution are added, followed immediately by 2 l of chloroform. The mixture is stirred vigorously for one hour (after 15 minutes the chloroform solution has gone dark red), the phases are separated and extraction of the aqueous alkaline phase is repeated twice more, each time with 1 l of chloroform for one hour. The combined chloroform extracts are dried over sodium sulphate, filtered through a glass frit covered with sodium sulphate and the filtrate is evaporated down in vacuo. The semi-crystalline evaporation residue is triturated with about 300 ml of ether. It is filtered and the filter cake is dried at 80° C. in a circulating air dryer. Yield: 75 g (76% of theory), Melting point: 150°-160° C. Calculated: C 49.70 H 6.55 N 24.84 Found: 49.80 6.50 24.76

EXAMPLE (ii)

a) 2-Acetylamino-6-benzyl-4,5,7,8-tetrahydro-6H-thiazolo[5,4-d]azepine

Prepared from 2-amino-6-benzyl-4,5,7,8-tetrahydro-6H-thiazolo[5,4-d]azepine (see Example 4 in GB-A-1321509, melting point of the dihydrochloride 232° C.) and 1.2 equivalents of acetic anhydride by refluxing for 2 hours. Yield: 62% of theory, Melting point: 129°-130° C.

b) 2-Acetylamino-6-benzyloxycarbonyl-4,5,7,8-tetrahydro-6H-thiazolo[5,4-d]azepine Prepared from the compound described above by dissolving in methylene chloride, adding 0.3 equivalents of ethyldiisopropylamine, cooling to 0° C. and dropwise addition of a solution of 1.1 equivalents of benzylchloroformate in methylene chloride at 0° C., stirring overnight at ambient temperature, adding another 0.55 equivalents of benzyl chloroformate and stirring for a further 2 hours, extracting with water and purifying the evaporation residue of the dried and filtered organic phase by column chromatography on silica gel (toluene-/ethyl acetate/methanol =6:3:0.5). Yield: 52% of theory, Melting point: 126°-128° C.

c) 2-Acetylamino-4,5,7,8-tetrahydro-6H-thiazolo[5,4-d]-azepine-dihydrobromide

Prepared by batch-wise addition of the compound described above to 4 equivalents of a 33% hydrogen bromide/glacial acetic acid solution, stirring at ambient temperature for one hour, adding ethyl acetate, filtering, washing the filter cake with ethyl acetate and ether and drying at 80° C./20 torr. Yield: 96% of theory, Melting point: 237°-242° C. (By dissolving in saturated potassium carbonate solution, extracting with chloroform and crystallising from acetone/ether it is possible to obtain the free base. Melting point: 154°-156° C.).

Preparation of the end products of general formula II:

EXAMPLE 1

2-Amino-6-cinnamyl-4,5,7,8-tetrahydro-6H-thiazolo[5,4-d]azepine

A solution of 2.3 g (15.1 mmol) of cinnamyl chloride in 10 ml of anhydrous dimethylformamide is added to a stirred mixture of 2.50 g (14.8 mmol) of 2-amino-4,5,7,8-tetrahydro-6H-thiazolo[5,4-d]azepine and 2.10 g (15.2 mmol) of potassium carbonate in 25 ml of anhydrous dimethylformamide. After heating to 80° C. for 2 hours in a bath, the mixture is evaporated down in vacuo and the evaporation residue is distributed between water and chloroform. From the chloroform extract dried over sodium sulphate and filtered, 6 g of reddish brown oil are obtained by evaporation and purified by column chromatography on silica gel (chloroform/methanol =5:1). Yield: 1.90 g (45% of theory), Melting point: 122°-125° C. (ether).

| | | | |
|---|---|---|---|
| Calculated: | C 67.35 | H 6.71 | N 14.73 |
| Found: | 67.45 | 6.75 | 14.89 |

For conversion into the hydrochloride 6.6 ml of 1N hydrochloric acid are added to the solution of 1.88 g (6.6 mmol) of the above base in 30 ml of methanol and the resulting mixture is evaporated to dryness in vacuo. The resulting foam is dried in vacuo over phosphorus pentoxide, initially at 60° C. and then for 2 hours at 100° C. 1.80 g of 2-amino-6-cinnamyl-4,5,7,8-tetrahydro-H-thiazolo[5,4-d]azepine-hydrochloride-hydrate are obtained, melting point 120°-125° C.

| | | | | |
|---|---|---|---|---|
| Calculated: | C 58.09 | H 6.70 | Cl 10.72 | N 12.70 |
| Found: | 58.22 | 6.60 | 11.09 | 12.66 |

The following compounds were prepared analogously to Example 1:

1a) 2-Amino-6-(1H-inden-2-yl-methyl)-4,5,7,8-tetrahydro-6H-thiazolo[5,4-d]azepine Prepared from 2-amino-4,5,7,8-tetrahydro-6H-thiazolo[5,4-d]azepine, potassium carbonate and 2-chloromethyl-1H-indene (prepared from 1H-indene, paraformaldehyde and concentrated hydrochloric acid) in anhydrous dimethylformamide for 2 hours at 50° C. Yield: 4% of theory, Melting point: 134°-138° C.

| | | | |
|---|---|---|---|
| Calculated: | C 68.67 | H 6.44 | N 14.13 |
| Found: | 68.86 | 6.40 | 13.97 |

1b) 2-Amino-6-(1,2-dihydronaphthalen-3-yl-methyl)-4,5,7,8-tetrahydro-6H-thiazolo[5,4-d]azepine Prepared from 2-amino-4,5,7,8-tetrahydro-6H-thiazolo[5,4-d]azepine, potassium carbonate and 3-chloromethyl-1,2-dihydronaphthalene (prepared from 1,2-dihydronaphthalene, paraformaldehyde and concentrated hydrochloric acid) in anhydrous dimethylformamide for 2 hours at 50° C. Yield: 29% of theory, Melting point: 158°-160° C. (ethyl acetate).

| | | | |
|---|---|---|---|
| Calculated: | C 69.43 | H 6.80 | N 13.49 |
| Found: | 69.26 | 6.86 | 13.26 |

EXAMPLE 2

2-Acetylamino-6-cinnamyl-4,5,7,8-tetrahydro-6H-thiazolo[5,4-d]azepine

The mixture of 2.60 g (7 mmol) of 2-acetylamino-4,5,7,8-tetrahydro-6H-thiazolo[5,4-d]azepine-dihydrobromide and 2.13 g (15.4 mmol) of potassium carbonate is stirred into 30 ml of anhydrous dimethylformamide for 30 minutes at 80° C., cooled to ambient temperature, mixed with 1.07 g (7 mmol) of cinnamyl chloride and heated for 2 hours at 80° C. The mixture is then evaporated down in vacuo and the evaporation residue is distributed between water and chloroform. The dried and filtered chloroform solution is evaporated down in vacuo. The evaporation residue is purified by column chromatography on silica gel (chloroform/methanol=25:1). Yield: 1.52 g (66% of theory), Melting point: 133°–135° C. (ether).

| Calculated: | C 66.04 | H 6.47 | N 12.84 |
|---|---|---|---|
| Found: | 65.90 | 6.43 | 12.95 |

The following compounds were prepared analogously to Example 2:

2a) 2-Acetylamino-6-(3-(4-chloro-phenyl)allyl)-4,5,7,8-tetrahydro-6H-thiazolo[5,4-d]azepine. 0.25 H$_2$O Prepared from 2-acetylamino-4,5,7,8-tetrahydro-6H-thiazolo[5,4-d]azepine-dihydrobromide, potassium carbonate and 4-chloro-cinnamyl chloride in anhydrous dimethylformamide. Yield: 68% of theory, Melting point: 190°–195° C. (ether).

| Calculated: (× 0.25 H$_2$O) | C 58.96 | H 5.70 | N 11.46 |
|---|---|---|---|
| Found: | 59.15 | 5.54 | 11.35 |

2b) 2-Acetylamino-6-(3-phenyl-propyl)-4,5,7,8-tetrahydro-6H-thiazole[5,4-d]azepine-hydrochloride Prepared from 2-acetylamino-4,5,7,8-tetrahydro-6H-thiazolo[5,4-d]azepine-dihydrobromide, potassium carbonate and 3-phenyl-n-propylbromide in anhydrous dimethylformamide. The base obtained is converted into the hydrochloride in ethanol using ethereal hydrochloric acid. Yield: 49% of theory, Melting point: 260°–262° C. (decomp.).

| Calculated: | C 59.08 | H 6.61 | N 11.48 | Cl 9.68 |
|---|---|---|---|---|
| Found: | 58.97 | 6.81 | 11.35 | 9.87 |

EXAMPLE 3

2-Amino-6-cinnamyl-4,5,7,8-tetrahydro-6H-thiazolo[5,4-d]azepine 1.2 g (3.7 mmol) of 2-acetylamino-6-cinnamyl-4,5,7,8-tetrahydro-6H-thiazolo[5,4-d]azepine is heated with stirring together with 24 ml of semi-concentrated hydrochloric acid for 3 hours at 90° C. Then the majority of the hydrochloric acid is eliminated in vacuo, the residue is made ammoniacal and extracted with with chloroform. The dried and filtered organic extract is evaporated down in vacuo; the evaporation residue is purified by column chromatography on silica gel (chloroform/methanol=5:1). Yield: 0.6 g (60% of theory), Melting point: 121°–124° C. (ether).

| Calculated: | C 67.35 | H 6.71 | N 14.73 |
|---|---|---|---|
| Found: | 67.37 | 6.79 | 14.92 |

The following compounds were prepared analogously to Example 3:

3a) 2-Amino-6-(3-(4-chloro-phenyl)allyl)-4,5,7,8-tetrahydro-6H-thiazolo[5,4-d]azepine Prepared from 2-acetylamino-6-(3-(4-chloro-phenyl)allyl)-4,5,7,8-tetrahydro-6H-thiazolo[5,4-d]azepine with semi-concentrated hydrochloric acid. Yield: 71% of theory, Melting point: 145°–150° C.

| Calculated: | C 60.08 | H 5.67 | N 13.14 |
|---|---|---|---|
| Found: | 60.15 | 5.48 | 12.97 |

3b) 2-Amino-6-(3-phenyl-propyl)-4,5,7,8-tetrahydro-6H-thiazolo[5,4-d]azepine-dihydrochloride. 0.33 H$_2$O Prepared from 2-acetylamino-6-(3-phenyl-propyl)-4,5,7,8-tetrahydro-6H-thiazolo[5,4-d]azepine-hydrochloride with semi-concentrated hydrochloric acid. The foam obtained by evaporating to dryness is crystallised from concentrated ethanolic solution with the addition of a little acetone. Yield: 66% of theory, Melting point: 221°–225° C.

| Calculated: (× 0.33 H$_2$O) | C 52.47 | H 6.42 | N 11.47 |
|---|---|---|---|
| Found: | 52.68 | 6.47 | 11.74 |

EXAMPLE 4

2-Amino-6-(3-(2-thienyl)allyl)-4,5,7,8-tetrahydro-6H-thiazolo[5,4-d]azepine

A solution of 1.0 g (6.2 mmol) of 3-(2=thienyl)-allyl chloride (freshly prepared from 3-(2-thienyl)allyl alcohol in chloroform by dropwise addition of one equivalent of thionyl chloride at 0° C. and, after 15 minutes at 0° C., evaporation in vacuo at 25 C) in 10 ml of chloroform is added dropwise at ambient temperature to a suspension of 1.0 g (5.9 mmol) of 2-amino-4,5,7,8- tetrahydro-6H-thiazolo[5,4-d]azepine and 0.86 9 (6.2 mmol) of potassium carbonate in 40 ml of chloroform. After 1.5 hours' stirring, 80 ml of chloroform are added and the mixture is extracted twice with water. The dried and filtered chloroform solution is evaporated down in vacuo. The evaporation residue is purified by column chromatography on silica gel (chloroform/methanol=10:1). Yield: 0.46 g (26.7% of theory), Melting point: 116°–120° C.

| Calculated: | C 57.70 | H 5.97 | N 14.42 |
|---|---|---|---|
| Found: | 57.70 | 5.86 | 14.21 |

The following compounds were prepared analogously to Example 4:

4a) 2-Amino-6-(3-(3-thienyl)allyl)-4,5,7,8-tetrahydro-6H-thiazolo[5,4-d]azepine

Prepared from 3-(3-thienyl)allyl chloride and 1 equivalent of 2-amino-4,5,7,8-tetrahydro-6H- thiazolo[5,4-d]azepine in chloroform in the presence of I equivalent of potassium carbonate. Yield: 8% of theory, Melting point: 128°–132° C. (isopropanol).

| Calculated: | C 57.70 | H 5.88 | N 14.42 |
|---|---|---|---|

| Found: | 57.93 | 5.89 | 14.28 |

4b) 2-Amino-6-(3-(3-furyl)allyl)-4,5,7,8-tetrahydro-6H-thiazolo[5,4-d]azepine Prepared from 3-(3-furyl)allyl chloride and 2 equivalents of 2-amino-4,5,7,8-tetrahydro-6H-thiazolo[5,4-d]azepine in chloroform. Yield: 30% of theory, Melting point: 130°–136° C.

| Calculated: | C 61.06 | H 6.22 | N 15.26 |
| Found: | 61.18 | 6.21 | 14.97 |

4c) 2-Amino-6-(3-(3,5-dichloro-4-hydroxy-phenyl)allyl)-4,5,7,8-tetrahydro-6H-thiazolo[5,4-d]azepine. 0.5 $H_2O$ Prepared from 3,5-dichloro-4-hydroxy-cinnamyl chloride and 2 equivalents of 2-amino-4,5,7,8-tetrahydro-6H-thiazolo[5,4-d]azepine in chloroform for 12 hours at ambient temperature. Yield: 9% of theory, Melting point: 197° C.

| Calculated: (× 0.5 $H_2O$) | C 50.66 | H 4.78 | N 11.08 |
| Found: | 50.49 | 5.06 | 10.98 |

4d) 2-Amino-6-(3-phenyl-2-propyn-1-yl)-4,5,7,8-tetrahydro-6H-thiazolo[5,4-d]azepine. 0.5 $H_2O$ Prepared from 3-phenyl-propargyl chloride and 2 equivalents of 2-amino-4,5,7,8-tetrahydro-6H-thiazolo[5,4-d]azepine in chloroform. Yield: 16% of theory, Melting point: 142°–146° C. (ether).

| Calculated: (× 0.5 $H_2O$) | C 65.74 | H 6.20 | N 14.38 |
| Found: | 65.56 | 6.01 | 14.42 |

4e) 2-Amino-6-(3-(2-chloro-phenyl)allyl)-4,5,7,8-tetrahydro-6H-thiazolo[5,4-d]azepine Prepared from 2-chloro-cinnamyl chloride and 1 equivalent of 2-amino-4,5,7,8-tetrahydro-6H-thiazolo[5,4-d]azepine in chloroform in the presence of 1 equivalent of potassium carbonate. Yield: 20% of theory, Melting point: 80° C.

| Calculated: | C 60.08 | H 5.67 | N 13.14 |
| Found: | 60.20 | 5.61 | 13.12 |

The 2-amino-6-(3-(2-chloro-phenyl)allyl))-4,5,7,8-tetrahydro-6H-thiazolo[5,4-d]azepine-dihydrochloride with a melting point of 236°–240° C. is obtained from the base by dissolving it in ethanol, adding excess ethereal hydrochloric acid and ether.

| Calculated: | C 48.93 | H 5.18 | N 10.70 |
| Found: | 49.03 | 5.31 | 10.55 |

4f) 2-Amino-6-(3-(3-chloro-phenyl)allyl)-4,5,7,8-tetrahydro-6H-thiazolo[5,4-d]azepine Prepared from 3-chloro-cinnamyl chloride and 1 equivalent of 2-amino-4,5,7,8-tetrahydro-6H-thiazolo[5,4-d]azepine in chloroform in the presence of 1 equivalent of potassium carbonate. Yield: 20% of theory, Melting point: 132°–136° C.

| Calculated: | C 60.08 | H 5.67 | N 13.14 |
| Found: | 60.20 | 5.60 | 13.26 |

4g) 2-Amino-6-(3-(2-nitro-phenyl)allyl)-4,5,7,8-tetrahydro-6H-thiazolo[5,4-d]azepine Prepared from 2-nitro-cinnamyl chloride and 2 equivalents of 2-amino-4,5,7,8-tetrahydro-6H-thiazolo[5,4-d]azepine in chloroform. Yield: 57% of theory, Melting point: 125°–128° C. (ether).

| Calculated: | C 58.17 | H 5.49 | N 16.96 |
| Found: | 57.99 | 5.70 | 16.73 |

4h) 2-Amino-6-(3-(3-nitro-phenyl)allyl)-4,5,7,8-tetrahydro-6H-thiazolo[5,4-d]azepine Prepared from 3-nitro-cinnamyl chloride and 2 equivalents of 2-amino-4,5,7,8-tetrahydro-6H-thiazolo[5,4-d]azepine in chloroform. Yield: 56% of theory, Melting point: 165°–168° C. (ether).

| Calculated: | C 58.17 | H 5.49 | N 16.96 |
| Found: | 57.97 | 5.34 | 16.89 |

4i) 2-Amino-6-(3-(4-nitro-phenyl)allyl)-4,5,7,8-tetrahydro-6H-thiazolo[5,4-d]azepine. 0.5 $H_2O$ Prepared from 4-nitro-cinnamyl chloride and 2 equivalents of 2-amino-4,5,7,8-tetrahydro-6H-thiazolo[5,4-d]azepine in chloroform. Yield: 38% of theory, Melting point: 186°–191° C. (ether).

| Calculated: (× 0.5 $H_2O$) | C 56.62 | H 5.64 | N 16.51 |
| Found: | 56.40 | 5.71 | 16.63 |

4k) 2-Amino-6-(3-(4-methoxy-phenyl)allyl)-4,5,7,8-tetrahydro-6H-thiazolo[5,4-d]azepine Prepared from 4-methoxy-cinnamyl chloride and 1 equivalent of 2-amino-4,5,7,8-tetrahydro-6H-thiazolo[5,4-d]azepine in the presence of 1 equivalent of potassium carbonate in chloroform. Yield: 10% of theory, Melting point: 155-160° C. (ether).

| Calculated: | C 64.73 | H 6.70 | N 13.32 |
| Found: | 64.58 | 6.55 | 13.16 |

4l) 2-Amino-6-(3-(2-methyl-phenyl)allyl)-4,5,7,8-tetrahydro-6H-thiazolo[5,4-d]azepine Prepared from 2-methyl-cinnamyl chloride and 2 equivalents of 2-amino-4,5,7,8-tetrahydro-6H-thiazolo[5,4-d]azepine in chloroform. Yield: 52% of theory, Melting point: 112°–115° C. (ethyl acetate).

| Calculated: | C 68.21 | H 7.07 | N 14.04 |
| Found: | 68.15 | 7.15 | 14.24 |

4m) 2-Amino-6-(3-methyl-phenyl)allyl)-4,5,7,8-tetrahydro-6H-thiazolo[5,4-d]azepine Prepared from 3-methyl-cinnamyl chloride and 2 equivalents of 2-amino-4,5,7,8-tetrahydro-6H-thiazolo[5,4-d]azepine in chloroform. Yield: 47% of theory, Melting point: 116°–119° C.

| Calculated: | C 68.21 | H 7.07 | N 14.04 |
|---|---|---|---|
| Found: | 68.14 | 7.25 | 14.34 |

4n) 2-Amino-6-(3-(4-methyl-phenyl)allyl)-4,5,7,8-tetrahydro-6H-thiazolo[5,4-d]azepine Prepared from 4-methyl-cinnamyl chloride and 1 equivalent of 2-amino-4,5,7,8-tetrahydro-6H-thiazolo[5,4-d]azepine in acetonitrile in the presence of 1 equivalent of potassium carbonate for 40 minutes at 80° C. Yield: 33% of theory, Melting point: 126°-30° C. (ether).

| Calculated: | C 68.21 | H 7.07 | N 14.04 |
|---|---|---|---|
| Found: | 68.36 | 7.17 | 14.02 |

4o) 2-Amino-6-(3-(2,3-dimethoxy-phenyl)allyl)-4,5,7,8-tetrahydro-6H-thiazolo[5,4-d]azepine Prepared from 2,3-dimethoxy-cinnamyl chloride and 2 equivalents of 2-amino-4,5,7,8-tetrahydro-6H-thiazolo[5,4-d]azepine in chloroform. Yield: 39% of theory, Melting point: 87°-9 1° C. (ether).

| Calculated: | C 62.58 | H 6.71 | N 12.16 |
|---|---|---|---|
| Found: | 62.70 | 6.89 | 12.19 |

4p) 2-Amino-6-(3-(2,5-dimethoxy-phenyl)allyl)-4,5,7,8-tetrahydro-6H-thiazolo[5,4-d]azepine Prepared from 2,5-dimethoxy-cinnamyl chloride (prepared at −5° C. for 10 minutes) and 2 equivalents of 2-amino-4,5,7,8-tetrahydro-6H-thiazolo[5,4-d]azepine in chloroform. Yield: 4% of theory, Melting point: 112°-115° C. (ether).

| Calculated: | C 62.59 | H 6.71 | N 12.17 |
|---|---|---|---|
| Found: | 62.46 | 6.67 | 11.94 |

Molecular peak (m/z) Calculated: 345 Found: 345

4q) 2-Amino-6-(3-(3,4-dimethoxy-phenyl)allyl)-4,5,7,8-tetrahydro-6H-thiazolo[5,4-d]azepine Prepared from 3,4-dimethoxy-cinnamyl chloride (prepared at −5° C. for 10 minutes) and 2 equivalents of 2-amino-4,5,7,8-tetrahydro-6H-thiazolo[5,4-d]azepine in chloroform. Yield: 7.7% of theory, Melting point: 122°-126° C. (ether).

| Calculated: | C 62.58 | H 6.71 | N 12.16 |
|---|---|---|---|
| Found: | 62.70 | 6.84 | 11.90 |

4r) 2-Amino-6-(3-(3,5-dimethoxy-phenyl)allyl)-4,5,7,8-tetrahydro-6H-thiazolo[5,4-d]azepine Prepared from 3,5-dimethoxy-cinnamyl chloride and 2 equivalents of 2-amino-4,5,7,8-tetrahydro-6H-thiazolo[5,4-d]azepine in chloroform. Yield 21% of theory, Melting point: 114°-19° C. (petroleum ether).

| Calculated: | C 62.58 | H 6.71 | N 12.16 |
|---|---|---|---|
| Found: | 62.57 | 6.57 | 11.95 |

4s) 2-Amino-6-(3-(4-dimethylamino-phenyl)allyl)-4,4,7,8-tetrahydro-6H-thiazolo[5,4-d]azepine Prepared from 4-dimethylamino-cinnamyl chloride hydrochloride and 3 equivalents of 2-amino-4,5,7,8-tetrahydro-6H-thiazolo[5,4-d]azepine in pure chloroform for one hour at 50° C. Yield: 2.4% of theory, Melting point: 85°-90° C. Molecular peak (m/z) Calculated: 328 Found: 328

4t) 2-Amino-6-(3-(1-naphthyl)allyl)-4,5,7,8-tetrahydro-6H-thiazolo[5,4-d]azepine Prepared from 3-(1-naphthyl)allyl chloride and 2 equivalents of 2-amino-4,5,7,8-tetrahydro-6H- thiazolo[5,4-d]azepine in chloroform for 3 days at 20° C. Yield: 31% of theory, Melting point: 178°-180° C. (chloroform/methanol =100:1).

| Calculated: | C 71.62 | H 6.31 | N 12.53 |
|---|---|---|---|
| Found: | 71.33 | 6.28 | 12.32 |

4u) 2-Amino-6-(3-(2-naphthyl)allyl)-4,5,7,8-tetrahydro-6H-thiazolo[5,4-d]azepine Prepared from 3-(2-naphthyl)allyl chloride and 2 equivalents of 2-amino-4,5,7,8-tetrahydro-6H- thiazolo[5,4-d]azepine in chloroform for 3 days at 20° C. Yield: 20% of theory, Melting point: 164°-165° C. (chloroform).

| Calculated: | C 71.62 | H 6.31 | N 12.53 |
|---|---|---|---|
| Found: | 71.49 | 6.43 | 12.45 |

4v) 2-Amino-6-(3-(2-biphenyl)allyl)-4,5,7,8-tetrahydro-6H-thiazolo[5,4-d]azepine Prepared from 3-(2-biphenyl)allyl chloride and 2 equivalents of 2-amino-4,5,7,8-tetrahydro-6H- thiazolo[5,4-d]azepine in chloroform for 5 hours at 50° C. Yield: 57% of theory, Melting point: 154°-158° C. (ether).

| Calculated: | C 73.11 | H 6.41 | N 11.63 |
|---|---|---|---|
| Found: | 73.00 | 6.44 | 11.48 |

4w) 2-Amino-6-(3-(4-biphenyl)allyl)-4,5,7,8-tetrahydro-6H-thiazolo[5,4-d]azepine. 0.25 H₂O Prepared from 3-(4-biphenyl)allyl chloride and 2 equivalents of 2-amino-4,5,7,8-tetrahydro-6H- thiazolo[5,4-d]azepine in chloroform. Yield: 54% of theory, Melting point: 178°-180° C. (ether).

| Calculated: (× 0.25 H₂O) | C 72.19 | H 6.47 | N 11.48 |
|---|---|---|---|
| Found: | 72.11 | 6.12 | 11.33 |

4x) 2-Amino-6-(3-(2-benzyloxy-phenyl)allyl)-4,5,7,8-tetrahydro-6H-thiazolo[5,4-d]azepine Prepared from 2-benzyloxy-cinnamyl chloride and 2 equivalents of 2-amino-4,5,7,8-tetrahydro-6H- thiazolo[5,4-d]azepine in chloroform for 5 hours at 50° C. Yield: 36% of theory, Melting point: 103°-107° C. (ether).

| Calculated: | C 70.57 | H 6.44 | N 10.73 |
|---|---|---|---|
| Found: | 70.42 | 6.63 | 11.01 |

4y) 2-Amino-6-(3-(3-benzyloxy-phenyl)allyl)-4,5,7,8-tetrahydro-6H-thiazolo[5,4-d]azepine Prepared from 3-benzyloxy-cinnamyl chloride and 2 equivalents of 2-amino-4,5,7,8-tetrahydro-6H- thiazolo[5,4-d]azepine in chloroform for 5 hours at 50° C. Yield: 59% of theory, Melting point: 78°-80° C. (ether).

| Calculated: | C 70.57 | H 6.44 | N 10.73 |
|---|---|---|---|
| Found: | 70.45 | 6.54 | 10.72 |

4z) 2-Amino-6-(3-(4-benzyloxy-phenyl)allyl)-4,5,7,8-tetrahydro-6H-thiazolo[5,4-d]azepine Prepared from 4-benzyloxy-cinnamyl chloride and 2 equivalents of 2-amino-4,5,7,8-tetrahydro-6H-thiazolo[5,4-d]azepine in chloroform for one hour at 50° C. Yield: 13% of theory, Melting point: 135°-140° C. (ether).

| Calculated: | C 70.56 | H 6.44 | N 10.73 |
|---|---|---|---|
| Found: | 70.80 | 6.42 | 10.52 |

EXAMPLE 5

2-Amino-6-cinnamyl-4,5,7,8-tetrahydro-6H-thiazolo[5,4-d]azepine

To a solution of 0.50 g (2.2 mmol) of 1-cinnamyl-hexahydro-4H-azepin-4-one in 3.7 ml of glacial acetic acid are added, at ambient temperature, first of all 1 ml of a 33% hydrogen bromide/glacial acetic acid solution and then within 10 minutes a solution of 0.11 ml (2.2 mmol) of bromine in 0.65 ml of glacial acetic acid is added dropwise. After 1.5 hours stirring at ambient temperature the mixture is evaporated down in vacuo at 50° C. To the evaporation residue are added 5 ml of ethanol, the mixture is evaporated down in vacuo and the procedure is repeated. The evaporation residue (crude 5-bromo-1-cinnamy-hexahydro-4H-azepin-4-one hydrobromide) is dissolved in 15 ml of anhydrous ethanol, 0.167 g (2.2 mmol) of thiourea are added and the mixture is refluxed from 2 hours. A mixture is evaporated down in vacuo made alkaline with sodium hydroxide solution and extracted with chloroform. The chloroform extract dried over sodium sulphate and filtered is evaporated down in vacuo. The evaporation residue is purified by column chromatography on silica gel (chloroform/methanol/conc. ammonia=100:10:1). Yield 0.13 g (21% of theory), Melting point: 121°-124° C. (ether).

| Calculated: | C 67.35 | H 6.71 | N 14.73 |
|---|---|---|---|
| Found: | 67.20 | 6.69 | 14.50 |

The following compound was prepared analogously to Example 5:

5a) 2-Amino-6-(3-phenyl-2-propyn-1-yl)-4,5,7,8-tetrahydro-6H-thiazolo[5,4-d]azepine. 0.5 H₂O Prepared from 5-bromo-1-(3-phenyl-2-propyn-1-yl)-hexahydro-4H-azepin-4-one hydrobromide by reacting with thiourea in ethanol. Yield: 4% of theory, Melting point: 145°-148° C.

| Calculated: (× 0.5 H₂O) | C 65.74 | H 6.20 | N 14.38 |
|---|---|---|---|
| Found: | 65.72 | 5.96 | 14.50 |

EXAMPLE 6

2-Amino-6-cinnamyl-4,5,7,8-tetrahydro-6H-thiazolo-[5,4-d]azepine

At 80° C., a solution of 0.50 g (2.2 mmol) of 1-cinnamyl-hexahydro-4H-azepin-4-one in 1.5 ml of glacial acetic acid is added dropwise to 0.687 g (2.2 mmol) of formamidine dihydrobromide in 3 ml of glacial acetic acid and the mixture is then stirred for 2 hours at 100° C. It is evaporated down in vacuo, made strongly alkaline with sodium hydroxide solution and extracted with chloroform. The dried and filtered chloroform extract is evaporated down in vacuo. The evaporation residue is purified by column chromatography on silica gel (chloroform/methanol/conc. ammonia=100:10:1). After elution of a small quantity of the isomeric compound 2-amino-7-cinnamyl-4,5,7,8-tetrahydro-6H-thiazolo[5,4-c]azepine the title compound is eluted. Yield: 0.045 g (7% of theory), Melting point: 120°-124° C. (ether). Molecular peak (m/z): Calculated: 285 Found: 285

EXAMPLE 7

2-Amino-6-(3-(2-amino-4-thiazolyl)allyl)-4,5,7,8-tetrahydro-6H-thiazolo[5,4-d]azepine 0.81 ml (11.1 mmol) of thionyl chloride are added dropwise, with stirring, at ambient temperature, to 0.58 g (3.7 mmol) of 3-(2-amino-4-thiazolyl)allyl alcohol in 10 ml of chloroform and the resulting mixture is stirred for 1 hour. It is evaporated down in vacuo, the foamy evaporation residue is dried [crude 3-(2-amino-4-thiazolyl)allyl chloride-hydrochloride]at 20° C./0.1 torr and then dissolved in 10 ml of anhydrous dimethylformamide. A solution of 2.5 g (14.8 mmol) of 2-amino-4,5,7,8-tetrahydro-6H-thiazolo[5,4-d]azepine in 20 ml of dimethylformamide is immediately added dropwise to this solution under nitrogen. The resulting mixture is stirred for 1 5 hours at 50°-60° C., evaporated down in vacuo. residues of dimethylformamide are eliminated at 0.1 torr and the residue is purified directly by column chromatography on silica gel (chloroform/methanol/conc. ammonia=5:1:0.15). Yield: 0.40 g (35% of theory), Melting point: 186°-190° C. (acetone).

| Calculated: | C 50.81 | H 5.58 | N 22.79 |
|---|---|---|---|
| Found: | 50.61 | 5.67 | 22.60 |

The following compound was prepared analogously to Example 7:

7a) 2-Amino-6-(3-(1-isoquinolinyl)allyl)-4,5,7,8-tetrahydro-6H-thiazolo[5,4-d]azepine. 0.25 H₂O Prepared from 3-(1-isoquinolinyl)-allyl chloride-hydrochloride and 3 equivalents of 2-amino-4,5,7,8-tetrahydro-6H-thiazolo[5,4-d]azepine in chloroform. Yield: 20% of theory, Melting point: 156°-157° C. (ether)

| Calculated: (× 0.25 H₂O) | C 66.93 | H 6.06 | N 16.44 |
|---|---|---|---|
| Found: | 66.82 | 6.02 | 16.29 |

EXAMPLE 8

2-Amino-6-(3-(2-furyl)allyl)-4,5,7,8-tetrahydro-6H-thiazolo[5,4-d]azepine 0.73 ml (10 mmol) of thionyl chloride are added dropwise at −5° C. to a stirred solution of 1.25 g (10 mmol) of 3-(2-furyl)allyl alcohol in 25 ml of anhydrous ether. The mixture is stirred for 15 minutes at −5° C., then evaporated down in vacuo at a bath temperature of 0° to 5° C., the evaporation residue (crude 3-(2-furyl)allyl chloride) is immediately dissolved in cold (−5° C.) chloroform, 3.08 g (10 mmol) of 2-amino-4,5,7,8-tetrahydro-6H-thiazolo-[5,4-d]azepine are added and the resulting mixture is stirred for one hour at 50° C. It is extracted with water, dried and the chloroform solution is filtered and evaporated down in vacuo. The evaporation residue is purified by column chromatography on silica gel (chloroform/methanol=10:1). Yield: 0.38 g (13.8% of theory), Melting point: 112°-119° C. (ether).

| Calculated: | C 61.06 | H 6.22 | N 15.26 |
|---|---|---|---|
| Found: | 60.89 | 6.17 | 14.92 |

The following compounds were prepared analogously to Example 8:

8a) 2-Amino-6-(3-(4-chloro-phenyl)allyl)-4,5,7,8-tetrahydro-6H-thiazolo[5,4-d]azepine Prepared from 4-chloro-cinnamyl chloride and 1 equivalent of 2-amino-4,5,7,8-tetrahydro-6H- thiazolo[5,4-d]azepine in chloroform. Yield: 26% of theory, Melting point: 148°-153° C. (ether).

| Calculated: | C 60.08 | H 5.67 | N 13.14 |
|---|---|---|---|
| Found: | 59.89 | 5.51 | 12.93 |

8b) 2-Amino-6-(3-(2-fluoro-phenyl)allyl)-4,5,7,8-tetrahydro-6H-thiazolo[5,4-d]azepine Prepared from 2-fluoro-cinnamyl chloride and 2 equivalents of 2-amino-4,5,7,8-tetrahydro-6H-thiazolo[5,4-d]azepine in chloroform. Yield: 36% of theory, Melting point: 96°-102° C. (ether).

| Calculated: | C 63.34 | H 5.98 | N 13.85 |
|---|---|---|---|
| Found: | 63.25 | 6.03 | 13.73 |

8c) 2-Amino-6-(3-(3-fluoro-phenyl)allyl)-4,5,7,8-tetrahydro-6H-thiazolo[5,4-d]azepine Prepared from 3-fluoro-cinnamyl chloride and 2 equivalents of 2-amino-4,5,7,8-tetrahydro-6H-thiazolo[5,4-d]azepine in chloroform. Yield: 44% of theory, Melting point: 128°-132° C. (ether).

| Calculated: | C 63.34 | H 5.98 | N 13.85 |
|---|---|---|---|
| Found: | 63.43 | 6.12 | 13.60 |

8d) 2-Amino-6-(3-(4-fluoro-phenyl)allyl)-4,5,7,8-tetrahydro-6H-thiazolo[5,4-d]azepine Prepared from 4-fluoro-cinnamyl chloride and 2 equivalents of 2-amino-4,5,7,8-tetrahydro-6H-thiazolo[5,4-d]azepine in chloroform. Yield: 13% of theory, Melting point: 142°-146° C.

| Calculated: | C 63.34 | H 5.98 | N 13.85 |
|---|---|---|---|
| Found: | 63.25 | 5.97 | 13.70 |

8e) 2-Amino-6-(3-(2-methoxy-phenyl)allyl)-4,5,7,8-tetrahydro-6H-thiazolo[5,4-d]azepine Prepared from 2-methoxy-cinnamyl chloride and 2 equivalents of 2-amino-4,5,7,8-tetrahydro-6H-thiazolo[5,4-d]azepine in chloroform. Yield: 13% of theory, Melting point: 80°-84° C.

| Calculated: | C 64.73 | H 6.71 | N 13.32 |
|---|---|---|---|
| Found: | 64.57 | 6.82 | 13.14 |

8f) 2-Amino-6-(3-(3-methoxy-phenyl)allyl)-4,5,7,8-tetrahydro-6H-thiazolo[5,4-d]azepine Prepared from 3-methoxy-cinnamyl chloride and 2 equivalents of 2-amino-4,5,7,8-tetrahydro-6H-thiazolo[5,4-d]azepine in chloroform. -Yield: 21% of theory, Melting point: 120°-124° C.

| Calculated: | C 64.73 | H 6.71 | N 13.32 |
|---|---|---|---|
| Found: | 64.80 | 6.48 | 13.15 |

8g) 2-Amino-6-(3-(4-methylthio-phenyl)allyl)-4,5,7,8-tetrahydro-6H-thiazolo[5,4-d]azepine. 0.25 H$_2$O Prepared from 4-methylthio-cinnamyl chloride and 2 equivalents of 2-amino-4,5,7,8-tetrahydro-6H- thiazolo[5,4-d]azepine in chloroform. Yield: 31% of theory, Melting point: 152°-157° C.

| Calculated: (× 0.25 H$_2$O) | C 60.74 | H 6.45 | N 12.51 |
|---|---|---|---|
| Found: | 60.53 | 6.23 | 12.36 |

8h) 2-Amino-6-(3-(4-methylsulphinyl-phenyl)allyl)-4,5,7,8-tetrahydro-6H-thiazolo[5,4-d]azepine-hydrate Prepared from 4-methylsulphinyl-cinnamyl chloride and 2 equivalents of 2-amino-4,5,7,8-tetrahydro-6H-thiazolo[5,4-d]azepine in chloroform. Yield: 48% of theory, Melting point: 171°-176° C. (ether).

| Calculated: | C 55.88 | H 6.34 | N 11.50 |
|---|---|---|---|
| Found: | 56.07 | 6.32 | 11.43 |

8i) 2-Amino-6-(3-(4-methylsulphonyl-phenyl)allyl)-4,5,7,8-tetrahydro-6H-thiazolo[5,4-d]azepine Prepared from 4-methylsulphonyl-cinnamyl chloride and 2 equivalents of 2-amino-4,5,7,8-tetrahydro-6H-thiazolo[5,4-d]azepine in chloroform. Yield: 21% of theory, Melting point: 157°-161° C. (ether).

| Calculated: | C 56.17 | H 5.82 | N 11.56 |
|---|---|---|---|
| Found: | 56.27 | 5.73 | 11.48 |

8k) 2-Amino-6-(4-phenyl-3-buten-1-yl)-4,5,7,8-tetrahydro-6H-thiazolo[5,4-d]azepine Prepared analogously to Example 8 from 4-phenyl-3-buten-1-yl-bromide [boiling point 93° C./1,5 torr; prepared from 1-cyclopropyl-1-phenyl-carbinol with phosphorous tribromide] with 4 equivalents of 2-amino-4,5,7,8-tetrahydro-6H-thiazolo[5,4-d]azepine in pure chloroform during 8 hours at 60° C. Yield: 39% of theory, Melting point: 157°-158° C. (chloroform/toluene)

| Calculated: | C 68.19 | H 7.07 | N 14.03 |
|---|---|---|---|
| Found: | 68.06 | 7.09 | 14.01 |

8l) 2-Amino-6-(3-(2,6-dimethoxy-phenyl)allyl)-4,5,7,8-tetrahydro-6H-thiazolo[5,4-d]azepine ×0,5 H$_2$O Prepared from 2,6-dimethoxy-cinnamyl chloride and 2 equivalents of 2-amino-4,5,7,8-tetrahydro-6H-thiazolo[5,4-d]azepine in chloroform. Yield: 10% of theory, Melting point: 100°-102° C. (ether)

| Calculated: (× 0,5 H$_2$O) | C 60.99 | H 6.82 | N 11.85 |
|---|---|---|---|

| | | | |
|---|---|---|---|
| -continued | | | |
| Found: | 60.95 | 6.75 | 11.91 |

8m) 2-Amino-6-(3-(3,4,5-trimethoxy-phenyl)allyl)-4,5,7,8-tetrahydro-6H-thiazolo[5,4-d]azepine-hydrate Prepared from 3,4,5-trimethoxy-cinnamyl chloride and 2 equivalents of 2-amino-4,5,7,8-tetrahydro-6H-thiazolo[5,4-d]azepine in chloroform. Yield: 17% of theory, Melting point: 70°-73° C. (decomp.)

| | | | |
|---|---|---|---|
| Calculated: ($\times$ 1 H$_2$O) | C 57.99 | H 6.99 | N 10.68 |
| Found: | 58.15 | 6.86 | 10.49 |

8n) 2-Amino-6-(3-(4-isobutoxy-phenyl)allyl)-4,5,7,8-tetrahydro-6H-thiazolo[5,4-d]azepine Prepared from 4-isobutoxy-cinnamyl chloride and 2 equivalents of 2-amino-4,5,7,8-tetrahydro-6H- thiazolo[5,4-d]azepine in chloroform. Yield: 6% of theory, Melting point: 110°-113° C. (ether).

| | | | |
|---|---|---|---|
| Calculated: | C 67.20 | H 7.61 | N 11.76 |
| Found: | 67.01 | 7.71 | 11.50 |

8o) 2-Amino-6-(2,3-diphenyl)allyl)-4,5,7,8-tetrahydro-6H-thiazolo[5,4-d]azepine Prepared from 2,3-diphenylallyl chloride and 2 equivalents of 2-amino-4,5,7,8-tetrahydro-6H-thiazolo[5,4-d]azepine in chloroform. Yield: 19% of theory, Melting point: 112°-115° C. (petroleum ether).

| | | | |
|---|---|---|---|
| Calculated: | C 73.11 | H 6.41 | N 11.63 |
| Found: | 72.92 | 6.50 | 11.57 |

EXAMPLE 9

2-Amino-6-(3-(2-methyl-4-thiazolyl)allyl)-4,5,7,8,-tetrahydro-6H-thiazolo[5,4-d]azepine-semihydrate 2.9 ml (40 mmol) of thionyl chloride are added dropwise, at 5° to 10° C., under nitrogen, to a stirred solution of 3.1 g (20 mmol) of 3-(2-methyl-4-thiazolyl)allyl alcohol in 120 ml of anhydrous ether, whereupon a colourless precipitate forms. The mixture is stirred for 10 minutes and then evaporated in vacuo at 20° C. The evaporation residue (crude 3-(2-methyl-4-thiazolyl)allyl chloride-hydrochloride) is dissolved in 20 ml of chloroform and immediately combined with a solution of 0.1 g (60 mmol) of 2-amino-4,5,7,8-tetrahydro-6H-thiazolo[5,4-d]azepine in 150 ml of chloroform. 2.76 g (20 mmol) of potassium carbonate are added and the mixture is stirred for 3 hours at 80°-90° C. with gentle refluxing. 50 ml of chloroform are added, the mixture is cooled to ambient temperature and extracted three times with water. The dried and filtered chloroform solution is evaporated down in vacuo. The evaporation residue is purified by column chromatography on silica gel (chloroform/methanol=5:1). Yield: 2.80 g (45% of theory), Melting point: 182°-185° C.

| | | | |
|---|---|---|---|
| Calculated: ($\times$ 0.5 H$_2$O) | C 53.32 | H 6.07 | N 17.77 |
| Found: | 53.48 | 5.86 | 17.79 |

The following compounds were prepared analogously to Example 9:

9a) 2-Amino-6-(3-phenyl-2-buten-1-yl)-4,5,7,8-tetrahydro-6H-thiazolo[5,4-d]azepine. 0.25 H$_2$O Prepared from 3-phenyl-2-buten-1-yl chloride and 1 equivalent of 2-amino-4,5,7,8-tetrahydro-6H- thiazolo[5,4-d]azepine in anhydrous dimethylformamide in the presence of 1 equivalent of potassium carbonate for 12 hours at ambient temperature. Yield: 34% of theory, Melting point: 131°-135° C. (ether).

| | | | |
|---|---|---|---|
| Calculated: ($\times$ 0.25 H$_2$O) | C 67.18 | H 7.13 | N 13.83 |
| Found: | 67.35 | 7.12 | 13.75 |

9b) 2-Amino-6-(2-methyl-3-phenyl-2-propen-1-yl)-4,5,7,8-tetrahydro-6H-thiazolo[5,4-d]azepine Prepared from 2-methyl-3-phenyl-allyl chloride and 2 equivalents of 2-amino-4,5,7,8-tetrahydro-6H-thiazolo[5,4-d]azepine in chloroform for 2 hours at ambient temperature. Yield: 8% of theory, Melting point: 112°-115° C.

| | | | |
|---|---|---|---|
| Calculated: | C 68.21 | H 7.07 | N 14.04 |
| Found: | 68.03 | 7.17 | 14.27 |

EXAMPLE 10

2-Amino-6-(3-(2-pyridyl)-2-propyn-1-yl)-4,5,7,8-tetrahydro-6H-thiazolo[5,4-d]azepine 61 mg (0.32 mmol) of copper(I)iodide and 225 mg (0.32 mmol) of bis(triphenylphosphine)-palladium chloride are added to a mixture of 3.0 g (14.5 mmol) of 2-amino-6-propargyl-4,5,7,8-tetrahydro-6H-thiazolo[5,4-d]azepine (m.p. 157°-160° C., prepared from 2- amino-4,5,7,8-tetrahydro-6H-thiazolo[5,4-d]azepine with propargyl bromide in chloroform), 1.38 ml (14.5 mmol) of 2-bromo-pyridine and 100 ml of diethylamine, said mixture being stirred at ambient temperature under nitrogen, and the resulting mixture is stirred for 48 hours at ambient temperature. It is evaporated down in vacuo and the evaporation residue is distributed between chloroform and water. The dried and filtered chloroform extract is evaporated down in vacuo. The evaporation residue is purified by column chromatography on silica gel (chloroform/methanol=10:1). Yield: 2.7 g (65% of theory), Melting point: 165°-168° C. (acetone).

| | | | |
|---|---|---|---|
| Calculated: | C 63.37 | H 5.67 | N 19.71 |
| Found: | 63.20 | 5.50 | 20.00 |

The following compound was prepared analogously to Example 10:

10a) 2-Amino-6-(3-(3-pyridyl)-2-propyn-1-yl)-4,5,7,8-tetrahydro-6H-thiazolo[5,4-d]azepine-semihydrate Prepared from 2-amino-6-propargyl-4,5,7,8-tetrahydro-6H-thiazolo[5,4-d]azepine and 3-bromopyridine. Purification by column chromatography is carried out on silica gel (toluene/ethyl acetate/methanol 4:2:2). Yield: 37% of theory, Melting point: 118°-121° C. (ether).

| | | | |
|---|---|---|---|
| Calculated: ($\times$0.5 H$_2$O) | C 61.40 | H 5.84 | N 19.10 |
| Found: | 61.51 | 5.52 | 19.25 |

EXAMPLE 11

2-Amino-6-(3-(6-chloro-2-pyridyl)allyl)-4,5,7,8-tetrahydro-6H-thiazolo[5,4-d]azepine

To a stirred solution of 0 90 g (5.3 mmol) of 3-(6-chloro-2-pyridyl)allyl alcohol in 20 ml of anhydrous ether, there is slowly added dropwise, at ambient temperature, a solution of 0.38 ml (5.3 mmol) of thionyl chloride in 0.5 ml of anhydrous ether, whereupon a precipitate is formed. The mixture is stirred for 20 minutes and then evaporated down in vacuo at ambient temperature. The evaporation residue (crude 3-(6-chloro-2-pyridyl)allyl chloride hydrochloride) is dissolved in 10 ml of chloroform. This solution is added dropwise to a solution of 2.70 g (15.9 mmol) of 2-amino-4,5,7,8-tetrahydro-6H-thiazolo[5,4-d]azepine in 41 ml of chloroform, stirred at 50°-60° C. The resulting mixture is stirred for 5 hours at 50°-60° C., diluted with 200 ml of chloroform and extracted several times with water. The dried and filtered chloroform solution is evaporated down in vacuo. The evaporation residue is purified by column chromatography on silica gel (toluene/ethyl acetate/methanol =4:2:1). Yield: 1.1 g (64% of theory), Melting point: 161°-164° C. (ether).

| Calculated: | C 56.15 | H 5.34 | Cl 11.05 | N 17.46 |
|---|---|---|---|---|
| Found: | 56.28 | 5.41 | 10.99 | 17.43 |

The following compounds were prepared analogously to Example 11:

11a) 2-Amino-6-(3-(2-pyridyl)allyl)-4,5,7,8-tetrahydro-6H-thiazolo[5,4-d]azepine Prepared from 3-(2-pyridyl)allyl chloride hydrochloride and 3 equivalents of 2-amino-4,5,7,8-tetrahydro-6H-thiazolo[5,4-d]azepine in chloroform. Yield: 33% of theory, Melting point: 162°-165° C.

| Calculated: | C 62.92 | H 6.34 | N 19.57 |
|---|---|---|---|
| Found: | 63.16 | 6.35 | 19.36 |

| 200 MHz-$^1$H-NMR spectrum (d$^6$-DMSO/CD$_3$OD): | |
|---|---|
| δ = 3.39 ppm (doublet), | 2H (allylic CH$_2$) |
| δ = 6.65 ppm (doublet), | 1H (olefinic H) |
| δ = 6.74 ppm (triplet) and | |
| δ = 6.82 ppm (triplet), | 1H (olefinic H) |

By dissolving the base in methanol, adding 1 equivalent of 1N hydrochloric acid, evaporating down in vacuo and drying over phosphorus pentoxide at 60° C./20 torr, the 2-amino-6-(3-(2-pyridyl)allyl)- 4,5,7,8-tetrahydro-6H-thiazolo[5,4-d]azepine hydrochloride ×1.5 H$_2$O is obtained in an 84% yield melting in the range from 100°-120° C.

| Calculated: | (×1.5 H$_2$O) | C 51.50 | H 6.34 | N 16.02 |
|---|---|---|---|---|
| Found: | | 51.60 | 6.41 | 16.00 |

11b) 2-Amino-6-(3-(3-pyridyl)allyl)-4,5,7,8-tetrahydro-6H-thiazolo[5,4-d]azepine. 0.25 H$_2$O Prepared from 3-(3-pyridyl)allyl chloride hydrochloride and 3 equivalents of 2-amino-4,5,7,8-tetrahydro-6H-thiazolo[5,4-d]azepine in anhydrous dimethylformamide by stirring for two days at ambient temperature. Yield: 59% of theory, Melting point: 166°-169° C. (acetone)

| Calculated: | (×0.25 H$_2$O) | C 61.93 | H 6.41 | N 19.26 |
|---|---|---|---|---|
| Found: | | 61.97 | 6.35 | 19.51 |

| 200 MHz-$^1$H-NMR spectrum (d$^6$-DMSO/CD$_3$OD): | |
|---|---|
| δ = 3.38 ppm (doublet), | 2H (allylic CH$_2$) |
| δ = 6.43 ppm (triplet) and | |
| δ = 6.50 ppm (triplet), | 1H (olefinic H) |
| δ = 6.62 ppm (doublet), | 1H (olefinic H) |

11c) 2-Amino-6-(3-(4-pyridyl)allyl)-4,5,7,8-tetrahydro-6H-thiazolo[5,4-d]azepine. 0.4 H$_2$O Prepared from 3-(4-pyridyl)allyl chloride hydrochloride and 3 equivalents of 2-amino-4,5,7,8-tetrahydro-6H-thiazolo[5,4-d]azepine in chloroform. Yield: 28% of theory, Melting point: 210°-215° C. (ether).

| Calculated: | (×0.4 H$_2$O) | C 61.36 | H 6.45 | N 19.08 |
|---|---|---|---|---|
| Found: | | 61.14 | 6.28 | 19.07 |

11d) 2-Amino-6-(3-(3-pyridyl)propyl)-4,5,7,8-tetrahydro-6H-thiazolo[5,4-d]azepine Prepared from 3-(3-pyridyl)propyl chloride hydrochloride and 1 equivalent of 2-amino-4,5,7,8-tetrahydro-6H-thiazolo[5,4-d]azepine in anhydrous dimethylformamide in the presence of two equivalents of potassium carbonate for 1.5 hours at 80° C. Yield: 8% of theory, Melting point: 90°-92° C. (ether). Molecular peak (m/z) Calculated: 288 Found: 288

11e) 2-Amino-6-(3-(4-amino-3,5-dibromo-phenyl)allyl)-4,5,7,8-tetrahydro-6H-thiazolo[5,4-d]azepine Prepared from 4-amino-4,5-dibromo-cinnamyl chloride hydrochloride (from 4-amino-3,5-dibromo-cinnamyl alcohol with 1.2 equivalents of thionyl chloride in chloroform) and 2 equivalents of 2-amino-4,5,7,8-tetrahydro-6H-thiazolo[5,4-d]azepine in chloroform. Yield: 12% of theory, Melting point: 198°-199° C.

| Calculated: | C 41.94 | H 3.96 | N 12.23 |
|---|---|---|---|
| Found: | 41.80 | 3.99 | 12.17 |

11f) 2-Amino-6-(3-(4-amino-3,5-dichloro-phenyl)allyl)-4,5,7,8-tetrahydro-6H-thiazolo[5,4-d]azepine. 0.5 H$_2$O Prepared from 4-amino-3,5-dichloro-cinnamyl chloride hydrochloride (from 4-amino-3,5-dichloro- cinnamyl alcohol with 1.2 equivalents of thionyl chloride in chloroform) and 2 equivalents of 2-amino-4,5,7,8-tetrahydro-6H-thiazolo[5,4-d]azepine in chloroform. Yield: 7% of theory, Melting point: 163°-165° C.

| Calculated: | (×0.5 H$_2$O) | C 50.79 | H 5.06 | N 18.74 |
|---|---|---|---|---|
| Found: | | 50.98 | 5.17 | 18.80 |

11g) 2-Amino-6-(3-(4-hydroxy-phenyl)allyl)-4,5,7,8-tetrahydro-6H-thiazolo[5,4-d]azepine. 0.6 H$_2$O Prepared from 3-(4-hydroxy-phenyl)allyl chloride and 2 equivalents of 2-amino-4,5,7,8-tetrahydro-6H-thiazolo[5,4-d]azepine in chloroform. Yield: 1% of theory, Melting point: 153°-161° C. (ether); sintering at 105° C.

| Calculated: | (×0.6 H$_2$O) | C 61.55 | H 6.52 | N 13.49 |
|---|---|---|---|---|
| Found: | | 61.50 | 6.40 | 13.08 |

11h) 2-Amino-6-(3-4-chlorophenyl)propyl-4,5,7,8-tetrahydro-6H-thiazolo[5,4-d]azepine Prepared from 3-(4-chlorophenyl)propyl bromide and 2 equivalents of 2-amino-4,5,7,8-tetrahydro-6H-thiazolo[5,4-d]azepine in anhydrous dimethylformamide. Yield: 37% of theory, Melting point: 153° C.

| Calculated: | C 59.71 | H 6.26 | N 13.05 |
|---|---|---|---|
| Found: | 59.53 | 6.06 | 13.21 |

11i) 2-Amino-6-(3-(3-methyl-2-pyridyl)allyl)-4,5,7,8-tetrahydro-6H-thiazolo[5,4-d]azepine Prepared from 3-(3-methyl-2-pyridyl)allyl chloride hydrochloride and 3 equivalents of 2-amino-4,5,7,8-tetrahydro-6H-thiazolo[5,4-d]azepine in chloroform. Yield: 45% of theory, Melting point: 188°-190° C. (ether).

| Calculated: | C 63.98 | H 6.71 | N 18.65 |
|---|---|---|---|
| Found: | 63.87 | 6.59 | 18.62 |

11k) 2-Amino-6-(3-(5-methyl-2-pyridyl)allyl)-4,5,7,8-tetrahydro-6H-thiazolo[5,4-d]azepine Prepared from 3-(5-methyl-2-pyridyl)allyl chloride hydrochloride and 3 equivalents of 2-amino-4,5,7,8-tetrahydro-6H-thiazolo[5,4-d]azepine in chloroform. Yield: 22% of theory, Melting point: 172°-175° C. (isopropanol).

| Calculated: | C 63.98 | H 6.71 | N 18.65 |
|---|---|---|---|
| Found: | 63.82 | 6.59 | 18.61 |

11l) 2-Amino-6-(3-(6-methyl-2-pyridyl)ally)-4,5,7,8-tetrahydro-6H-thiazolo[5,4-d]azepine 0.5 H₂O Prepared from 3-(6-methyl-2-pyridyl)allyl chloride hydrochloride and 3 equivalents of 2-amino-4,5,7,8-tetrahydro-6H-thiazolo[5,4-d]azepine in chloroform. Yield: 21% of theory, Melting point: 122°-125° C. (petroleum ether).

| Calculated: | (×0.5 H₂O) | C 62.10 | H 6.84 | N 18.11 |
|---|---|---|---|---|
| Found: | | 62.13 | 6.80 | 17.98 |

11m) 2-Amino-6-(3-(6-methyl-3-pyridyl)allyl)-4,5,7,8-tetrahydro-6H-thiazolo[5,4-d]azepine Prepared from 3-(6-methyl-3-pyridyl)allyl chloride hydrochloride and 3 equivalents of 2-amino-4,5,7,8-tetrahydro-6H-thiazolo[5,4-d]azepine in chloroform. Yield: 30% of theory, Melting point: 180°-184° C. (ether).

| Calculated: | C 63.98 | H 6.71 | N 18.65 |
|---|---|---|---|
| Found: | 63.79 | 6.72 | 18.44 |

11n) 2-Amino-6-tetrahydro-6H-thiazolo[5,4-d]azepine

Prepared from 2-ethyl-1-chloro-3-phenyl-2-propene and 2 equivalents of 2-amino-4,5,7,8-tetrahydro-6H-thiazolo[5,4-d]azepine in chloroform. Yield: 22% of theory, Melting point: 110°-113° C. (petroleum ether).

| Calculated: | C 68.98 | H 7.40 | N 13.41 |
|---|---|---|---|
| Found: | 68.68 | 7.27 | 13.55 |

11o) 2-Amino-6-(3-phenyl-2-n-propyl-2-propen-1-yl)-4,5,7,8-tetrahydro-6H-thiazolo[5,4-d]azepine Prepared from 1-chloro-3-phenyl-2-n-propyl-2-propene and 2 equivalents of 2-amino-4,5,7,8-tetrahydro-6H-triazolo[5,4-d]azepine in chloroform. Yield: 15% of theory, Melting point: 77°-80° C. (petroleum ether).

| Calculated: | C 69.70 | H 7.70 | N 12.83 |
|---|---|---|---|
| Found: | 69.64 | 7.57 | 12.66 |

11p) 2-Amino-6-(3-(2-(1-piperidino)phenyl)-2-propen-1-yl)-4,5,7,8-tetrahydro-6H-thiazolo[5,4-d]azepine Prepared from 2-(1-piperidino)-cinnamyl chloride hydrochloride and 3 equivalents of 2-amino-4,5,7,8-tetrahydro-6H-thiazolo[5,4-d]azepine in chloroform for 5 hours at 50° C. In the purification by column chromatography on silica (toluene/ethyl acetate/methanol =4:2:1) first the isomeric compound 2-amino-6-(1-(2-(1-piperidino)phenyl)-2-propen-1-yl)-4,5,7,8-tetrahydro-6H- thiazolo[5,4-d]azepine is eluted (7% of theory; melting point 85°-95° C. (ether)). The title compound is then eluted. Yield: 6% of theory, melting point: 113°-115° C. (ether).

| Calculated: | C 68.45 | H 7.66 | N 15.20 |
|---|---|---|---|
| Found: | 68.36 | 7.96 | 15.15 |

EXAMPLE 12

(Z)-2-Amino-6-(3-(2-pyridyl)-2-propen-1-yl)-4,5,7,8-tetrahydro-6H-thiazolo[5,4-d]azepine. 0.25 H₂O 1.5 g (5.3 mmol) of 2-amino-6-(3-(2-pyridyl)-2-propyn-1-yl)-4,5,7,8-tetrahydro-6H- thiazolo[5,4-d]azepine is hydrogenated in 75 ml of absolute ethanol under a hydrogen pressure of 1 bar using 0.75 g of palladium/barium sulphate (5%) for 2 hours at ambient temperature. The catalyst is removed by filtering and the residue is evaporated down in vacuo. The evaporation residue is purified by column chromatography on silica gel (chloroform/methanol =3:1). Yield: 0.47 g (31% of theory), Melting point: 156°-158° C. (acetone).

| Calculated: | (×0.25 H₂O) | C 61.95 | H 6.41 | N 19.27 |
|---|---|---|---|---|
| Found: | | 61.93 | 6.21 | 19.16 |

| 200 MHz-¹H-NMR spectrum (CDCl₃): | |
|---|---|
| δ = 3.85 ppm (doublet), | 2H (allylic CH2) |
| δ = 6.03 ppm (triplet and | |
| δ = 6.08 ppm (triplet), J = 12 Hz | 1H (olefinic H) |
| δ = 6.58 ppm (doublet), | 1H (olefinic H) |

The following compounds were prepared analogously to Example 12

12a) (Z)-2-Amino-6-(3-(3-pyridyl)-2-propen-1-yl)-4,5,7,8-tetrahydro-6H-thiazolo[5,4-d]azepine Prepared by catalytic hydrogenation of 2-amino-6-(3-(3-pyridyl)-2-propyn-1-yl)-4,5,7,8-tetrahydro-6H-thiazolo[5,4-d]azepine with palladium/barium sulphate (5%) in ethanol. Yield: 42% of theory, Melting point: 125°-126° C. (acetone).

| Calculated: | C 62.92 | H 6.34 | N 19.57 |
|---|---|---|---|

-continued

| Found: | 62.89 | 6.53 | 19.32 |
|---|---|---|---|

200 MHz-$^1$H-NMR spectrum (CDCl$_3$):

δ = 3.50 ppm (doublet), 2H (allylic CH2)
δ = 6.00 ppm (triplet) and
δ = 6.06 ppm (triplet), J = 12 Hz 1H (olefinic H)
δ = 6.60 ppm (doublet), 1H (olefinic H)

12b) (Z)-2-Amino-6-(3-phenyl TM 2-propen-1-yl)-4,5,7,8-tetrahydro-6H-thiazolo[5,4-d]azepine Prepared by catalytic hydrogenation of 2-amino-6-(3-(3-phenyl-2-propyn-1-yl)-4,5,7,8-tetrahydro-6H-thiazolo[5,4-d]azepine with palladium/barium sulphate (5%) in ethanol. Yield: 43% of theory, Melting point: 140°-142° C. (acetone).

| Calculated: | C 67.35 | H 6.75 | N 14.73 |
|---|---|---|---|
| Found: | 67.33 | 6.89 | 14.89 |

200 MHz-$^1$H-NMR spectrum (CDCl$_3$):

δ = 3.50 ppm (doublet), 2H (allylic CH2)
δ = 5.81 ppm (triplet) and
δ = 5.86 ppm (triplet), 1H (olefinic H)
δ = 6.60 ppm (doublet), 1H (olefinic H)

A small amount (<2%) of the (E)-isomer can be detected by δ=3.40 ppm (doublet; allylic CH2).

EXAMPLE 13

2-Amino-6-(3-(3-pyridyl)propyl)-4,5,7,8-tetrahydro-6H-thiazolo[5,4-d]azepine 2.0 g (7 mmol) of 2-amino-6-(3-(3-pyridyl)allyl)-4,5,7,8-tetrahydro-6H-thiazolo[5,4-d]azepine are hydrogenated with 1 g of palladium/charcoal (10%) at ambient temperature under 1 bar of hydrogen in 45 ml of ethanol. A further 1 g or 0.5 g of catalyst are added after 2 and 3 hours, respectively, of hydrogenation. After a total hydrogenation time of 4.5 hours the catalyst is removed by filtering and the filtrate is evaporated down in vacuo. It is distributed between chloroform and water, the dried and filtered chloroform solution is evaporated down in vacuo and the evaporation residue is purified by column chromatography on silica gel (chloroform/methanol=1:1). Yield: 0.44 g (22% of theory), Melting point: 90°-92° C. (ether).

| Calculated: | C 62.48 | H 6.99 | N 19.43 |
|---|---|---|---|
| Found: | 62.31 | 7.01 | 19.55 |

The following compound was prepared analogously to Example 13:

13a) 2-Amino-6-(3-(2-pyridyl)propyl)-4,5,7,8-tetrahydro-6H-thiazolo[5,4-d]azepine. 0.5 H$_2$O Prepared by catalytic hydrogenation of 2-amino-6-(3-(2-pyridyl)allyl)-4,5,7,8-tetrahydro-6H-triazolo[5,4-d]azepine on palladium/charcoal (10%) at ambient temperature. Yield: 15% of theory,
Melting point: 122°-125° C. (ether).

| | C | H | N |
|---|---|---|---|
| Calculated: (×0.5 H$_2$O) | 60.59 | 7.12 | 18.85 |
| Found: | 60.72 | 7.22 | 19.06 |

EXAMPLE 14

2-Amino-6-(3-phenyl-2-propyn-1-yl)-4,5,7,8-tetrahydro-6H-thiazolo[5,4-d]azepine

To a stirred solution of 5.8 g (34.5 mmol) of 2-amino-4,5,7,8-tetrahydro-6H-thiazolo[5,4-d]azepine and 2.0 ml (34.5 mmol) of glacial acetic acid in 50 ml of pure methanol, there is added dropwise at 0° C. a solution of 4.5 g (34.5 mmol) of 3-phenyl-propargyl aldehyde in 180 ml of pure methanol. Then 2.17 g (34.5 mmol) of sodium cyanoborohydride are added at 0° C. and the mixture is stirred for 1.5 hours whilst cooling with ice. It is evaporated down in vacuo, water is added and it is then made acidic with concentrated hydrochloric acid. It is then alkalised by the addition of solid sodium bicarbonate and extracted several times with chloroform. The chloroform solution is dried and filtered and evaporated down in vacuo. The evaporation residue is purified by column chromatography on silica gel (chloroform/methanol/conc. ammonia 100:10:0.5). Yield: 3.4 g (35% of theory), Melting point: 155°-159° C. (acetone).

| | C | H | N |
|---|---|---|---|
| Calculated: | 67.83 | 6.05 | 14.83 |
| Found: | 67.69 | 6.12 | 14.69 |

The following compounds were prepared analogously to Example 14:

14a) 2-Amino-6-(3-(3-pyridyl)allyl)-4,5,7,8-tetrahydro-6H-thiazolo[5,4-d]azepine Prepared from 3-(3-pyridyl)acrolein and 2-amino-4,5,7,8-tetrahydro-6H-thiazolo[5,4-d]azepine by reductive amination with sodium cyanoborohydride. Yield: 40% of theory, Melting point: 162°-165° C.

| | C | H | N |
|---|---|---|---|
| Calculated: | 62.92 | 6.34 | 19.57 |
| Found: | 63.72 | 6.32 | 19.42 |
| Molecular peak (m/z): Calculated: 286 Found: 286 | | | |

14b) 2-Amino-6-(3-(4-cyano-phenyl)allyl)-4,5,7,8-tetrahydro-6H-thiazolo[5,4-d]azepine Prepared from 3-(4-cyano-phenyl)acrolein and 2-amino-4,5,7,8-tetrahydro-6H-thiazolo[5,4-d]azepine by reductive amination with sodium cyanoborohydride. Yield: 8% of theory, Melting point: 199°-205° C. (decomp).

| | C | H | N |
|---|---|---|---|
| Calculated: | 65.79 | 5.85 | 18.05 |
| Found: | 65.59 | 6.00 | 17.88 |
| Molecular peak (m/z): Calculated: 286 Found: 286 | | | |

14c) 2-Amino-6-(3-(3-indolyl)allyl)-4,5,7,8-tetrahydro-6H-thiazolo[5,4-d]azepine Prepared from 3-(3-indolyl)acrolein and 1 equivalent of 2-amino-4,5,7,8-tetrahydro-6H- thiazolo[5,4-d]azepine by reductive amination with 0.9 equivalents of sodium cyanoborohydride. Purification of the crude product by column chromatography is carried out using neutral aluminium oxide of activity stage I (toluene/ethyl acetate/ethanol=4:1:0.5). Yield: 11% of theory, Melting point: 155°-160° C.

|             | C     | H    | N     |
|-------------|-------|------|-------|
| Calculated: | 66.65 | 6.21 | 17.27 |
| Found:      | 66.32 | 6.34 | 17.00 |
| Molecular peak (m/z): Calculated: 324 Found: 324 | | | |

14d) 2-Amino-6-(3-(3-quinolinyl)allyl)-4,5,7,8-tetrahydro-6H-thiazolo[5,4-d]azepine. 0.3 $H_2O$ Prepared from 3-(3-quinolinyl)acrolein and 2-amino-4,5,7,8-tetrahydro-6H-thiazolo[5,4-d]azepine by reductive amination with sodium cyanoborohydride. Yield: 18% of theory, Melting point: 172°–177° C. (acetone).

|                              | C     | H    | N     |
|------------------------------|-------|------|-------|
| Calculated: (×0.3 $H_2O$)    | 66.75 | 6.07 | 16.39 |
| Found:                       | 66.73 | 5.96 | 16.52 |

14e) 2-Amino-6-(3-(4-isoquinolinyl)-3-methoxy-1-propyl)-4,5,7,8-tetrahydro-6H-thiazolo[5,4-d]azepine (A) and 2-Amino-6-(3-(4-isoquinolinyl)allyl)-4,5,7,8-tetrahydro-6H-thiazolo[5,4-d]azepine. 0.25 H2O (B)

Prepared from 3-(4-isoquinolinyl)acrolein and 2-amino-4,5,7,8-tetrahydro-6H-thiazolo[5,4-d]azepine by reductive amination with sodium cyanoborohydride (in methanol in the presence of I equivalent of glacial acetic acid). The crude product is purified by column chromatography on silica gel (acetone/methanol/conc. ammonia =50:12:0.5). At first the title compound (A) is eluted. Yield: 4% of theory, Melting point: 205°–208° C. (ether).

|             | C     | H    | N     |
|-------------|-------|------|-------|
| Calculated: | 65.20 | 6.57 | 15.21 |
| Found:      | 65.32 | 6.63 | 15.00 |
| Molecular peak (m/z): Calculated: 368 Found: 368 | | | |

Then the title compound (B) is eluted. Yield: 6.4% of theory, Melting point: 210°–215° C. (acetone); sintering at 205° C.

|                              | C     | H    | N     |
|------------------------------|-------|------|-------|
| Calculated: (×0.25 $H_2O$)   | 66.92 | 6.06 | 16.43 |
| Found:                       | 66.79 | 6.05 | 16.36 |
| Molecular peak (m/z): Calculated: 336 Found: 336 | | | |

EXAMPLE 15

2-Amino-6-(3-(2-hydroxy-phenyl)allyl)-4,5,7,8-tetrahydro-6H-thiazolo[5,4-d]azepine. 0.5 $H_2O$ 0.75 g (1.9 mmol) of 2-amino-6-(3-(2-benzyloxy-phenyl)allyl)-4,5,7,8-tetrahydro-6H- thiazolo[5,4-d]azepine are stirred in 30 ml of pure methylene chloride at an internal temperature of -25° C. and at this temperature 3.8 ml (3.8 mmol) of a 1M boron tribromide solution in methylene chloride is slowly added dropwise, whereupon a precipitate is formed. After 65 minutes, no more starting compound can be detected by thin layer chromatographic analysis. Water is added, followed by 10 ml of semi-concentrated hydrochloric acid. After separation of the phases, the acidic aqueous phase is neutralised with solid sodium bicarbonate. It is extracted several times with chloroform, with the addition of a little (about 1%) methanol. The dried and filtered chloroform phase is evaporated down in vacuo. The evaporation residue is purified by column chromatography on silica gel (chloroform/methanol/conc. ammonia=50:10:0.5). Yield: 0.30 g (52% of theory), Melting point: 50° C. (ether); foamy.

|                              | C     | H    | N     |
|------------------------------|-------|------|-------|
| Calculated: (×0.5 $H_2O$)    | 61.93 | 6.50 | 13.54 |
| Found:                       | 61.98 | 6.58 | 13.45 |

The following compound was prepared analogously to Example 15:

15a) 2-Amino-6-(3-(3-hydroxy-phenyl)allyl)-4,5,7,8-tetrahydro-6H-thiazolo[5,4-d]azepine Prepared from 2-amino-6-(3-(3-benzyloxy-phenyl)allyl)-4,5,7,8-tetrahydro-6H- thiazolo[5,4-d]azepine with 2 equivalents of boron tribromide in methylene chloride. Yield: 71% of theory, Melting point: 85°–95° C. (ether); foamy.

|             | C     | H    | N     |
|-------------|-------|------|-------|
| Calculated: | 63.77 | 6.36 | 13.96 |
| Found:      | 63.69 | 6.59 | 13.77 |

EXAMPLE 16

2-Amino-6-(3-(2-amino-phenyl)allyl)-4,5,7,8-tetrahydro-6H-thiazolo[5,4-d]azepine 1.0 g (3 mmol) of 2-amino-6-(3-(2-nitro-phenyl)-allyl)-4,5,7,8-tetrahydro-6H-thiazolo[5,4-d]azepine are hydrogenated under 1 bar of hydrogen using 1 g of Raney nickel in ethanol at ambient temperature (45 minutes). The catalyst is filtered off, the filtrate is evaporated down in vacuo and the evaporation residue is purified by column chromatography on silica gel (chloroform/methanol/conc. ammonia=90:10:0.5). Yield: 0.24 g (26% of theory), Melting point: 111°–116° C. (ether).

|             | C     | H    | N     |
|-------------|-------|------|-------|
| Calculated: | 63.98 | 6.71 | 18.65 |
| Found:      | 63.70 | 6.50 | 18.43 |

The following compounds were prepared analogously to Example 16:

16a) 2-Amino-6-(3-(4-amino-phenyl)allyl)-4,5,7,8-tetrahydro-6H-thiazolo[5,4-d]azepine. 0.5 $H_2O$ Prepared by catalytic hydrogenation of 2-amino-6-(3-(4-nitrophenyl)allyl)-4,5,7,8-tetrahydro-6H-thiazolo[5,4-d]azepine with Raney nickel in ethanol. Yield: 71% of theory, Melting point: 183°–187° C. (ether); sintering at 174° C.

|                              | C     | H    | N     |
|------------------------------|-------|------|-------|
| Calculated: (×0.5 $H_2O$)    | 62.10 | 6.84 | 18.11 |
| Found:                       | 62.24 | 6.85 | 17.95 |

16b) 2-Amino-6-(3-(3-amino-phenyl)allyl)-4,5,7,8-tetrahydro-6H-thiazolo[5,4-d]azepine-dihydrochloride-dihydrate. 0.33 isopropanol Prepared by catalytic hydrogenation of 2-amino-6-(3-(3-nitro-phenyl)allyl)-4,5,7,8-tetrahydro-6H- thiazolo[5,4-d]azepine using Raney nickel in anhydrous dimethylformamide (4.5 hours at ambient temperature). After purification by column chromatography the base is dissolved in isopropanol. By the addition of ethereal hydrochloric acid, cooling, filtering and drying at 100° C./0.1 torr over phosphorus pentoxide the title compound is obtained. Yield: 37% of theory, Melting point: 160° C. (decomp.).

|  | C | H | N |
|---|---|---|---|
| Calculated: (×2 HCl×2 H₂O×0.33 isopropanol); | 45.61 | 6.54 | 12.52 |
| Found: | 45.46 | 6.22 | 12.92 |

EXAMPLE 17

2-Amino-6-(2-phenyl-1-cyclopropyl-methyl)-4,5,7,8-tetrahydro-6H-thiazolo[5,4-d]azepine A solution of 2.0 g (6.4 mmol) of 2-amino-6-(2-phenyl-1-cyclopropyl-carbonyl)-4,5,7,8-tetrahydro-6H-thiazolo[5,4-d]azepine (melting point: 122°-126° C.; prepared from 2-phenyl-1-cyclopropyl-carboxylic acid chloride and 2 equivalents of 2-amino-4,5,7,8-tetrahydro-6H-thiazolo[5,4-d]azepine in chloroform) in 40 ml of tetrahydrofuran is added dropwise, with stirring and under nitrogen, to 0.73 g (19.1 mmol) of lithium aluminium hydride in 40 ml of tetrahydrofuran. The mixture is stirred for 2 hours in a bath at 40° C., then cooled, ethyl acetate is added to decompose any excess lithium aluminium hydride and hydrolysis is carried out by dropwise addition of saturated ammonium chloride solution. The precipitate is filtered off and the filtrate is evaporated down in vacuo. The evaporation residue is purified by column chromatography on silica gel (chloroform/methanol=10:1). Yield: 0.65 g (34% of theory), Melting point: 109°-113° C. (isopropanol).

|  | C | H | N |
|---|---|---|---|
| Calculated: | 68.21 | 7.07 | 14.04 |
| Found: | 68.25 | 7.11 | 14.10 |

EXAMPLE 18

2-Amino-6-(3-(4-aminocarbonyl-phenyl)allyl)-4,5,7,8-tetrahydro-6H-thiazolo[5,4-d]azepine. 0.5 H₂O 0.50 g (1.6 mmol) of 2-amino-6-(3-(4-cyano-phenyl)allyl)-4,5,7,8-tetrahydro-6H- thiazolo[5,4-d]azepine are heated in 5 g of polyphosphoric acid (85% diphosphorus pentoxide) for 30 minutes at 100° C. The mixture is cooled and made alkaline by the addition of ice with concentrated ammonia. The resulting mixture is extracted several times with chloroform (with the addition of 1% methanol), the chloroform solution is washed once with water, dried and filtered and then evaporated down in vacuo. The evaporation residue is crystallised from methanol. Yield: 0.33 (63% of theory), Melting point: 205°-210° C. (decomp.).

|  | C | H | N |
|---|---|---|---|
| Calculated: (×0.5 H₂O) | 60.55 | 6.27 | 16.60 |
| Found: | 60.69 | 6.18 | 16.48 |

EXAMPLE 19

2-Amino-6-(3-(4-ethoxycarbonyl-phenyl)allyl)-4,5,7,8-tetrahydro-6H-thiazolo[5,4-d]azepine Dry hydrochloric acid is introduced into a solution of 0.50 g (1.6 mmol) of 2-amino-6-(3-(4-cyanophenyl)allyl)-4,5,7,8-tetrahydro-6H- thiazolo[5,4-d]azepine in 50 ml of ethanol, with stirring and refluxing, until no more starting product can be detected. The mixture is evaporated down in vacuo, distributed between ¼ concentrated ammonia and chloroform, and the dried and filtered chloroform extract is evaporated down in vacuo. The evaporation residue is purified by column chromatography on silica gel (toluene/ethyl acetate/ethanol=4:2:2). Yield: 0.23 g (40% of theory), Melting point: 111°-115° C.

|  | C | H | N |
|---|---|---|---|
| Calculated: | 63.85 | 6.48 | 11.75 |
| Found: | 63.65 | 6.64 | 11.61 |

EXAMPLE 20

2-Amino-6-(4-phenyl-1-butyl)-4,5,7,8-tetrahydro-6H-thiazolo[5,4-d]azepine 3.0 g (20 mmol) of 4-phenyl-1-butanol and 1.9 ml (24.4 mmol) of methanesulphonyl chloride are stirred in 150 ml of anhydrous methylene chloride and at a reaction temperature of 20° C. a solution of 5.5 ml (40 mmol) of triethylamine in 30 ml of anhydrous methylene chloride is added. After stirring at ambient temperature overnight, extraction is carried out successively with 2N hydrochloric acid (saturated with sodium chloride), with saturated sodium chloride solution and with water. The dried and filtered methylene chloride phase is evaporated down in vacuo at 30° C.

The evaporation residue (crude 4-phenyl-1-butyl-mesylate) is dissolved in 75 ml of chloroform and this solution is rapidly added dropwise at ambient temperature to 6.7 g (40 mmol) of 2-amino-4,5,7,8-tetrahydro-6H-thiazolo[5,4-d]azepine in 130 ml of chloroform. The mixture is stirred for 15 hours at 60° C., diluted with 300 ml of chloroform and extracted once with 1N sodium hydroxide solution and twice with water. The organic phase is dried and filtered and then evaporated down in vacuo. The evaporation residue is purified by column chromatography on silica gel (chloroform/methanol=10:1). Yield: 1.28 g (21% of theory), Melting point: 147°-150° C.

|  | C | H | N |
|---|---|---|---|
| Calculated: | 67.75 | 7.69 | 13.94 |
| Found: | 67.90 | 7.52 | 13.99 |

The following compound was prepared analogously to Example 20:

20a) 2-Amino-6-(5-phenyl-1-pentyl)-4,5,7,8-tetrahydro-6H-thiazolo[5,4-d]azepine

Prepared from 5-phenyl-1-pentyl-mesylate and 2 equivalents of 2-amino-4,5,7,8-tetrahydro-6H- thiazolo[5,4-d]azepine in chloroform. Yield: 19% of theory, Melting point: 102°-105° C. (petroleum ether).

|  | C | H | N |
|---|---|---|---|
| Calculated: | 68.54 | 7.99 | 13.32 |
| Found: | 67.99 | 7.88 | 13.61 |

EXAMPLE 21

2-Amino-6-(3-(2,4-dimethoxy-phenyl)-1-propyl)-4,5,7,8-tetrahydro-6H-thiazolo[5,4-d]azepine (A) and 2-Amino-6-(3-(2,4-dimethoxy-phenyl)-3-hydroxy-1- propyl)-4,5,7,8-tetrahydro-6H-thiazolo[5,4-d]azepine (B)

To a solution of 5.0 g (13.8 mmol) of 2-amino-6-(3-(2,4-dimethoxy-phenyl)-3-oxo-1-propyl)-4,5,7,8-tetrahydro-6-thiazolo[5,4-d]azepine (oily base (melting point of the dihydrochloride 125°-130° C.); prepared from 3-chloro-1-(2,4-dimethoxy-phenyl)-1-oxo-propane with 1 equivalent of 2-amino-4,5,7,8-tetrahydro-6H-thiazolo[5,4-d]azepine in anhydrous dimethylformamide in the presence of 1 equivalent of potassium carbonate (40° C., 2 hours)) in a mixture of 50 ml of tetrahydrofuran and 5 ml of water, there is added, with stirring, in a bath at 40° C., 0.26 g (7 mmol) of sodium borohydride and after 30 minutes, two further batches of 0.26 g (7 mmol) of sodium borohydride. After the mixture has stood for 2 days at ambient temperature it is made acidic with 2N hydrochloric acid, stirred for 30 minutes and then evaporated down in vacuo until it is not quite dry. It is made alkaline with concentrated ammonia and extracted with chloroform. The dried and filtered chloroform solution is evaporated down in vacuo. The evaporation residue is purified by column chromatography on silica gel (toluene/ethyl acetate/methanol/conc. ammonia=4:3:1:0.15). First of all the title compound A is eluted. Yield: 0.13 g (2.6% of theory), Melting point: 105°-110° C. (ether).

|  | C | H | N |
|---|---|---|---|
| Calculated: | 62.21 | 7.25 | 12.09 |
| Found: | 62.11 | 7.38 | 11.95 |
| Molecular peak (m/z): Calculated: 347 Found: 347 | | | |

Then the title compound B is eluted. Yield: 0.46 g (9.2% of theory), Melting point: 45°-50° C. (foam). Molecular peak (m/z): Calculated: 363 Found: 363

EXAMPLE 22

2-Amino-6-(3-(2,4-dimethoxy-phenyl)allyl)-4,5,7,8-tetrahydro-6H-thiazolo[5,4-d]azepine 0.45 g (1.2 mmol) of 2-amino-6-(3-(2,4-dimethoxy-phenyl)-3-hydroxy-1-propyl)-4,5,7,8-tetrahydro-6H-thiazolo[5,4-d]azepine are stirred in 35 ml of anhydrous toluene together with 0.47 g (2.7 mmol) of p-toluenesulphonic acid hydrate and 7 g of molecular sieve (4Å) in a bath at 40° C. After one hour, a further 5 g of molecular sieve are added and after a total of 2 hours a further 2.5 g of molecular sieve are added. After a total of 3 hours at 40° C. the mixture is filtered through a glass frit coated with Celite and the filter cake is washed out several times with chloroform. The toluene and chloroform solutions are extracted with semi-concentrated ammonia and with water, then dried and filtered and evaporated down in vacuo. The combined evaporation residues are purified by column chromatography on silica gel (toluene/ethyl acetate/methanol/conc. ammonia=4:3:1:0.5). Yield: 43 mg (10% of theory), Melting point: 95°-100° C. (ether).

|  | C | H | N |
|---|---|---|---|
| Calculated: | 62.59 | 6.71 | 12.17 |
| Found: | 62.43 | 6.96 | 11.97 |
| Molecular peak (m/z): Calculated: 345 Found: 345 | | | |

EXAMPLE 23

2-Amino-6-(3-(2,4-dimethoxy-phenyl)-3-hydroxy-1-propyl)-4,5,7,8-tetrahydro-6H-thiazolo[5,4-d]azepine (B) and
2-Amino-6-(3-(3-ethoxy-3-(2,4-dimethoxy-phenyl)-1-propyl)-4,5,7,8-tetrahydro-6H-thiazolo[5,4-d]azepine (C)

Prepared analogously to Example 21 by reduction of 2-amino-6-(3-(2,4-dimethoxy-phenyl)-3-oxo-1-propyl)-4,5,7,8-tetrahydro-6H-thiazolo[5,4-d]azepine with sodium borohydride in ethanol. Purification by column chromatography on silica gel (toluene/ethyl acetate/methanol/conc. ammonia=4:3:1:0.15). First the title compound C is eluted. Yield: 9% of theory, Melting point: <20° C. Molecular peak (m/z): Calculated: 391 Found: 391 The base is converted with 2 equivalents of fumaric acid in acetone into the bis-fumaric acid salt of (C) with a melting point of 158°-160° C. (decomp.).

|  | C | H | N |
|---|---|---|---|
| Calculated: | 53.92 | 5.98 | 6.74 |
| Found: | 54.02 | 6.05 | 6.92 |

Subsequently the title compound B is eluted. Yield: 17% of theory, Melting point: 40°-50° C. (foam). Molecular peak (m/z): Calculated: 363 Found: 363

EXAMPLE 24

2-Amino-6-(3-(2-quinolinyl)allyl)-4,5,7,8-tetrahydro-6H-thiazolo[5,4-d]azepine. 0.2 H$_2$O To a solution of 3.1 g (16.7 mmol) of 3-(2-quinolinyl)allyl alcohol in 20 ml of chloroform, there is added dropwise with stirring and cooling with ice, at a reaction temperature of 5° C., a solution of 1.2 ml (16.7 mmol) of thionyl chloride in 10 ml of chloroform. The mixture is stirred for a further 15 minutes and evaporated in vacuo at 20° C. The evaporation residue (crude 3-(2-quinolinyl)allyl chloride hydrochloride) is dissolved at ambient temperature in 50 ml of anhydrous dimethylformamide. 8.5 g (50 mmol) of solid 2-amino-4,5,7,8-tetrahydro-6H-thiazolo[5,4-d]azepine are added thereto and the mixture is stirred for 12 hours at ambient temperature. It is evaporated down in vacuo and the evaporation residue is distributed between water and chloroform. The dried and filtered chloroform solution is evaporated down in vacuo. The evaporation residue is purified by column chromatography on silica gel (chloroform/methanol=10:1). Yield: 2.6 g (46% of theory), Melting point: 165°-170° C. (ether).

|  | C | H | N |
|---|---|---|---|
| Calculated: (×0.2H$_2$O) | 67.10 | 6.04 | 16.56 |
| Found: | 67.11 | 6.03 | 26.45 |

The following compound was prepared analogously to Example 24:

24a) 2-Amino-6-(3-(3-isoquinolinyl)allyl)-4,5,7,8-tetrahydro-6H-thiazolo[5,4-d]azepine. 0.5 H$_2$O Prepared from 3-(3-isoquinolinyl)allyl chloride hydrochloride (obtained from the corresponding allyl alcohol with thionyl chloride in chloroform at ambient temperature) and 3 equivalents of 2-amino-4,5,7,8-tetrahydro-6H-thiazolo[5,4-d]azepine in anhydrous dimethylformamide for 4 hours at 50° C. Yield: 45% of theory, Melting point: 196°-199° C. (ether).

|            | C     | H    | N     |
|------------|-------|------|-------|
| Calculated: (×0.5 H₂O) | 66.06 | 6.14 | 16.22 |
| Found:     | 65.98 | 6.01 | 16.14 |

EXAMPLE 25

2.(3-(4-Methoxy-phenyl)propionyl-amino)-6-(3-(3-pyridyl)allyl)-4,5,7,8-tetrahydro-6H-thiazolo[5,4-d]azepine To a stirred mixture of 1.0 g (3.5 mmol) of 2-amino-6-(3-(3-pyridyl)allyl)-4,5,7,8-tetrahydro-6H- thiazolo[5,4-d]azepine and 0.53 ml (3.8 mmol) of triethylamine in 40 ml of anhydrous chloroform, there is added dropwise at ambient temperature a solution of 3- (4-methoxyphenyl)-propionyl chloride (bp: 150° C./15 torr) in 7 ml of chloroform. The mixture is stirred for 3 hours at 60°-70° C., cooled and extracted with water. The dried and filtered chloroform solution is evaporated down in vacuo and the evaporation residue is purified by column chromatography on silica gel (chloroform/methanol=5:1). Yield: 0.74 g (47% of theory), Melting point: 168°-170° C. (ether).

|            | C     | H    | N     |
|------------|-------|------|-------|
| Calculated: | 66.95 | 6.29 | 12.49 |
| Found:     | 66.74 | 6.21 | 12.51 |

The following compound was prepared analogously to Example 25:

25a) 2-(3-(4-Methoxy-phenyl)propionyl-amino)-6-(3-(2-pyridyl)allyl)-4,5,7,8-tetrahydro-6H-thiazolo[5,4-d]azepine. 0.5 HCl Prepared by reacting 2-amino-6-(3-(2-pyridyl)-allyl)-4,5,7,8-tetrahydro-6H-thiazolo[5,4-d]azepine with 3-(4-methoxy-phenyl)-propionyl chloride. Yield: 42% of theory, Melting point: 37°-40° C.

|            | C     | H    | N      | Cl   |
|------------|-------|------|--------|------|
| Calc: (×0.5HCl) | 64.33 | 6.15 | 12.00° | 6.86 |
| Found:     | 64.11 | 6.03 | 11.98  | 6.90 |

EXAMPLE 26

2-Amino-6-(3-(4-isoquinolinyl)-2-propyn-1-yl)-4,5,7,8-tetrahydro-6H-thiazolo[5,4-d]azepine hydrate 11 mg (0.06 mmol) of copper(I)iodide and 42 mg (0.06 mmol) of bis-(triphenylphosphine)-palladium dichloride are added to a solution of 0.50 g (2.4 mmol) of 2-amino-6-propargyl-4,5,7,8-tetrahydro-6H-thiazolo[5,4-d]azepine and 0.50 g (2.4 mmol) of 4-bromo-isoquinoline in 30 ml of arhydrous triethylamine, which is stirred at 50° C. under nitrogen. The resulting mixture is stirred for 3 hours at 50° C. and for 2 hours at 70° C., during which time a precipitate is formed. Then another 11 mg of copper(I)iodide, 42 mg of bis-(triphenylphosphine)-palladium dichloride and 0.2 g (0.96 mmol) of 4-bromo-isoquinoline and 30 ml of anhydrous acetonitrile are added, causing solution to occur. After 1 hour's stirring at 70° C. the starting compound is no longer detectable by thin layer chromatography. The mixture is evaporated down in vacuo and the evaporation residue is distributed between chloroform and water. The dried and filtered chloroform solution is evaporated down in vacuo. The evaporation residue is purified by column chromatography on silica gel (acetone/methanol/conc. ammonia=50:12:0.4). Yield: 0.032 g (4% of theory), Melting point: 138°-142° C. (ether).

|            | C     | H    | N     |
|------------|-------|------|-------|
| Calculated: (×1H₂O) | 64.76 | 5.72 | 15.90 |
| Found:     | 64.68 | 5.72 | 16.14 |
| Molecular peak (m/z) Calculated: 334 Found: 334 | | | |

The following compound was obtained analogously to

Example 26:

26a) 2-Amino-6-(3-(2-oxo-indolin-4-yl)-2-propyn-1-yl)-4,5,7,8-tetrahydro-6H-thiazolo[5,4-d]azepine. 0.7 H₂O Prepared from 2-amino-6-propargyl-4,5,7,8-tetrahydro-6H-thiazolo[5,4-d]azepine and 4-bromo-2-oxo-indoline (melting point: 216°-220° C.) in triethylamine/acetonitrile (1:1) in the presence of catalytic amounts of copper(I)iodide and bis(triphenyl-phosphine)palladium dichloride in a Parr apparatus, with shaking, for 4 hours at 95 to 100° C. After purification by column chromatography on silica gel (chloroform/methanol/glacial acetic acid = 10:1:0.03) the product is distributed between chloroform and saturated sodium bicarbonate solution. Yield: 9.7% of theory, Melting point: 197°-199° C. (ether).

|            | C     | H    | N     |
|------------|-------|------|-------|
| Calculated: ×(0.75H₂O) | 61.42 | 5.58 | 15.92 |
| Found:     | 61.62 | 5.44 | 15.80 |
| Molecular peak (m/z) Calculated: 338 Found: 338 | | | |

EXAMPLE 27

2-Amino-6-(3-(5-indolyl)allyl)-4,5,7,8-tetrahydro-6H-thiazolo[5,4-d]azepine

At −15° C., a solution of 63 mg (0.55 mmol) of methanesulphochloride in 6 ml of chloroform is added dropwise to a stirred solution of 95 mg (0.55 mmol) of 3-(5-indolyl)allyl alcohol and 142 mg (1.10 mmol) of N-ethyl-N,N-diisopropylamine in 6 ml of anhydrous methylene chloride and the resulting mixture is stirred for 15 hours at −5° C. It is evaporated down in vacuo at 20° C., the evaporation residue is dissolved in 3 ml of anhydrous dimethylformamide, 370 mg (2.20 mmol) of 2-amino-4,5,7,8-tetrahydro-6H-thiazolo[5,4-d]azepine are added and the mixture is stirred for 4 hours at 50° C. and for 3 hours at 70° C. The mixture is then evaporated down in vacuo, distributed between chloroform and water and the dried and filtered chloroform solution is evaporated down in vacuo. The evaporation residue is purified by triple column chromatography on neutral aluminium oxide (toluene/ethyl acetate/ethanol=4:1:0.5). Yield: 8 mg (4.5% of theory), Melting point: 60°-65° C. (foamy). Molecular peak (m/z) Calculated: 324 Found: 324

EXAMPLE 28

2-Amino-6-(3-(2-bromo-phenyl)allyl)-4,5,7,8-tetrahydro- 6H-thiazolo[5,4-d]azepine Prepared analogously to Example 1 from 2-amino-4,5,7,8-tetrahydro-6H-thiazolo[5,4-d]azepine, potassium carbonate and 2-bromo-cinnamyl bromide in anhydrous dimethylformamide for 2 hours at 20° C. Yield: 42% of

EXAMPLE 29

2-Amino-6-(3-(3-trifluoromethyl-phenyl)allyl)-4,5,7,8-tetrahydro-6H-thiazolo[5,4-d]azepine Prepared analogously to Example 1 from 2-amino-4,5,7,8-tetrahydro-6H-thiazolo[5,4-d]azepine, potassium carbonate and 3-trifluoromethyl-cinnamyl bromide in anhydrous dimethylformamide for one hour at 20° C. Yield: 41% of theory, Melting point: 102°–105° C. (petroleum ether).

|  | C | H | N | Br |
|---|---|---|---|---|
| Calculated: | 57.77 | 5.13 | 11.89 | 9.07 |
| Found: | 57.91 | 5.08 | 11.97 | 9.38 |

EXAMPLE 30

2-Amino-6-(3-(2-cyano-phenyl)allyl)-4,5,7,8-tetrahydro-6H-thiazolo[5,4-d]azepine Prepared analogously to Example 1 from 2-amino-4,5,7,8-tetrahydro-6H-thiazolo[5,4-d]azepine, potassium carbonate and 2-cyano-cinnamyl bromide (melting point: 69°–71° C.) in anhydrous dimethylformamide for 15 hours at 20° C. Yield: 31% of theory, Melting point: 140°–144° C. (acetone).

|  | C | H | N |
|---|---|---|---|
| Calculated: | 65.79 | 5.85 | 18.05 |
| Found: | 65.74 | 5.75 | 18.10 |

EXAMPLE 31

2-Amino-6-(3-(3-cyano-phenyl)allyl)-4,5,7,8-tetrahydro-6H-thiazolo[5,4-d]azepine Prepared analogously to Example 1 from 2-amino-4,5,7,8-tetrahydro-6H-thiazolo[5,4-d]azepine, potassium carbonate and 3-cyano-cinnamyl bromide (melting point: 52°–55° C.) in anhydrous dimethylformamide for 2 hours at 20° C. Yield: 48% of theory, Melting point: 136°–140° C. (ether).

|  | C | H | N |
|---|---|---|---|
| Calculated: | 65.79 | 5.85 | 18.05 |
| Found: | 65.54 | 5.88 | 18.27 |

EXAMPLE 32

(E)-2-Amino-6-(3-(4-cyano-phenyl)allyl)-4,5,7,8-tetrahydro-6H-thiazolo[5,4-d]azepine Prepared analogously to Example 1 from 2-amino-4,5,7,8-tetrahydro-6H-thiazolo[5,4-d]azepine, potassium carbonate and 4-cyano-cinnamyl bromide (melting point: 79°–82° C.) in anhydrous dimethylformamide for one hour at 20° C. After the dimethylformamide has been distilled off in vacuo, the evaporation residue is distributed between ethyl acetate and water. After drying, filtering and evaporation of the organic phase, the evaporation residue is crystallised from acetone and the crystals are washed with ether. Yield: 49% of theory, Melting point: 199°–205° C. (decomp.).

|  | C | H | N |
|---|---|---|---|
| Calculated: | 65.79 | 5.85 | 18.05 |
| Found: | 65.51 | 6.02 | 18.12 |

200 MHz-$^1$H-NMR spectrum (CDCl$_3$):

| | |
|---|---|
| $\delta$ = 3.40 ppm (doublet), | 2H (allylic CH$_2$) |
| $\delta$ = 6.40 ppm (triplet) and | 1H (olefinic H) |
| $\delta$ = 6.48 ppm (triplet), | |
| $\delta$ = 6.58 ppm (doublet), | 1H (olefinic H) |

EXAMPLE 33

(E)-2-Amino-6-(3-(4-cyano-phenyl)allyl)-4,5,7,8-tetrahydro-6H-thiazolo[5,4-d]azepine hydrochloride 2.25 ml of 1N hydrochloric acid are added to 0.70 g (2.25 mmol) of (E)-2-amino-6-(3-(4-cyano-phenyl)allyl)-4,5,7,8-tetrahydro-6H-thiazolo[5,4-d]azepine in 10 ml of ethanol and the mixture is heated until the solution is clear. It is then cooled in an ice bath. The slowly precipitated crystals are filtered off. After washing with ethanol and with ether and drying at 100° C./4 torr, the monohydrochloride is obtained. Yield: 0.46 g (59% of theory), Melting point: 237° C. (decomp.).

|  | C | H | Cl | N |
|---|---|---|---|---|
| Calculated: | 58.85 | 5.52 | 10.22 | 16.15 |
| Found: | 58.67 | 5.45 | 10.18 | 16.05 |

EXAMPLE 34

(E)-2-Amino-6-(3-(4-cyano-phenyl)allyl)-4,5,7,8-tetrahydro-6H-thiazolo[5,4-d]azepine dihydrochloride. 0.25 H$_2$O 4.50 ml of 1N hydrochloric acid are added to 0.70 g (2.25 mmol) of (E)-2-amino-6-(3-(4-cyano-phenyl)allyl)-4,5,7,8-tetrahydro-6H-thiazolo[5,4-d]azepine in 10 ml of ethanol and heating is carried out until the solution is clear. Then it is evaporated to dryness in vacuo. ethanol is added to the foamy residue, it is evaporated down once more and this procedure with ethanol is repeated three times more. Then the product is dissolved in ethanol and heated ard cooled in ice. The crystals are filtered off and dried at 100° C./4 torr. Yield: 0.70 g (81% of theory), Melting point: 247°–250° C. (decomp.).

|  | C | H | Cl | N |
|---|---|---|---|---|
| Calculated: (×0.25H$_2$O) | 52.65 | 5.30 | 18.29 | 14.40 |
| Found: | 52.63 | 5.12 | 18.39 | 14.55 |

EXAMPLE 35

2-Amino-6-(3-(4-cyano-phenyl)-2-propyn-1-yl)-4,5,7,8-tetrahydro-6H-thiazolo[5,4-d]azepine. 0.3 H$_2$O Prepared analogously to Example 10 from 2-amino-6-propargyl-4,5,7,8-tetrahydro-6H-thiazolo[5,4-d]azepine, 4-bromo-benzonitrile and copper(I)iodide/bis(-triphenyl-phosphine)palladium dichloride in diethylamine for 6 hours at ambient temperature. Yield: 46% of theory, Melting point: 174°–176° C. (acetone).

--- theory, Melting point: 103°–106° C. (diisopropylether).

|  | C | H | Br | N |
|---|---|---|---|---|
| Calculated: | 52.75 | 4.98 | 21.94 | 11.54 |
| Found: | 52.84 | 4.98 | 22.14 | 11.53 |

| | C | H | N |
|---|---|---|---|
| Calculated: (×0.3H₂O) | 64.90 | 5.34 | 17.83 |
| Found: | 64.86 | 5.29 | 17.76 |

EXAMPLE 36

(Z)-2-Amino-6-(3-(4-cyano-phenyl)allyl)-4,5,7,8-tetrahydro-6H-thiazolo[5,4-d]azepine Prepared analogously to Example 12 by catalytic hydrogenation of 1.30 g (4.21 mmol) of 2-amino-6-(3-(4-cyano-phenyl)-2-propyn-1-yl)-4,5,7,8-tetrahydro-6H-thiazolo[5,4-d]azepine. 0.3 H₂O in anhydrous dimethylformamide under 1 bar of hydrogen pressure using Lindlar catalyst (5% palladium on calcium carbonate, contaminated with lead) at ambient temperature. Yield: 29.5% of theory, Melting point: 186°–188° C. (ether).

| | C | H | N |
|---|---|---|---|
| Calculated: | 65.79 | 5.85 | 18.05 |
| Found: | 65.68 | 5.84 | 18.07 |
| 200 MHz-¹H-NMR spectrum (d6-DMSO): | | | |
| $\delta$ = 3.42 ppm (doublet), | | 2H (allylic CH₂) | |
| $\delta$ = 5.95 ppm (triplet) and | | 1H (olefinic H) | |
| $\delta$ = 6.01 ppm (triplet), J = 11.7 Hz, | | | |
| $\delta$ = 6.62 ppm (doublet), | | 1H (olefinic H) | |

EXAMPLE 37

2-Amino-6-(3-(2-aminocarbonyl-phenyl)allyl)-4,5,7,8-tetrahydro-6H-thiazolo[5,4-d]azepine. 0.25 HCl Prepared analogously to Example 18 from 2-amino-6-(3-(2-cyano-phenyl)allyl)-4,5,7,8-tetrahydro-6H-thiazolo[5,4-d]azepine by heating for four hours in polyphosphoric acid in a bath at 100° C. Yield: 58% of theory, Melting point: 185°–188° C.

| | C | H | Cl | N |
|---|---|---|---|---|
| Calculated: (×0.25H₂O) | 60.55 | 6.05 | 2.63 | 16.61 |
| Found: | 60.30 | 5.96 | 2.24 | 16.45 |

EXAMPLE 38

2-Amino-6-(3-(3-aminocarbonyl-phenyl)allyl)-4,5,7,8-tetrahydro-6H-thiazolo[5,4-d]azepine. 0.25 H₂O Prepared analogously to Example 18 from 2-amino-6-(3-(3-cyano-phenyl)allyl)-4,5,7,8-tetrahydro-6H-thiazolo[5,4-d]azepine by heating for 1.5 hours in polyphosphoric acid at 100° C. Yield: 69% of theory, Melting point: 210°–212° C.

| | C | H | N |
|---|---|---|---|
| Calculated: | 61.33 | 6.21 | 16.83 |
| Found: | 61.54 | 5.98 | 16.62 |

EXAMPLE 39

2-Amino-6-(3-(3-(2-pyridylmethoxy)phenyl)allyl)-4,5,7,8-tetrahydro-6H-thiazolo[5,4-d]azepine A solution of 57 mg (0.33 mmol) of diethyl-azodicarboxylate in 0.15 ml of anhydrous tetrahydrofuran is added dropwise, with stirring and cooling (internal temperature 0° C.), to 100 mg (0.33 mmol) of 2-amino-6-(3-(3-hydroxy-phenyl)allyl)-4,5,7,8-tetrahydro-6H-thiazolo[5,4-d]azepine and 36 mg (0.33 mmol) of 2-(hydroxymethyl)-pyridine and 86 mg (0.33 mmol) of triphenylphosphine in 1 ml of anhydrous tetrahydrofuran. After stirring overnight, whilst heating to ambient temperature, a further 0.33 mmol of triphenylphosphine and diethyl-azodicarboxylate are added at 0° C. and the mixture is stirred for another hour at ambient temperature. It is evaporated down in vacuo and distributed between ethyl acetate and water. The ethyl acetate phase is extracted with 2N hydrochloric acid. The aqueous hydrochloric acid phase is made alkaline with conc. ammonia and extracted with ethyl acetate; the organic phase is dried, filtered and evaporated down in vacuo. The evaporation residue is purified by column chromatography on silica gel (chloroform/methanol=5:1). Yield: 13 mg (10% of theory), Melting point: 35°–40° C. (foamy). Molecular peak (m/z): Calculated: 392 Found: 392

EXAMPLE 40

(Z)-2-Amino-6-(3-(2-oxo-indolin-4-yl)-2-propen-1-yl)-4,5,7,8-tetrahydro-6H-thiazolo[5,4-d]azepine Prepared analogously to Example 12 by catalytic hydrogenation of 2-amino-6-(3-(2-oxo-indolin-4-yl)-2-propyn-1-yl)-4,5,7,8-tetrahydro-6H- thiazolo[5,4-d]azepine. 0.75 H₂O using Lindlar catalyst (palladium on calcium carbonate, contaminated with lead) for 3 hours at ambient temperature in ethanol. Yield: 51% of theory, Melting point: 192°–195° C. (acetone/ether).

| | C | H | N |
|---|---|---|---|
| Calculated: | 63.52 | 5.92 | 16.46 |
| Found: | 63.38 | 6.01 | 16.29 |
| Molecular peak (m/z): Calculated: 340 Found: 340 | | | |
| 200 MHz-¹H-NMR spectrum (d6-DMSO/CD₃OD): | | | |
| $\delta$ = 3.38 ppm (doublet), | | 2H (allylic CH₂) | |
| $\delta$ = 5.82 ppm (triplet) and | | 1H (olefinic H) | |
| $\delta$ = 5.88 ppm (triplet), J = 12 Hz, | | | |
| $\delta$ = 6.49 ppm (doublet), | | 1H (olefinic H) | |

EXAMPLE 41

2-Amino-6-(2H-1-benzopyran-3-yl)methyl-4,5,7,8-tetrahydro-6H-thiazolo[5,4-azepine Prepared analogously to Example 1 from 2-amino-4,5,7,8-tetrahydro-6H-thiazolo[5,4-d]azepine, potassium carbonate, and 3-bromomethyl-2H-1-benzopyran in anhydrous dimethylformamide for 72 hours at ambient temperature. Yield: 13% of theory, Melting point: 150°–153° C. (petroleum ether/ether). Molecular peak (m/z): Calculated: 313 Found: 313

EXAMPLE 42

2-Amino-6-(3-(3-benzothiaphenyl)allyl)-4,5,7,8-tetrahydro-6H-thiazolo[5,4-d]azepine Prepared analogously to Example 1 from 2-amino-4,5,7,8-tetrahydro-6H-thiazolo[5,4-d]azepine, potassium carbonate and 3-(3-benzothiophenyl)allyl bromide in anhydrous dimethylformamide for 15 hours at ambient temperature. Yield: 12% of theory, Melting point: 148°–152° C. Molecular peak (m/z): Calculated: 341 Found: 341

EXAMPLE 43

2-Amino-6-(3-(3(2)-hydroxy-2(3)-methoxy-phenyl)allyl)-4,5,7,8-tetrahydro-6H-thiazolo[5,4-d]azepine Prepared analogously to Example 15 from 2-amino-6-(3-(2,3-dimethoxy-phenyl)allyl)-4,5,7,8-tetrahydro-6H-thiazolo[5,4-d]azepine with 2 equivalents of boron tribromide in methylene chloride. Yield: 29% of theory, Melting point: 50°–55° C. Molecular peak (m/z): Calculated: 331 Found: 331 The following compounds may be prepared analogously to the preceding Examples:

2-amino-6-(3-(2-trifluoromethyl-phenyl)allyl)-4,5,7,8-tetrahydro-6H-thiazolo[5,4-d]azepine 2-amino-6-(3-(4-trifluoromethyl-phenyl)allyl)-4,5,7,8-tetrahydro-6H-thiazolo[5,4-d]azepine 2-amino-6-(3-(3-ethoxy-phenyl)allyl)-4,5,7,8-tetrahydro-H-thiazolo[5,4-d]azepine 2-amino-6-(3-(4-ethoxy-phenyl)allyl)-4,5,7,8-tetrahydro-H-thiazolo[5,4-d]azepine 2-amino-6-(3-(2-dimethylamino-phenyl)allyl)-4,5,7,8-tetrahydro-6H-thiazolo[5,4-d]azepine 2-amino-6-(3-(3-dimethylamino-phenyl)allyl)-4,5,7,8-tetrahydro-6H-thiazolo[5,4-d]azepine 2-amino-6-(3-(3-piperidino-phenyl)allyl)-4,5,7,8-tetrahydro-6H-thiazolo[5,4-d]azepine 2-amino-6-(3-(4-piperidino-phenyl)allyl)-4,5,7,8-tetrahydro-6H-thiazolo[5,4-d]azepine 2-amino-6-(3-(2-acetylamino-phenyl)allyl)-4,5,7,8-tetrahydro-6H-thiazolo[5,4-d]azepine 2-amino-6-(3-(3-acetylamino-phenyl)allyl)-4,5,7,8-tetrahydro-6H-thiazolo[5,4-d]azepine 2-amino-6-(3-(4-acetylamino-phenyl)allyl)-4,5,7,8-tetrahydro-6H-thiazolo[5,4-d]azepine 2-amino-6-(3-(2-carboxy-phenyl)allyl)-4,5,7,8-tetrahydro-6H-thiazolo[5,4-d]azepine 2-amino-6-(3-(3-carboxy-phenyl)allyl)-4,5,7,8-tetrahydro-6H-thiazolo[5,4-d]azepine 2-amino-6-(3-(4-carboxy-phenyl)allyl)-4,5,7,8-tetrahydro-6H-thiazolo[5,4-d]azepine 2-amino-6-(3-(2-(2-pyridylmethoxy)phenyl)allyl)-4,5,7,8-tetrahydro-6H-thiazolo[5,4-d]azepine 2-amino-6-(3-(4-(2-pyridylmethoxy)phenyl)allyl)-4,5,7,8-tetrahydro-6H-thiazolo[5,4-d]azepine 2-amino-6-(3-(2-(3-pyridylmethoxy)phenyl)allyl)-4,5,7,8-tetrahydro-6H-thiazolo[5,4-d]azepine 2-amino-6-(3-(3-(3-pyridylmethoxy)phenyl)allyl)-4,5,7,8-tetrahydro-6H-thiazolo[5,4-d]azepine 2-amino-6-(3-(4-(3-pyridylmethoxy)phenyl)allyl)-4,5,7,8-tetrahydro-6H-thiazolo[5,4-d]azepine 2-amino-6-(3-(2-(4-pyridylmethoxy)phenyl)allyl)-4,5,7,8-tetrahydro-6H-thiazolo[5,4-d]azepine 2-amino-6-(3-(3-(4-pyridylmethoxy)phenyl)allyl)-4,5,7,8-tetrahydro-6H-thiazolo[5,4-d]azepine 2-amino-6-(3-(4-(4-pyridylmethoxy)phenyl)allyl)-4,5,7,8-tetrahydro-6H-thiazolo[5,4-d]azepine 2-amino-6-(3-(4-quinolinyl)allyl)-4,5,7,8-tetrahydro-6H-thiazolo[5,4-d]azepine 2-amino-6-(3-(5-quinolinyl)allyl)-4,5,7,8-tetrahydro-6H-thiazolo[5,4-d]azepine 2-amino-6-(3-(6-quinolinyl)allyl)-4,5,7,8-tetrahydro-6H-thiazolo[5,4-d]azepine 2-amino-6-(3-(7-quinolinyl)allyl)-4,5,7,8-tetrahydro-6H-thiazolo[5,4-d]azepine 2-amino-6-(3-(8-quinolinyl)allyl)-4,5,7,8-tetrahydro-6H-thiazolo[5,4-d]azepine 2-amino-6-(3-(5-isoquinolinyl)allyl)-4,5,7,8-tetrahydro-6H-thiazolo[5,4-d]azepine 2-amino-6-(3-(6-isoquinolinyl)allyl)-4,5,7,8-tetrahydro-H-thiazolo[5,4-d]azepine 2-amino-6-(3-(7-isoquinolinyl)allyl)-4,5,7,8-tetrahydro-H-thiazolo[5,4-d]azepine 2-amino-6-(3-(8-isoquinolinyl)allyl)-4,5,7,8-tetrahydro-H-thiazolo[5,4-d]azepine 2-amino-6-(3-(indolin-2-on-4-yl)allyl)-4,5,7,8-tetrahydro-H-thiazolo[5,4-d]azepine 2-amino-6-(3-(indolin-2-on-5-yl)allyl)-4,5,7,8-tetrahydro-6H-thiazolo[5,4-d]azepine 2-amino-6-(3-(indolin-2-on-6-yl)allyl)-4,5,7,8-tetrahydro-6H-thiazolo[5,4-d]azepine 2-amino-6-(3-(indolin-2-on-7-yl)allyl)-4,5,7,8-tetrahydro-6H-thiazolo[5,4-d]azepine 2-amino-6-(3-(5-carbostyril)allyl)-4,5,7,8-tetrahydro-H-thiazolo[5,4-d]azepine 2-amino-6-(3-(6-carbostyril)allyl)-4,5,7,8-tetrahydro-H-thiazolo[5,4-d]azepine 2-amino-6-(3-(3,4-dihydro-5-carbostyril)allyl)-4,5,7,8-tetrahydro-6H-thiazolo[5,4-d]azepine 2-amino-6-(3-(3,4-dihydro-6-carbostyril)allyl)-4,5,7,8-tetrahydro-6H-thiazolo[5,4-d]azepine 2-amino-6-(3-(2-methyl-4-benzothiazolyl)allyl)-4,5,7,8--amino-6-(3-(2-methyl-5-benzothiazolyl)allyl)-4,5,7,8-tetrahydro-6H-thiazolo[5,4-d]azepine 2-amino-6-(3-(2-methyl-5-benzothiazolyl)allyl)-4,5,7,8-tetrahydro-6H-thiazolo[5,4-d]azepine 2-amino-6-(3-(2-methyl-6-benzothiazolyl)allyl)-4,5,7,8-tetrahydro-6H-thiazolo[5,4-d]azepine 2-amino-6-(3-(2-methyl-7-benzothiazolyl)allyl)-4,5,7,8-tetrahydro-6H-thiazolo[5,4-d]azepine 2-amino-6-(3-(2-amino-4-benzothiazolyl)allyl)-4,5,7,8-tetrahydro-6H-thiazolo[5,4-d]azepine 2-amino-6-(3-(2-amino-5-benzothiazolyl)allyl)-4,5,7,8-tetrahydro-6H-thiazolo[5,4-d]azepine 2-amino-6-(3-(2-amino-6-benzothiazolyl)allyl)-4,5,7,8-tetrahydro-6H-thiazolo[5,4-d]azepine 2-amino-6-(3-(2-amino-7-benzothiazolyl)allyl)-4,5,7,8-tetrahydro-6H-thiazolo[5,4-d]azepine 2-amino-6-(3-(2-methyl-4-benzoxazolyl)allyl)-4,5,7,8-tetrahydro-6H-thiazolo[5,4-d]azepine 2-amino-6-(3-(2-methyl-5-benzoxazolyl)allyl)-4,5,7,8-tetrahydro-6H-thiazolo[5,4-d]azepine 2-amino-6-(3-(2-methyl-4-benzimidazolyl)allyl)-4,5,7,8-tetrahydro-6H-thiazolo[5,4-d]azepine 2-amino-6-(3-(2-methyl-5-benzimidazolyl)allyl)-4,5,7,8-tetrahydro-6H-thiazolo[5,4-d]azepine 2-amino-6-(3-(2-phenyl-4-benzimidazolyl)allyl)-4,5,7,8-tetrahydro-6H-thiazolo[5,4-d]azepine 2-amino-6-(3-(2-phenyl-5-benzimidazolyl)allyl)-4,5,7,8-tetrahydro-6H-thiazolo[5,4-d]azepine 2-amino-6-(3-(2-amino-4-benzimidazolyl)allyl)-4,5,7,8-tetrahydro-6H-thiazolo[5,4-d]azepine 2-amino-6-(3-(2-amino-5-benzimidazolyl)allyl)-4,5,7,8-tetrahydro-6H-thiazolo[5,4-d]azepine 2-amino-6-(3-(2,3-dihydroxy-phenyl)allyl)-4,5,7,8-tetrahydro-6H-thiazolo[5,4-d]azepine 2-amino-6-(3-(2,5-dihydroxy-phenyl)allyl)-4,5,7,8-tetrahydro-6H-thiazolo[5,4-d]azepine 2-amino-6-(3-(2,6-dihydroxy-phenyl)allyl)-4,5,7,8-tetrahydro-6H-thiazolo[5,4-d]azepine 2-amino-6-(3-(3,4-dihydroxy-phenyl)allyl)-4,5,7,8-tetrahydro-6H-thiazolo[5,4-d]azepine 2-amino-6-(3-(3,5-dihydroxy-phenyl)allyl)-4,5,7,8-tetrahydro-6H-thiazolo[5,4-d]azepine 2-amino-6-(3-(2-hydroxy-3-methyl-phenyl)allyl)-4,5,7,8-tetrahydro-6H-thiazolo[5,4-d]azepine 2-amino-6-(3-(2-hydroxy-4-methyl-phenyl)allyl)-4,5,7,8-tetrahydro-6H-thiazolo[5,4-d]azepine 2-amino-6-(3-(2-hydroxy-5-methyl-phenyl)allyl)-4,5,7,8-tetrahydro-6H-thiazolo[5,4-d]azepine 2-amino-6-(3-(2-hydroxy-6-methyl-phenyl)allyl)-
  4,5,7,8-2-amino-6-(3-(3-hydroxy-2-methyl-phenyl)al-
  lyl)-4,5,7,8-tetrahydro-6H-thiazolo[5,4-d]azepine
2-amino-6-(3-(3-hydroxy-2-methyl-phenyl)allyl)-
  4,5,7,8-tetrahydro-6H-thiazolo[5,4-d]azepine
2-amino-6-(3-(3-hydroxy-4-methyl-phenyl)allyl)-
  4,5,7,8-tetrahydro-6H-thiazolo[5,4-d]azepine
2-amino-6-(3-(3-hydroxy-5-methyl-phenyl)allyl)-
  4,5,7,8-tetrahydro-6H-thiazolo[5,4-d]azepine
2-amino-6-(3-(5-hydroxy-2-methyl-phenyl)allyl)-
  4,5,7,8-tetrahydro-6H-thiazolo[5,4-d]azepine
2-amino-6-(3-(2-hydroxy-3-methoxy-phenyl)allyl)-
  4,5,7,8-tetrahydro-6H-thiazolo[5,4-d]azepine
2-amino-6-(3-(2-hydroxy-4-methoxy-phenyl)allyl)-
  4,5,7,8-tetrahydro-6H-thiazolo[5,4-d]azepine
2-amino-6-(3-(2-hydroxy-5-methoxy-phenyl)allyl)-
  4,5,7,8-tetrahydro-6H-thiazolo[5,4-d]azepine
2-amino-6-(3-(2-hydroxy-6-methoxy-phenyl)allyl)-
  4,5,7,8-tetrahydro-6H-thiazolo[5,4-d]azepine
2-amino-6-(3-(3-hydroxy-2-methoxy-phenyl)allyl)-
  4,5,7,8-tetrahydro-6H-thiazolo[5,4-d]azepine
2-amino-6-(3-(3-hydroxy-4-methoxy-phenyl)allyl)-
  4,5,7,8-tetrahydro-6H-thiazolo[5,4-d]azepine
2-amino-6-(3-(3-hydroxy-5-methoxy-phenyl)allyl)-
  4,5,7,8-tetrahydro-6H-thiazolo[5,4-d]azepine
2-amino-6-(3-(5-hydroxy-2-methoxy-phenyl)allyl)-
  4,5,7,8-tetrahydro-6H-thiazolo[5,4-d]azepine
2-amino-6-(3-(3-benzyloxy-2-methyl-phenyl)allyl)-
  4,5,7,8-tetrahydro-6H-thiazolo[5,4-d]azepine
2-amino-6-(3-(3-benzyloxy-4-methyl-phenyl)allyl)-
  4,5,7,8-tetrahydro-6H-thiazolo[5,4-d]azepine
2-amino-6-(3-(3-benzyloxy-5-methyl-phenyl)allyl)-
  4,5,7,8-tetrahydro-6H-thiazolo[5,4-d]azepine
2-amino-6-(3-(5-benzyloxy-2-methyl-phenyl)allyl)-
  4,5,7,8-tetrahydro-6H-thiazolo[5,4-d]azepine
2-amino-6-(3-(3-benzyloxy-2-methoxy-phenyl)allyl)-
  4,5,7,8-tetrahydro-6H-thiazolo[5,4-d]azepine
2-amino-6-(3-(3-benzyloxy-4-methoxy-phenyl)allyl)-
  4,5,7,8-tetrahydro-6H-thiazolo[5,4-d]azepine
2-amino-6-(3-(3-benzyloxy-5-methoxy-phenyl)allyl)-
  4,5,7,8-tetrahydro-6H-thiazolo[5,4-d]azepine
2-amino-6-(3-(5-benzyloxy-2-methoxy-phenyl)allyl)-
  4,5,7,8-tetrahydro-6H-thiazolo[5,4-d]azepine
2-amino-6-(3-(3,4,5-trihydroxy-phenyl)allyl)-4,5,7,8-tet-
  rahydro-6H-thiazolo[5,4-d]azepine
2-amino-6-(3-(4-methyl-2-pyridyl)allyl)-4,5,7,8-tetrahy-
  dro-H-thiazolo[5,4-d]azepine
2-amino-6-(3-(5-chloro-2-pyridyl)allyl)-4,5,7,8-tetrahy-
  dro-H-thiazolo[5,4-d]azepine
2-amino-6-(3-(3-methoxy-2-pyridyl)allyl)-4,5,7,8-tet-
  rahydro-6H-thiazolo[5,4-d]azepine
2-amino-6-(3-(3-benzyloxy-2-pyridyl)allyl)-4,5,7,8-tet-
  rahydro-6H-thiazolo[5,4-d]azepine
2-amino-6-(3-(6-benzyloxy-2-pyridyl)allyl)-4,5,7,8-tet-
  rahydro-6H-thiazolo[5,4-d]azepine
2-amino-6-(3-(2-methoxy-3-pyridyl)allyl)-4,5,7,8-tet-
  rahydro-6H-thiazolo[5,4-d]azepine
2-amino-6-(3-(2-methoxy-phenyl)-2-propyn-1-yl)-
  4,5,7,8-tetrahydro-6H-thiazolo[5,4-d]azepine
2-amino-6-(3-(3-methoxy-phenyl)-2-propyn-1-yl)-
  4,5,7,8-tetrahydro-6H-thiazolo[5,4-d]azepine
2-amino-6-(3-(4-methoxy-phenyl)-2-propyn-1-yl)-
  4,5,6,7-tetrahydro-6H-thiazolo[5,4-d]azepine
2-amino-6-(3-(2-benzyloxy-phenyl)-2-propyn-1-yl)-
  4,5,7,8-tetrahydro-6H-thiazolo[5,4-d]azepine
2-amino-6-(3-(3-benzyloxy-phenyl)-2-propyn-1-yl)-
  4,5,7,8-tetrahydro-6H-thiazolo[5,4-d]azepine
2-amino-6-(3-(4-benzyloxy-phenyl)-2-propyn-1-yl)-
  4,5,7,8-tetrahydro-6H-thiazolo[5,4-d]azepine
2-amino-6-(3-(5-chloro-2-pyridyl)-2-propyn-1-yl)-
  4,5,7,8-tetrahydro-6H-thiazolo[5,4-d]azepine
2-amino-6-(3-(1-naphthyl)-2-propyn-1-yl)-4,5,7,8-tet-
  rahydro-6H-thiazolo[5,4-d]azepine
-amino-6-(3-(2-naphthyl)-2-propyn-1-yl)-4,5,7,8-tet-
  rahydro-6H-thiazolo[5,4-d]azepine
2-amino-6-(3-(2-quinolinyl)-2-propyn-1-yl)-4,5,7,8-tet-
  rahydro-6H-thiazolo[5,4-d]azepine
2-amino-6-(3-(3-quinolinyl)-2-propyn-1-yl)-4,5,7,8-tet-
  rahydro-6H-thiazolo[5,4-d]azepine
2-amino-6-(3-(4-quinolinyl)-2-propyn-1-yl)-4,5,7,8-tet-
  rahydro-6H-thiazolo[5,4-d]azepine
2-amino-6-(3-(1-isoquinolinyl)-2-propyn-1-yl)-4,5,7,8-
  tetrahydro-6H-thiazolo[5,4-d]azepine
2-amino-6-(3-(3-isoquinolinyl)-2-propyn-1-yl)-4,5,7,8-
  tetrahydro-6H-thiazolo[5,4-d]azepine
2-amino-6-(2-(1-naphthyl)-1-cyclopropyl-methyl)-
  4,5,7,8-tetrahydro-6H-thiazolo[5,4-d]azepine
2-amino-6-(2-(2-naphthyl)-1-cyclopropyl-methyl)-
  4,5,7,8-tetrahydro-6H-thiazolo[5,4-d]azepine
2-amino-6-(2-(2-pyridyl)-1-cyclopropyl-methyl)-4,5,7,8-
  tetrahydro-6H-thiazolo[5,4-d]azepine
2-amino-6-(2-(3-pyridyl)-1-cyclopropyl-methyl)-4,5,7,8-
  tetrahydro-6H-thiazolo[5,4-d]azepine
2-amino-6-(2-(4-pyridyl)-1-cyclopropyl-methyl)-4,5,7,8-
  tetrahydro-6H-thiazolo[5,4-d]azepine
2-amino-6-((2H-1-benzopyran-3-yl)-methyl)-4,5,7,8-tet-
  rahydro-6H-thiazolo[5,4-d]azepine
2-amino-6-((2-methyl-2H-1-benzopyran-3-yl)methyl)-
  4,5,7,8-tetrahydro-6H-thiazolo[5,4-d]azepine
2-amino-6-((2,2-dimethyl-2H-1-benzopyran-3-yl)me-
  thyl)-4,5,7,8-tetrahydro-6H-thiazolo[5,4-d]azepine
2-amino-6-((2H-1-benzothiopyran-3-yl)methyl)-4,5,7,8-
  tetrahydro-6H-thiazolo[5,4-d]azepine
2-amino-6-((2-methyl-2H-1-benzothiopyran-3-yl)me-
  thyl)-4,5,7,8-tetrahydro-6H-thiazolo[5,4-d]azepine
2-amino-6-((2,2-dimethyl-2H-1-benzothiopyran-3-
  yl)methyl)-4,5,7,8-tetrahydro-6H-thiazolo[5,4-d]aze-
  pine
2-amino-6-(3-(3-hydroxy-2-pyridyl)allyl)-4,5,7,8-tet-
  rahydro-6H-thiazolo[5,4-d]azepine
2-amino-6-(3-(6-hydroxy-2-pyridyl)allyl)-4,5,7,8-tet-
  rahydro-6H-thiazolo[5,4-d]azepine
2-amino-6-(3-(2-benzothiophenyl)allyl)-4,5,7,8-tetrahy-
  dro-6H-thiazolo[5,4-d]azepine
2-amino-6-(3-(4-benzothiophenyl)allyl)-4,5,7,8-tetrahy-
  dro-6H-thiazolo[5,4-d]azepine
2-amino-6-(3-(5-benzothiophenyl)allyl)-4,5,7,8-tetrahy-
  dro-6H-thiazolo[5,4-d]azepine
2-amino-6-(3-(6-benzothiophenyl)allyl)-4,5,7,8-tetrahy-
  dro-6H-thiazolo[5,4-d]azepine
2-amino-6-(3-(7-benzothiophenyl)allyl)-4,5,7,8-tetrahy-
  dro-6H-thiazolo[5,4-d]azepine

EXAMPLE A

Tablets containing 5 mg of 2-amino-6-(3-(4-cyanophenyl)allyl)-4,5,7,8-tetrahydro-6H-thiazolo[5,4-d]-azepine Composition:
1 tablet contains:

| | |
|---|---|
| Active substance (1) | 5.0 mg |
| Corn starch (2) | 62.0 mg |
| Lactose (3) | 48.0 mg |
| Polyvinylpyrrolidone (4) | 4.0 mg |

-continued

| Composition: 1 tablet contains: | |
|---|---|
| Magnesium stearate (5) | 1.0 mg |
| | 120.0 mg |

Method of Preparation (1), (2), (3) and (4) are mixed together and moistened with water. The moist mixture is passed through a screen with a mesh size of 1.5 mm and dried at about 45° C. The dry granules are passed through a 1.0 mm mesh screen and mixed with (5). The finished mixture is compressed in a tablet press with punches 7 mm in diameter provided with a dividing slot, to form tablets. Weight of tablet: 120 mg

EXAMPLE B

Tablets containing 2.5 mg of 2-amino-6-(3-(4-cyano-phenyl)allyl)-4,5,7,8-tetrahydro-6H-thiazolo[5,4-d]-azepine

| Composition: 1 tablet contains: | |
|---|---|
| Active substance | 2.5 mg |
| Corn starch | 64.5 mg |
| Lactose | 48.0 mg |
| Polyvinylpyrrolidone | 4.0 mg |
| Magnesium stearate | 1.0 mg |
| | 120.0 mg |

Method of Preparation

The mixture of active substance, lactose and corn starch is moistened with a 20% solution of polyvinylpyrrolidone in water. The moist mass is granulated through a screen with a mesh size of 1.5 mm and dried at 45° C. The dried granules are passed through a screen with a 1 mm mesh and homogeneously mixed with magnesium stearate. Weight of tablet: 120 mg Punch: 7 mm diameter with dividing slot

EXAMPLE C

Coated tablets containing 2.5 mg of 2-amino-6-(3-(4-cyano-phenyl)allyl)-4,5,7,8-tetrahydro-6H- thiazolo[5,4-d]azepine

| Composition: 1 tablet core contains: | |
|---|---|
| Active substance (1) | 2.5 mg |
| Potato starch (2) | 44.0 mg |
| Lactose (3) | 30.0 mg |
| Polyvinylpyrrolidone (4) | 3.0 mg |
| Magnesium stearate (5) | 0.5 mg |
| | 80.0 mg |

Method of Preparation 1, 2, 3 and 4 are thoroughly mixed and moistened with water. The moist mass is pressed through a sieve with a mesh size of 1.0 mm, dried at about 45° C. and the granules are then passed through the same sieve. After the addition of 5, convex tablet cores with a diameter of 6 mm are produced by compressing in a tablet-making machine. The tablet cores thus produced are coated in known manner with a coating consisting essentially of sugar and talc. The finished coated tablets are polished with wax. Weight of coated tablet: 120 mg

EXAMPLE D

Coated tablets containing 5 mg of 2-amino-6-(3-(4-cyano-phenyl)allyl)-4,5,7,8-tetrahydro-6H-thiazolo[5,4-d]-azepine

| Composition: 1 tablet core contains: | |
|---|---|
| Active substance | 5.0 mg |
| Secondary calcium phosphate | 70.0 mg |
| Corn starch | 50.0 mg |
| Polyvinylpyrrolidone | 4.0 mg |
| Magnesium stearate | 1.0 mg |
| | 130.0 mg |

Method of Preparation

The mixture of active substance, calcium phosphate and corn starch is moistened with a 15% solution of polyvinylpyrrolidone in water. The moist mass is passed through a screen with a mesh size of 1 mm, dried at 45 C and then passed through the same screen. After mixing with the specified quantity of magnesium stearate, tablet cores are compressed therefrom. Weight of core: 130 mg Punch: 7 mm in diameter A coating of sugar and talc is applied in known manner to the tablet cores thus produced. The finished coated tablets are polished with wax. Weight of coated tablet 180 mg.

What is claimed is:

1. 4,5,7,8-tetrahydro-6-thiazoloazepines of general formula II $$R_1-A-CH_2-N\underset{}{\overset{}{\diagdown}}\phantom{...} \text{(II)}$$

wherein
A represents a group of the formulae $$-\underset{*}{C}(R_3)=CH-,\ -\underset{*}{CH}=C(R_4)-,\ -\underset{*}{CH}\overset{CH_2}{\diagdown}CH-,$$

$$-\underset{*}{C}\equiv C-,\ -\underset{*}{CH}=CH-CH_2-, \text{ or}$$

$$-\underset{*}{CH}(OR_5)-CH_2-$$

wherein
$R_3$ represents a hydrogen atom or a methyl group,
$R_4$ represents a $C_{1-3}$ alkyl group or a phenyl group and
$R_5$ represents a hydrogen atom, a methyl or ethyl group and the carbon atom designated * is linked to the group $R_1$, and
$R_1$ represents a phenyl group optionally monosubstituted by a halogen atom or by a $C_{1-4}$-alkoxy group, a methyl, trifluoromethyl, phenyl, nitro, amino, dimethylamino, piperidino, acetylamino, methylthio, methylsulphinyl, methylsulphonyl, cyano, aminocarbonyl, carboxy, methoxycarbonyl, ethoxycarbonyl, benzyloxy, pyridylmethoxy or hydroxy group; a phenyl group disubstituted by methoxy, benzyloxy, hydroxy or methyl groups, whilst the substituents may be identical or different, or a phenyl group trisubstituted by three methoxy groups, by three hydroxy groups or by one hydroxy or amino group and by two chlorine or bromine atoms, a pyridyl group optionally substituted by a chlorine atom or by a methyl, methoxy, benzyloxy or hydroxy group, a naphthyl, quinolyl, isoquinolyl, indolyl, furyl, thienyl, (2-indolinon)yl, carbostyril or 3,4-dihydrocarbostyril group, a thiazolyl group optionally substituted in the 2-position by a methyl or amino group, a benzothiophenyl or benzofuranyl group, a benzothiazolyl, benzoxazolyl or benzimidazolyl group optionally substituted in the 2-position by a methyl, phenyl or amino group, or A represents a carbon-carbon bond and $R_1$ represents a 1H-inden-2-yl or 1,2-dihydronaphthalen-3-yl group or a 2H-1-benzopyran-3-yl or 2H-1-benzothiopyran-3-yl group optionally substituted by one or two methyl groups and $R_2$ represents a hydrogen atom or an acetyl or propionyl group optionally substituted in the omega-position by a phenyl or 4-methoxyphenyl group, and the acid addition salts thereof.

2. 4,5,7,8-tetrahydro-6H-thiazoloazepines of general formula II as recited in claim 1, wherein A represents a group of formulae

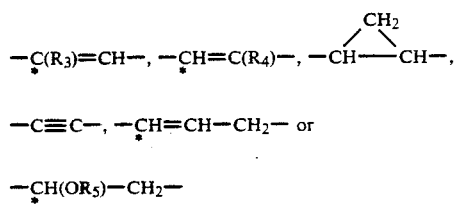

wherein $R_3$ represents a hydrogen atom or a methyl group, $R_4$ represents a $C_{1-3}$-alkyl group or a phenyl group and $R_5$ represents a hydrogen atom, a methyl or ethyl group and the carbon atom designated * is linked to the group $R_1$, and $R_1$ represents a phenyl group optionally substituted by a fluorine, chlorine or bromine atom, or by an alkoxy group with 1 to 4 carbon atoms, a methyl, trifluoromethyl, phenyl, hydroxy, benzyloxy, nitro, amino, dimethylamino, piperidino, cyano, aminocarbonyl, methoxycarbonyl, ethoxycarbonyl, methylmercapto, methylsulphinyl, methylsulphonyl or pyridylmethoxy group; a dimethoxyphenyl, dihydroxyphenyl, 4-hydroxy-3,5-dichlorophenyl, 4-hydroxy-3,5-dibromophenyl, 4-amino-3,5-dichlorophenyl, 4-amino-3,5-dibromo-phenyl, 3,4,5-trimethoxy-phenyl, naphthyl, 6-chloro-2-pyridyl, thienyl, furyl, quinolyl, isoquinolyl, benzothiophenyl, indolyl or indolin-2-on-4-yl group or a pyridyl group optionally substituted by a methyl group or A represents a carbon-carbon bond and $R_1$ represents a 1H-inden-2-yl, 1,2-dihydronaphthalen-3-yl or 1-benzopyran-3-yl group, and the acid addition salts thereof.

3. 4,5,7,8-tetrahydro-6H-thiazoloazepines of general formula II as recited in claim 2, wherein $R_1$ and A are defined as in claim 2 and $R_2$ represents a hydrogen atom, and the acid addition salts thereof.

4. 4,5,7,8-tetrahydro-6H-thiazoloazepines of general formula II as recited in claim 2, wherein A represents a vinylene, ethynylene or cyclopropylene or group, $R_1$ represents a phenyl group optionally substituted by a chlorine atom or by a hydroxy, methoxy, benzyloxy, isobutoxy, phenyl, nitro, amino, cyano or piperidino group; a pyridyl group optionally substituted by a methyl group, or a dimethoxyphenyl, naphthyl, isoquinolyl, 2-methyl-thiazolyl, furyl or thienyl group and $R_2$ represents a hydrogen atom, and the acid addition salts thereof.

5. 2-amino-6-(3-(4-cyano-phenyl)allyl)-4,5,7,8-tetrahydro-6H-thiazoloazepine and the acid addition salts thereof.

6. 2-amino-6-(3-(3-benzyloxy-phenyl)allyl)-4,5,7,8-tetrahydro-6H-thiazoloazepine and the acid addition salts thereof.

7. 2-amino-6-(3-(1-naphthyl)allyl)-4,5,7,8-tetrahydro-6H-thiazoloazepine and the acid addition salts thereof.

8. The physiologically acceptable acid addition salts with organic or inorganic acids of the compounds as recited in claim 1.

9. A pharmaceutical composition of matter useful in the treatment of ischaemia and cardiogenic shock which comprises a 4,5,7,8-tetrahydro-6H-thiazoloazepine as recited in claim 1 and a pharmaceutically acceptable carrier or diluent.

10. A pharmaceutical composition of matter useful in the treatment of Parkinson's disease, hyperprolactinaemia and schizophrenia which comprises a 4,5,7,8-tetrahydro-6H-thiazoloazepine as recited in claim 1 and a pharmaceutically acceptable carrier or diluent.

11. A method for treating ischaemia and cardiogenic shock in a warm-blooded animal which comprises administering to said animal a therapeutically effective amount of a 4,5,7,8-tetrahydro-6H-thiazoloazepine as recited in claim 1.

12. A method for treating Parkinson's disease, hyperprolactinaemia and schizophreina in a warm-blooded animal which comprises administering to said animals an effective amount of a 4,5,7,8-tetrahydro-6H-thiazoloazepine as recited in claim 1.

* * * * *